(12) United States Patent
Marsteller et al.

(10) Patent No.: US 10,022,558 B1
(45) Date of Patent: Jul. 17, 2018

(54) METHODS AND DEVICES FOR MINIMALLY-INVASIVE DELIVERY OF RADIATION TO THE EYE

(71) Applicant: Salutaris Medical Devices, Inc., Tucson, AZ (US)

(72) Inventors: Laurence J. Marsteller, Tucson, AZ (US); Russell J. Hamilton, Tucson, AZ (US); Luca Brigatti, Rockville, MD (US); Michael Voevodsky, Grand Rapids, MI (US)

(73) Assignee: Salutaris Medical Devices, Inc., Tucson, AZ (US)

( * ) Notice: Subject to any disclaimer, the term of this patent is extended or adjusted under 35 U.S.C. 154(b) by 217 days.

(21) Appl. No.: 15/004,538

(22) Filed: Jan. 22, 2016

Related U.S. Application Data

(60) Continuation-in-part of application No. 13/953,528, filed on Jul. 29, 2013, now abandoned, and a continuation-in-part of application No. 13/872,941, filed on Apr. 29, 2013, now abandoned, and a continuation-in-part of application No. 14/486,401, filed on Sep. 15, 2014, now Pat. No. 9,873,001, which is a continuation-in-part of application No. 14/011,516, filed on Aug. 27, 2013, now Pat. No. 9,056,201, and a continuation-in-part of application (Continued)

(51) Int. Cl.
*A61M 36/04* (2006.01)
*A61N 5/10* (2006.01)

(52) U.S. Cl.
CPC ......... *A61N 5/1017* (2013.01); *A61N 5/1007* (2013.01)

(58) Field of Classification Search
CPC .. A61N 5/1007; A61N 5/1014; A61N 5/1017; A61N 5/10–5/1084; A61N 2005/1008
See application file for complete search history.

(56) References Cited

U.S. PATENT DOCUMENTS 2,309,302 A   1/1943   Butler et al.
2,559,793 A   7/1951   Pregel
(Continued)

FOREIGN PATENT DOCUMENTS

AU   323700 S   1/2009
AU   323701 S   1/2009
(Continued)

OTHER PUBLICATIONS

Ghava et al.; Periocular routes for retinal drug delivery, 2004, pp. 99-114, Ashley Publications.
(Continued)

*Primary Examiner* — Catherine B Kuhlman
(74) *Attorney, Agent, or Firm* — Nguyen & Tarbet Law Firm

(57) ABSTRACT

Methods and devices for minimally-invasive delivery of radiation to the posterior portion of the eye including a cannula comprising a distal portion connected to a proximal portion and a means for advancing a radionuclide brachytherapy source (RBS) toward the tip of the distal portion; a method of introducing radiation to the human eye comprising inserting a cannula between the Tenon's capsule and the sclera of the human eye and emitting the radiation from the cannula.

15 Claims, 32 Drawing Sheets

Related U.S. Application Data

No. 13/953,528, filed on Jul. 29, 2013, now abandoned, and a continuation-in-part of application No. 13/872,941, filed on Apr. 29, 2013, now abandoned, said application No. 14/011,516 is a continuation-in-part of application No. 13/953,528, filed on Jul. 29, 2013, now abandoned, said application No. 14/011,516 is a continuation-in-part of application No. 13/872,941, filed on Apr. 29, 2013, now abandoned, which is a division of application No. 12/350,079, filed on Jan. 7, 2009, now Pat. No. 8,430,804, said application No. 14/011,516 is a continuation-in-part of application No. 13/742,823, filed on Jan. 16, 2013, now Pat. No. 8,597,169, which is a continuation of application No. 12/497,644, filed on Jul. 3, 2009, now abandoned, which is a continuation-in-part of application No. 12/350,079, filed on Jan. 7, 2009, now Pat. No. 8,430,804, said application No. 14/011,516 is a continuation-in-part of application No. 13/111,780, filed on May 19, 2011, now Pat. No. 8,608,632, which is a continuation-in-part of application No. 12/497,644, filed on Jul. 3, 2009, now abandoned, which is a continuation-in-part of application No. 12/350,079, filed on Jan. 7, 2009, now Pat. No. 8,430,804, said application No. 14/011,516 is a continuation-in-part of application No. 12/917,044, filed on Nov. 1, 2010, now abandoned, said application No. 14/011,516 is a continuation-in-part of application No. 13/111,765, filed on May 19, 2011, now Pat. No. 8,602,959.

(60) Provisional application No. 61/877,765, filed on Sep. 13, 2013, provisional application No. 61/676,783, filed on Jul. 27, 2012, provisional application No. 61/347,226, filed on May 21, 2010, provisional application No. 61/010,322, filed on Jan. 7, 2008, provisional application No. 61/033,238, filed on Mar. 3, 2008, provisional application No. 61/035,371, filed on Mar. 10, 2008, provisional application No. 61/047,693, filed on Apr. 24, 2008, provisional application No. 61/376,115, filed on Aug. 23, 2010, provisional application No. 61/257,232, filed on Nov. 2, 2009, provisional application No. 61/347,233, filed on May 21, 2010.

(56) References Cited

U.S. PATENT DOCUMENTS

| | | |
|---|---|---|
| D183,820 S | 10/1958 | Yohe |
| 3,169,527 A | 2/1965 | Sheridan |
| 3,662,882 A | 5/1972 | Obermayer |
| D235,171 S | 5/1975 | Boone |
| D235,172 S | 5/1975 | Boone |
| D236,920 S | 9/1975 | Sheridan |
| 3,974,322 A | 8/1976 | Drabkina |
| 4,248,354 A | 2/1981 | Metzger |
| 4,300,557 A | 11/1981 | Refojo et al. |
| D272,089 S | 1/1984 | Glassman |
| 4,925,450 A | 5/1990 | Imonti et al. |
| 4,976,266 A | 12/1990 | Huffman et al. |
| 5,007,689 A | 4/1991 | Kelly et al. |
| 5,109,844 A | 5/1992 | de Juan, Jr. et al. |
| 5,127,831 A | 7/1992 | Bab |
| 5,167,647 A | 12/1992 | Wijkamp et al. |
| 5,199,939 A | 4/1993 | Dake et al. |
| D340,111 S | 10/1993 | Yoshikawa |
| D345,417 S | 3/1994 | Sharipov |
| D347,473 S | 5/1994 | Nitzsche |
| 5,342,283 A | 8/1994 | Good |
| 5,364,374 A | 11/1994 | Morrison et al. |
| 5,392,914 A | 2/1995 | Lemieux et al. |
| 5,399,298 A | 3/1995 | Kelly et al. |
| 5,407,441 A | 4/1995 | Greenbaum |
| 5,637,073 A | 6/1997 | Freire |
| D390,656 S | 2/1998 | Linder |
| 5,871,481 A | 2/1999 | Kannenberg et al. |
| 5,893,873 A | 4/1999 | Rader et al. |
| 5,935,155 A | 8/1999 | Humayun et al. |
| 5,944,747 A | 8/1999 | Greenberg et al. |
| 5,947,891 A | 9/1999 | Morrison |
| 5,970,457 A | 10/1999 | Brant et al. |
| 6,013,020 A | 1/2000 | Meloul et al. |
| 6,053,900 A | 4/2000 | Brown et al. |
| D428,140 S | 7/2000 | Swan |
| 6,135,984 A | 10/2000 | Dishier |
| 6,149,643 A | 11/2000 | Herekar et al. |
| 6,159,205 A | 12/2000 | Herekar et al. |
| 6,183,410 B1 | 2/2001 | Jacobsen et al. |
| 6,183,435 B1 | 2/2001 | Bumbalough et al. |
| 6,278,975 B1 | 8/2001 | Brant et al. |
| 6,302,839 B1 | 10/2001 | Chernomorsky et al. |
| 6,402,734 B1 | 6/2002 | Weiss |
| 6,413,245 B1 * | 7/2002 | Yaacobi ............ A61F 9/0017 604/264 |
| 6,443,881 B1 | 9/2002 | Finger |
| 6,450,938 B1 | 9/2002 | Miller |
| 6,527,692 B1 | 3/2003 | Weinberger |
| 6,575,887 B1 | 6/2003 | Schrayer |
| 6,613,026 B1 | 9/2003 | Palasis et al. |
| 6,641,518 B2 | 11/2003 | Wolfson et al. |
| 6,676,590 B1 | 1/2004 | Urick et al. |
| 6,719,750 B2 | 4/2004 | Varner et al. |
| 6,749,553 B2 | 6/2004 | Brauckman et al. |
| 6,755,338 B2 | 6/2004 | Hahnen et al. |
| D492,778 S | 7/2004 | Narini |
| 6,800,076 B2 | 10/2004 | Humayun |
| 6,824,532 B2 | 11/2004 | Gillis et al. |
| 6,830,174 B2 | 12/2004 | Hillstead et al. |
| 6,875,165 B2 | 4/2005 | Dejuan, Jr. et al. |
| 6,918,894 B2 | 7/2005 | Fleury et al. |
| 6,958,055 B2 | 10/2005 | Donnan et al. |
| 6,964,653 B2 | 11/2005 | Negron |
| 6,977,264 B2 | 12/2005 | Fotsch et al. |
| 7,070,556 B2 | 7/2006 | Anderson et al. |
| 7,103,416 B2 | 9/2006 | Ok et al. |
| 7,115,607 B2 | 10/2006 | Fotsch et al. |
| 7,153,316 B1 | 12/2006 | McDonald |
| D534,650 S | 1/2007 | Inman et al. |
| D543,626 S | 5/2007 | Watschke et al. |
| 7,217,263 B2 | 5/2007 | Humayun et al. |
| 7,220,225 B2 | 5/2007 | Dejuan, Jr. et al. |
| 7,223,225 B2 | 5/2007 | DeJuan, Jr. et al. |
| 7,228,181 B2 | 6/2007 | Greenberg et al. |
| 7,252,006 B2 | 8/2007 | Tai et al. |
| 7,273,445 B2 | 9/2007 | Pulido et al. |
| D553,738 S | 10/2007 | Simpson |
| 7,276,019 B2 | 10/2007 | DeJuan, Jr. et al. |
| 7,308,487 B1 | 12/2007 | Dansie et al. |
| 7,321,796 B2 | 1/2008 | Fink et al. |
| 7,351,193 B2 | 4/2008 | Foreman et al. |
| 7,357,770 B1 | 4/2008 | Cutrer et al. |
| 7,402,155 B2 | 7/2008 | Palasis et al. |
| D575,396 S | 8/2008 | Wu |
| 7,485,113 B2 | 2/2009 | Varner et al. |
| 7,503,474 B2 | 3/2009 | Hillstead et al. |
| 7,537,593 B2 | 5/2009 | Humayun |
| 7,547,323 B2 | 6/2009 | Lavigne |
| 7,560,460 B2 | 7/2009 | Fotsch et al. |
| 7,563,222 B2 | 7/2009 | Larsen et al. |
| 7,571,004 B2 | 8/2009 | Roy et al. |
| 7,579,347 B2 | 8/2009 | Bo et al. |
| 7,600,533 B2 | 10/2009 | Tai et al. |
| 7,654,716 B1 | 2/2010 | Bhadri et al. |
| 7,661,676 B2 | 2/2010 | Smith et al. |
| 7,684,868 B2 | 3/2010 | Tai et al. |
| D615,645 S | 5/2010 | Brigatti et al. |
| D616,087 S | 5/2010 | Brigatti et al. |
| D616,088 S | 5/2010 | Brigatti et al. |
| D616,540 S | 5/2010 | Brigatti et al. |

(56) References Cited

U.S. PATENT DOCUMENTS

| | | |
|---|---|---|
| 7,729,739 B2 | 6/2010 | Acar et al. |
| 7,744,520 B2 | 6/2010 | Larsen et al. |
| 7,774,931 B2 | 8/2010 | Tai et al. |
| 7,794,437 B2 | 9/2010 | Humayun et al. |
| 7,803,102 B2 | 9/2010 | Larsen et al. |
| 7,803,103 B2 | 9/2010 | Hillstead et al. |
| 7,810,233 B2 | 10/2010 | Krulevitch et al. |
| 7,827,038 B2 | 11/2010 | Richard et al. |
| 7,831,309 B1 | 11/2010 | Humayun et al. |
| 7,842,686 B2 | 11/2010 | Anderson et al. |
| 7,846,954 B2 | 12/2010 | Zimmermann et al. |
| 7,879,564 B2 | 2/2011 | Brice et al. |
| 7,883,717 B2 | 2/2011 | Varner et al. |
| 7,887,508 B2 | 2/2011 | Meng et al. |
| 7,909,816 B2 | 3/2011 | Buzawa |
| D642,266 S | 7/2011 | Marsteller et al. |
| D691,267 S | 10/2013 | Marsteller et al. |
| D691,268 S | 10/2013 | Marsteller et al. |
| D691,269 S | 10/2013 | Marsteller et al. |
| D691,270 S | 10/2013 | Marsteller et al. |
| 8,597,169 B2 | 12/2013 | Brigatti et al. |
| 8,602,959 B1 | 12/2013 | Park et al. |
| 8,608,632 B1 | 12/2013 | Brigatti et al. |
| 9,056,201 B1 | 6/2015 | Hamilton et al. |
| 2001/0008950 A1 | 7/2001 | Vitali et al. |
| 2001/0049464 A1 | 12/2001 | Ganz |
| 2002/0002362 A1 | 1/2002 | Humayun et al. |
| 2002/0026174 A1 | 2/2002 | Wallace |
| 2002/0062136 A1 | 5/2002 | Hillstead et al. |
| 2002/0065448 A1 | 5/2002 | Bradshaw et al. |
| 2002/0077687 A1 | 6/2002 | Ahn |
| 2002/0099363 A1 | 7/2002 | Woodward et al. |
| 2002/0115902 A1 | 8/2002 | Dejuan, Jr. et al. |
| 2002/0164061 A1 | 11/2002 | Paik et al. |
| 2002/0198511 A1 | 12/2002 | Varner et al. |
| 2003/0014306 A1 | 1/2003 | Marko |
| 2003/0045900 A1 | 3/2003 | Hahnen et al. |
| 2003/0103945 A1 | 6/2003 | Chen et al. |
| 2003/0153804 A1 | 8/2003 | Tomes et al. |
| 2003/0171722 A1 | 9/2003 | Paques et al. |
| 2003/0184859 A1 | 10/2003 | Liang et al. |
| 2003/0195201 A1 | 10/2003 | Bo et al. |
| 2003/0220324 A1 | 11/2003 | Fotsch et al. |
| 2004/0006067 A1 | 1/2004 | Fotsch et al. |
| 2004/0039312 A1 | 2/2004 | Hillstead et al. |
| 2004/0053309 A1 | 3/2004 | Holt et al. |
| 2004/0133155 A1 | 7/2004 | Varner et al. |
| 2004/0138515 A1 | 7/2004 | White et al. |
| 2004/0224777 A1 | 11/2004 | Smith et al. |
| 2004/0243176 A1 | 12/2004 | Hahnen et al. |
| 2005/0059956 A1 | 3/2005 | Varner et al. |
| 2005/0085415 A1 | 4/2005 | Wiesner et al. |
| 2005/0101824 A1 | 5/2005 | Stubbs |
| 2005/0107824 A1 | 5/2005 | Hillstead et al. |
| 2005/0148948 A1 | 7/2005 | Caputa |
| 2005/0149286 A1 | 7/2005 | Acar et al. |
| 2005/0177019 A1 | 8/2005 | DeJuan, Jr. et al. |
| 2005/0203331 A1 | 9/2005 | Szapucki et al. |
| 2005/0227986 A1 | 10/2005 | Bo et al. |
| 2005/0272931 A1 | 12/2005 | Bo et al. |
| 2005/0277802 A1 | 12/2005 | Larsen et al. |
| 2006/0009493 A1 | 1/2006 | Koenig et al. |
| 2006/0030618 A1 | 2/2006 | Bo et al. |
| 2006/0047255 A1 | 3/2006 | Kiehlbauch et al. |
| 2006/0052796 A1 | 3/2006 | Perez et al. |
| 2006/0078087 A1* | 4/2006 | Forman ............... A61N 5/1001 378/65 |
| 2006/0110428 A1 | 5/2006 | deJuan et al. |
| 2006/0111605 A1 | 5/2006 | Larsen et al. |
| 2006/0142629 A1 | 6/2006 | DeJuan, Jr. et al. |
| 2006/0189838 A1 | 8/2006 | Dejuan, Jr. et al. |
| 2006/0223026 A1 | 10/2006 | Kuroiwa et al. |
| 2006/0235877 A1 | 10/2006 | Richard et al. |
| 2006/0257451 A1 | 11/2006 | Varner et al. |
| 2006/0287662 A1 | 12/2006 | Berry et al. |
| 2007/0019790 A1 | 1/2007 | Lewis et al. |
| 2007/0055089 A1 | 3/2007 | Larsen et al. |
| 2007/0118010 A1 | 5/2007 | Hillstead et al. |
| 2007/0179471 A1 | 8/2007 | Christian et al. |
| 2007/0191863 A1 | 8/2007 | De Juan |
| 2007/0219546 A1 | 9/2007 | Mody et al. |
| 2007/0233037 A1 | 10/2007 | Gifford, III et al. |
| 2007/0248545 A1 | 10/2007 | Brice et al. |
| 2007/0265248 A1 | 11/2007 | Fotsch et al. |
| 2007/0265485 A1 | 11/2007 | DeJuan, Jr. et al. |
| 2008/0027266 A1 | 1/2008 | Lebovic et al. |
| 2008/0058704 A1* | 3/2008 | Hee .................. A61F 9/0017 604/21 |
| 2008/0089480 A1 | 4/2008 | Gertner |
| 2008/0108933 A1 | 5/2008 | Yu et al. |
| 2008/0154204 A1 | 6/2008 | Varner et al. |
| 2008/0161762 A1 | 7/2008 | Stehr et al. |
| 2008/0172086 A1 | 7/2008 | Hillstead et al. |
| 2008/0200747 A1 | 8/2008 | Wagner et al. |
| 2008/0214887 A1 | 9/2008 | Heanue et al. |
| 2008/0221653 A1 | 9/2008 | Agrawal et al. |
| 2008/0249412 A1 | 10/2008 | Huang et al. |
| 2008/0262512 A1 | 10/2008 | Humayun et al. |
| 2008/0262569 A1 | 10/2008 | Greenberg et al. |
| 2008/0262570 A1 | 10/2008 | Greenberg et al. |
| 2008/0262571 A1 | 10/2008 | Greenberg et al. |
| 2008/0272023 A1 | 11/2008 | McCormick et al. |
| 2008/0281142 A1 | 11/2008 | Lubock et al. |
| 2008/0281254 A1 | 11/2008 | Humayun et al. |
| 2008/0288036 A1 | 11/2008 | Greenberg et al. |
| 2008/0294223 A1 | 11/2008 | Greenberg et al. |
| 2008/0305320 A1 | 12/2008 | Laude et al. |
| 2008/0306611 A1 | 12/2008 | Rowley et al. |
| 2008/0319319 A1 | 12/2008 | Humayun et al. |
| 2009/0016075 A1 | 1/2009 | Bhadri et al. |
| 2009/0030323 A1 | 1/2009 | Fawzi et al. |
| 2009/0036827 A1 | 2/2009 | Cazzini |
| 2009/0069340 A1 | 3/2009 | Balestra et al. |
| 2009/0088784 A1 | 4/2009 | DeBoer et al. |
| 2009/0088843 A1 | 4/2009 | Lu et al. |
| 2009/0101841 A1 | 4/2009 | Boyden et al. |
| 2009/0104960 A1 | 4/2009 | Kelly et al. |
| 2009/0104987 A1 | 4/2009 | Kelly et al. |
| 2009/0112287 A1 | 4/2009 | Greenberg et al. |
| 2009/0131175 A1 | 5/2009 | Kelly et al. |
| 2009/0143124 A1 | 6/2009 | Hughes et al. |
| 2009/0143633 A1 | 6/2009 | Edmundson et al. |
| 2009/0143734 A1 | 6/2009 | Humayun et al. |
| 2009/0146583 A1 | 6/2009 | Bhadri et al. |
| 2009/0149915 A1 | 6/2009 | Greenberg et al. |
| 2009/0177245 A1 | 7/2009 | Ameri et al. |
| 2009/0192493 A1 | 7/2009 | Meng et al. |
| 2009/0227856 A1 | 9/2009 | Russell et al. |
| 2009/0228086 A1 | 9/2009 | Greenberg et al. |
| 2009/0240215 A1 | 9/2009 | Humayun et al. |
| 2009/0264424 A1 | 10/2009 | Bo et al. |
| 2009/0287276 A1 | 11/2009 | Greenberg et al. |
| 2009/0306585 A1 | 12/2009 | Pang et al. |
| 2009/0306594 A1 | 12/2009 | Pang et al. |
| 2009/0306595 A1 | 12/2009 | Shih et al. |
| 2009/0311133 A1 | 12/2009 | Pang et al. |
| 2009/0312742 A1 | 12/2009 | Pang et al. |
| 2010/0004499 A1 | 1/2010 | Brigatti et al. |
| 2010/0004581 A1 | 1/2010 | Brigatti et al. |
| 2010/0004639 A1 | 1/2010 | Pang et al. |
| 2010/0025613 A1 | 2/2010 | Tai et al. |
| 2010/0026957 A1 | 2/2010 | Tanguay, Jr. et al. |
| 2010/0030010 A1 | 2/2010 | Vermeere et al. |
| 2010/0076271 A1 | 3/2010 | Humayun |
| 2010/0100104 A1 | 4/2010 | Yu et al. |
| 2010/0105454 A1 | 4/2010 | Weber et al. |
| 2010/0114039 A1 | 5/2010 | Cazzini |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0131075 A1 | 5/2010 | Ludlow et al. |
| 2010/0157620 A1 | 6/2010 | Bhadri et al. |
| 2010/0168646 A1 | 7/2010 | Greenbaum et al. |
| 2010/0174415 A1 | 7/2010 | Humayun et al. |

(56) References Cited

U.S. PATENT DOCUMENTS

| | | |
|---|---|---|
| 2010/0197826 A1 | 8/2010 | Agrawal et al. |
| 2010/0228119 A1 | 9/2010 | Brennan et al. |
| 2010/0228123 A1 | 9/2010 | Brennan et al. |
| 2010/0228124 A1 | 9/2010 | Brennan et al. |
| 2010/0228132 A1 | 9/2010 | Brennan et al. |
| 2010/0228238 A1 | 9/2010 | Brennan et al. |
| 2010/0229384 A1 | 9/2010 | Krulevitch et al. |
| 2010/0238288 A1 | 9/2010 | Klaemer et al. |
| 2010/0267647 A1 | 10/2010 | Greenbaum et al. |
| 2010/0268013 A1 | 10/2010 | Larsen et al. |
| 2010/0294041 A1 | 11/2010 | Tai et al. |
| 2010/0305550 A1 | 12/2010 | Meng et al. |
| 2011/0004045 A1 | 1/2011 | Larsen et al. |
| 2011/0021906 A1 | 1/2011 | Hillstead et al. |
| 2011/0207987 A1 | 8/2011 | DiCarlo |
| 2013/0267758 A1 | 10/2013 | Brigatti et al. |
| 2015/0265850 A1 | 9/2015 | Finger et al. |
| 2016/0375267 A1 | 12/2016 | Lutz et al. |

FOREIGN PATENT DOCUMENTS

| | | |
|---|---|---|
| AU | 323703 S | 1/2009 |
| AU | 323704 S | 1/2009 |
| WO | 200128473 A1 | 4/2001 |
| WO | 2005016258 A2 | 2/2005 |
| WO | 2007059208 A2 | 5/2007 |
| WO | 2008076544 A2 | 6/2008 |
| WO | 2009089288 A1 | 7/2009 |
| WO | 2011053908 A1 | 5/2011 |
| WO | 2015105539 A2 | 7/2015 |

OTHER PUBLICATIONS

Venkatesh et al.; Comparison of the Efficacy and Safety of Different Methods of Posterior Subtenon Injection; Ocular Immunology and Inflammation; Oct. 1, 2007; pp. 217-223; Inform Healthcare USA, Inc.

Tenon's Capsule; Fundamentals and Principles; p. 39.

Canavan et al.; Sub-Tenon's administration of local anaesthetic: a review of the technique; 2003; pp. 787-793; British Journal of Anaesthesia.

Dafflon et al.; Posterior sub-Tenon's steriod injections for the treatment of posterior ocular inflammation: indications, efficacy and side effects, Graefe's Arch Clin Exp Ophthalmos, 1999, pp. 289-295; Springer-Verlag 1999.

Tanner et al.; Posterior sub-Tenon's triamcinolone injections in the treatment of uveitis; Royal College of Ophthalmologists; 1998; pp. 679-685.

Thach, MD et al.; A Comparison of Retrobulbar versus Sub-Tenon's Corticosteroid Therapy for Cystoid Macular Edema Refractory to Topical Medications; pp. 2003-2008; Ophthalmology Volue 104, No. 12, Dec. 1997.

Hubbard et al.; A New Ocular Brachytherapy System for the Treatment of Exudative AMD; 2005; Invest Ophthalmo Vis Sci 2005; 46; E-Abstract 2425.

Hubbard, III et al.; A Progress Report on the TheraSight Ocular Brachytherapy Safety and Feasibility Study; 2006; Invest Ophthalmol Vis Sci 2006; 47: E-Abstract 2101.

The Collaborative Ocular Melanoma Study Group; Design and Methods of a Clinical Trial for a Rare condition: The Collaborative Ocular Melanoma Study; COMS Report No. 3; 1993; Controlled Clinical Trials 14: 362-391; Elsevier Science Publishing Co., Inc. Coms Coordinating Center; Collaborative Ocular Melanoma Study; Manual of Procedures; Jan. 1995; pp. 1-330; The Wilmer Ophthalmological Institute; The Johns Hopkins School of Medicine (*reduced to cover and Table of Contents due to excessive data [330 pages]).

Hubbard et al.; Cadaver Evaluation of a New Ocular Brachytherapy System; Invest Ophthalmol Vis Sci 2004; 45: E-Abstract 5139.

Golden; SubTenon Injection of Gentamicin for Bacterial Infections of the Eye; pp. S271-S277; The Journal of Infectious Diseases; vol. 124, Supplement; Dec. 1971; University of Chicago.

Snyder, MD, PhD et al.; Antibiotic Therapy for Ocular Infection; Conferences and Reviews; pp. 579-584; WJM, Dec. 1994; vol. 161, No. 6; Therapy for Ocular Infection—Snyder and Glasser.

Baum, M.D. et al.; The Evolution of Antibiotic Therapy for Facterial Conjunctivitis and Keratitis: 1970-2000; pp. 559-672; Cornea, vol. 19, No. 5, 2000; Lippincott Williams & Wilkins, Inc., Philadelphia.

Scoper; Review of Third- and Fourth-Generation Fluoroquinolones in Ophthalmology: In-Vitro and In-Vivo Efficacy; Adv Ther. 2008; 25(10): 979-994; Springer Healthcare Communications.

Yilmaz, MD et al.; Severe Fungal Keratitis Treated With Subconjunctival Fluconazole; 2003; pp. 454.e1-454.e7; vol. 140, No. 3; Elsevier Inc.

Yilmaz, MD et al.; Severe Fungal Keratitis Treated With Subconjunctival Fluconazole; Apr. 2006; pp. 783-784; vol. 141, No. 4, Correspondence; American Journal of Ophthalmology.

Ikewaki et al.; Peribulbar fungal abscess and endophthalmitis following posterior subtenon injection of triamcinolone acetonide; Diagnolis/Therapy in Ophthalmology; 2008; pp. 102-104; Acta Ophthalmologica; The Authors, Journal compilation, Acta Ophthalmol.

Nayak et al.; Acute orbital abscess complicating deep posterior subtenon triamcinolone injection; Indian Journal of Ophthalmology; vol. 56, No. 3; May-Jun. 2008; downloaded from http://www.ijo.in on Monday, Nov. 2, 2009.

Kusaka et al.; Orbital infection following posterior subtenon triamcinolone injection; 2207; pp. 692-693; Acta Ophthalmologica Scandinavica.

Walker et al.; Conservative management of refractory steroid-induced glaucoma following anterior subtenon steroid injection; 2007; Letters to the Editor; pp. 197-198; The Authors, Journal compilation, Royal Australian and New Zealand College of Ophthalmologists.

Au et al.; Localised abscess following an injection of subtenon triamcinolone acitonide; Correspondence; Eye (2007) 21, 627-674, doi:10.1038/sj.eye.6702671; published online Dec. 15, 2006.

Venkatesh MD, et al.; Posterior subtenon injection of corticosteroids using polytetrafluoroethylene (PEFE) intravenous cannula; Clinical and Experimental Ophthalmology (2002) 30, 55-57; All India Institute of Medical Sciences campus, India.

Sou-Tung Chiu-Tsao, Ph.D., Episcleral Eye Plaques for Treatment of Intraocular Malignancies and Benign Diseases; Chapter 34; pp. 673-705.

Sou-Tung Chiu-Tsao, Ph.D., Pterygium Brachytherapy Physics; Chapter 35; pp. 707-717.

Nath, Ravinder, Ph.D. et al.; Brachytherapy Physics Second Edition; Medical Physics Monograph No. 31; 1013 pages; Medical Physics Publishing; Madison, Wisconsin, USA; 2005.

Jaakkola, Aino; Heikkonen, Jorma; Tarkkanen, Anti and Immonen, Ilkka; Visual function after strontium-90 plaque irradiation in patients with age-related subfoveal choroidal neovascularization; Acta Opthalmologica Scandinavica 1999; 77; pp. 57-61.

Hokkanen, J.; Heikkonen, J.; Holmberg, P.; Theoretical calculations of dose distributions for beta-ray eye applicators; Med. Phys. 24 (2); Feb. 1997 pp. 211-213.

Jaakkola, Aino; Heikkonen, Jorma; Tommila, Petri; Laatikainen, Leila; Immonen, Ilkka; Strontium plaque irradiation of subfoveal neovascular membranes in age-related macular degeneration; Graefe's Arch Clin Exp Ophthalmol (1998); 236; pp. 24-30.

J. M. Capping; Radiation scleral necrosis simulating early scleromalacia perforans; Brit. J. Ophthal.; 1973; 57; pp. 425-428.

JC Wen et al; Ocular complications following I-125 brachytherapy for choroidal melanoma; Eye; 2009; 23; 1254-1268.

Messmer E et al.; Histopathologic findings in eyes treated with a ruthenium plaque for uveal melanoma; Graefes Arch Clin Exp Ophthalmol.; 1992; 230 (4): 391-6.

* cited by examiner

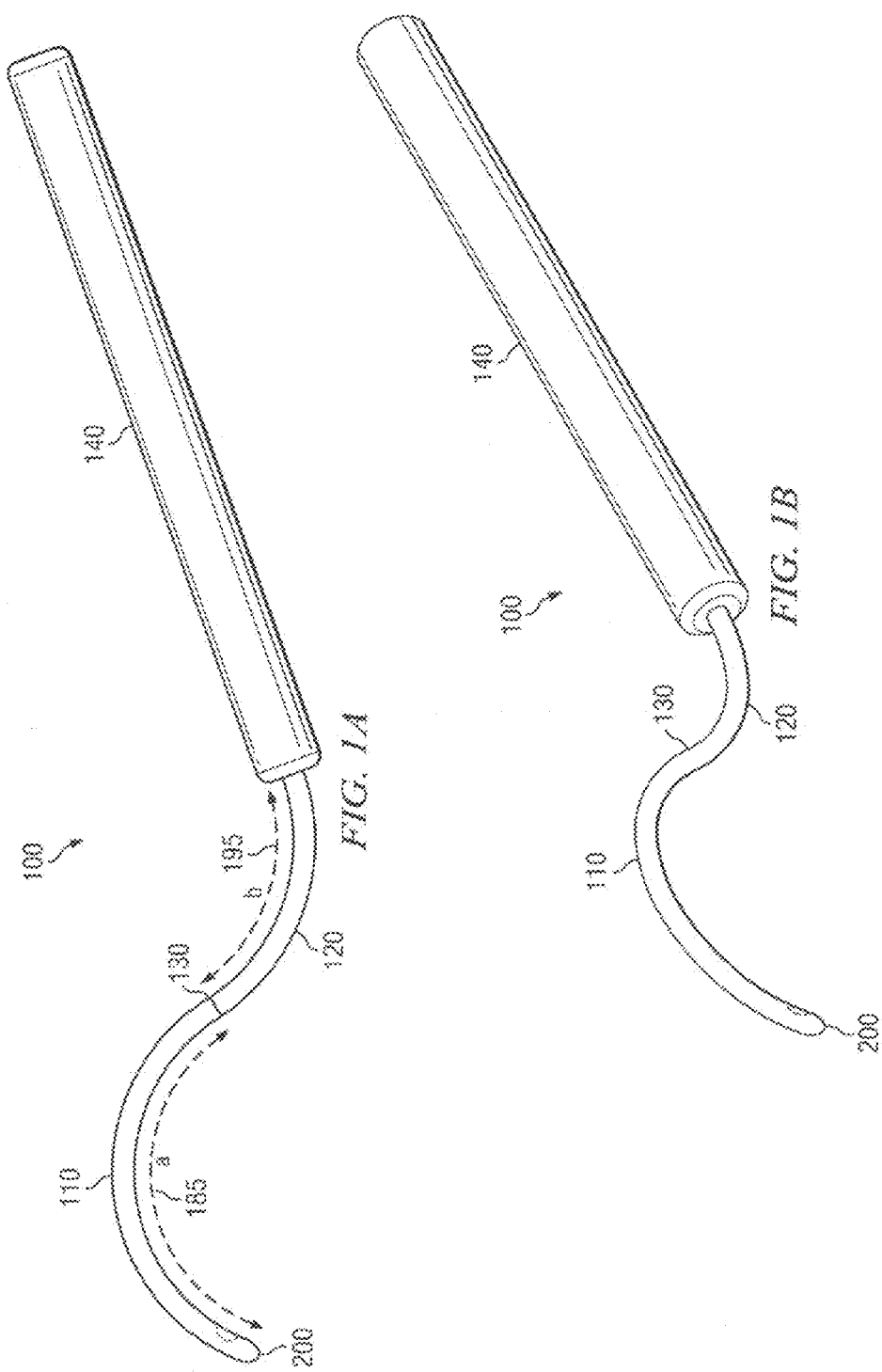

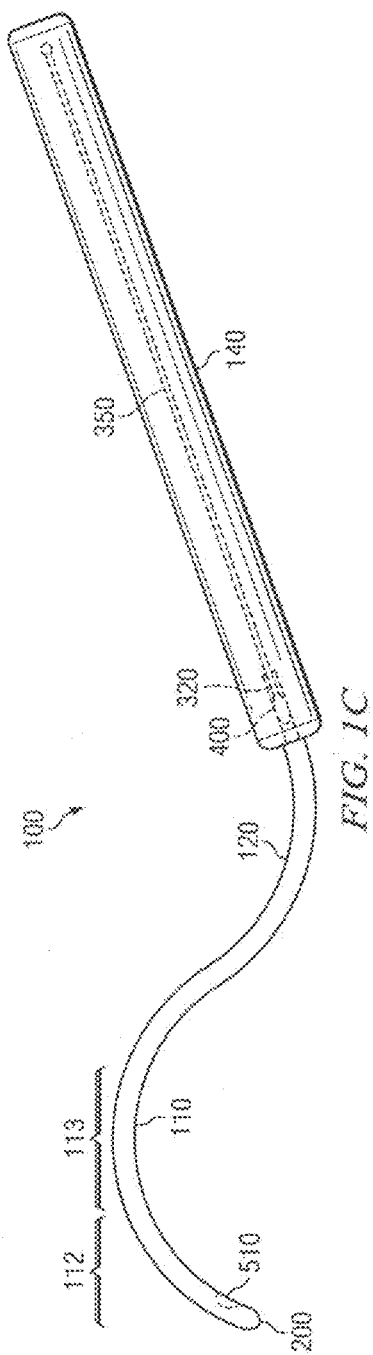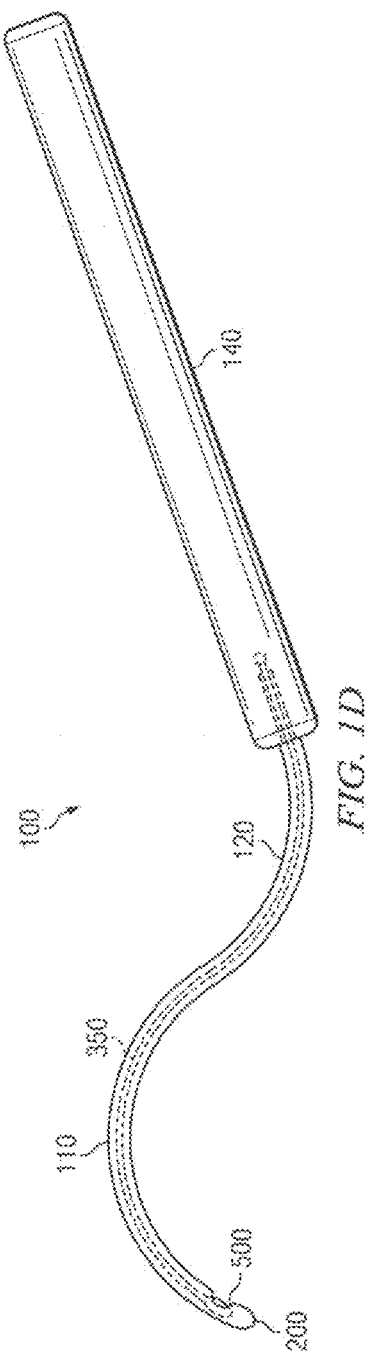

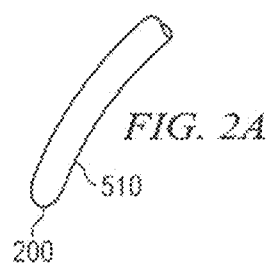
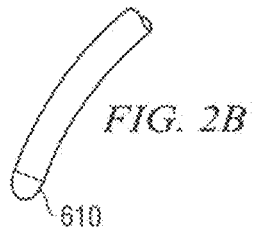
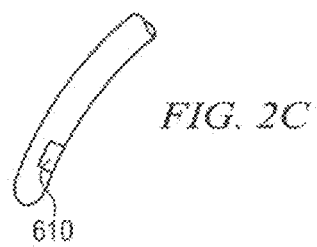
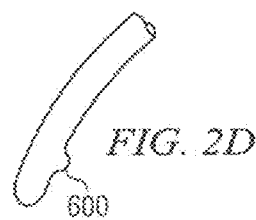
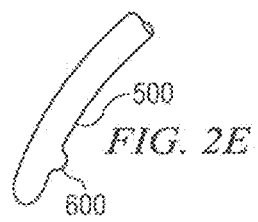
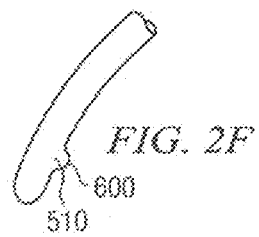
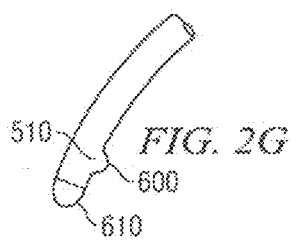
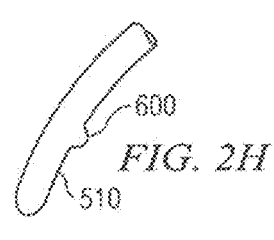
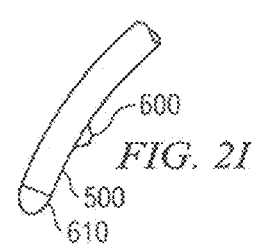
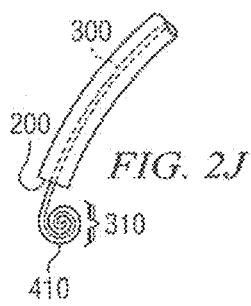
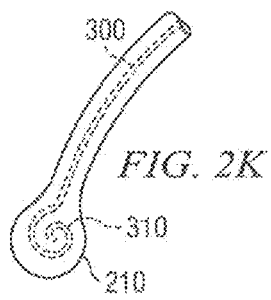
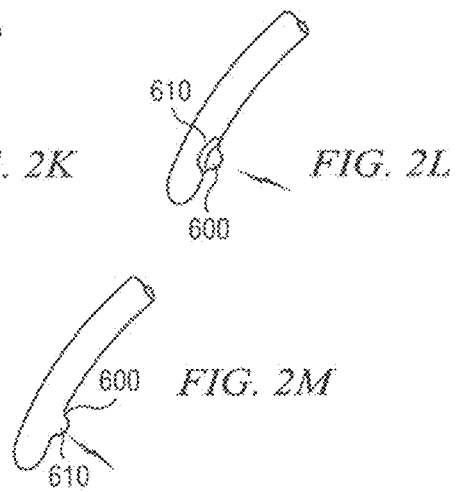

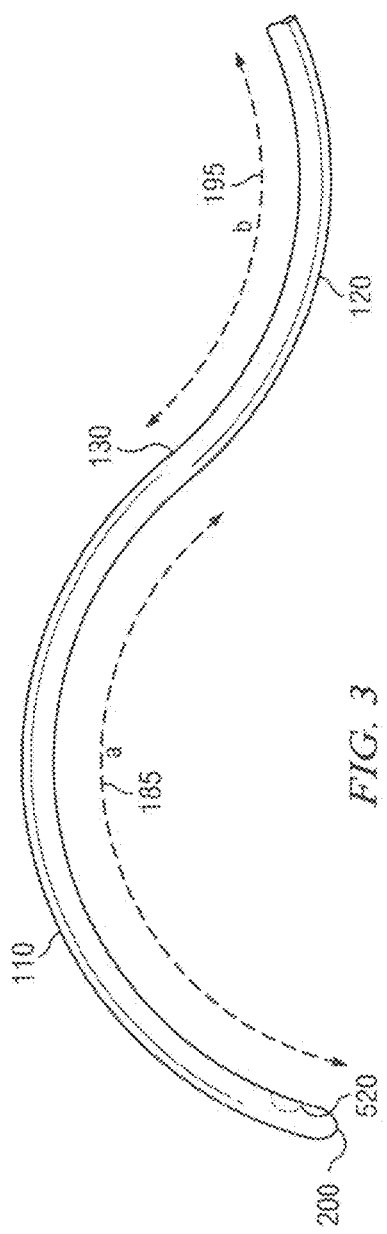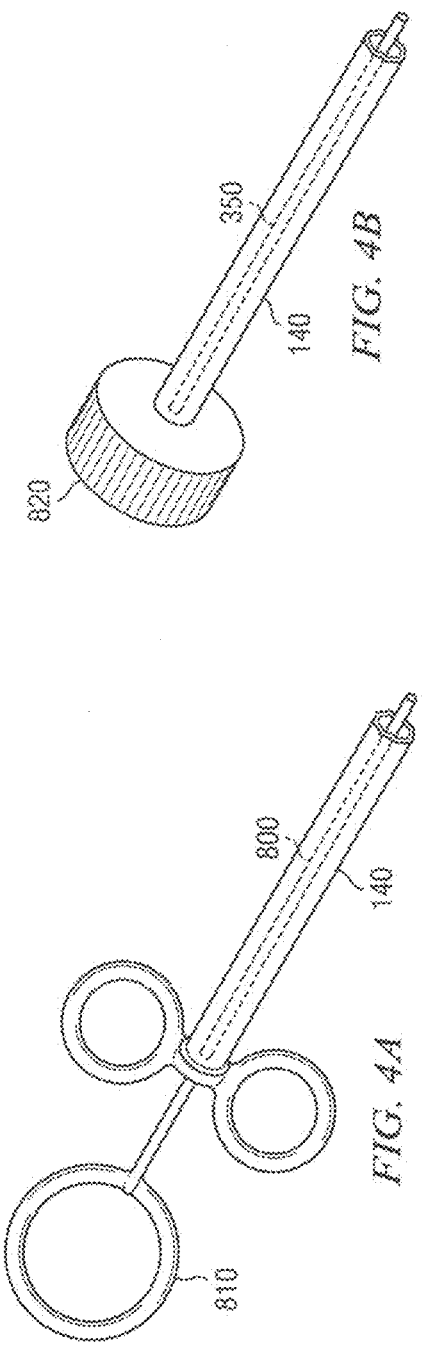

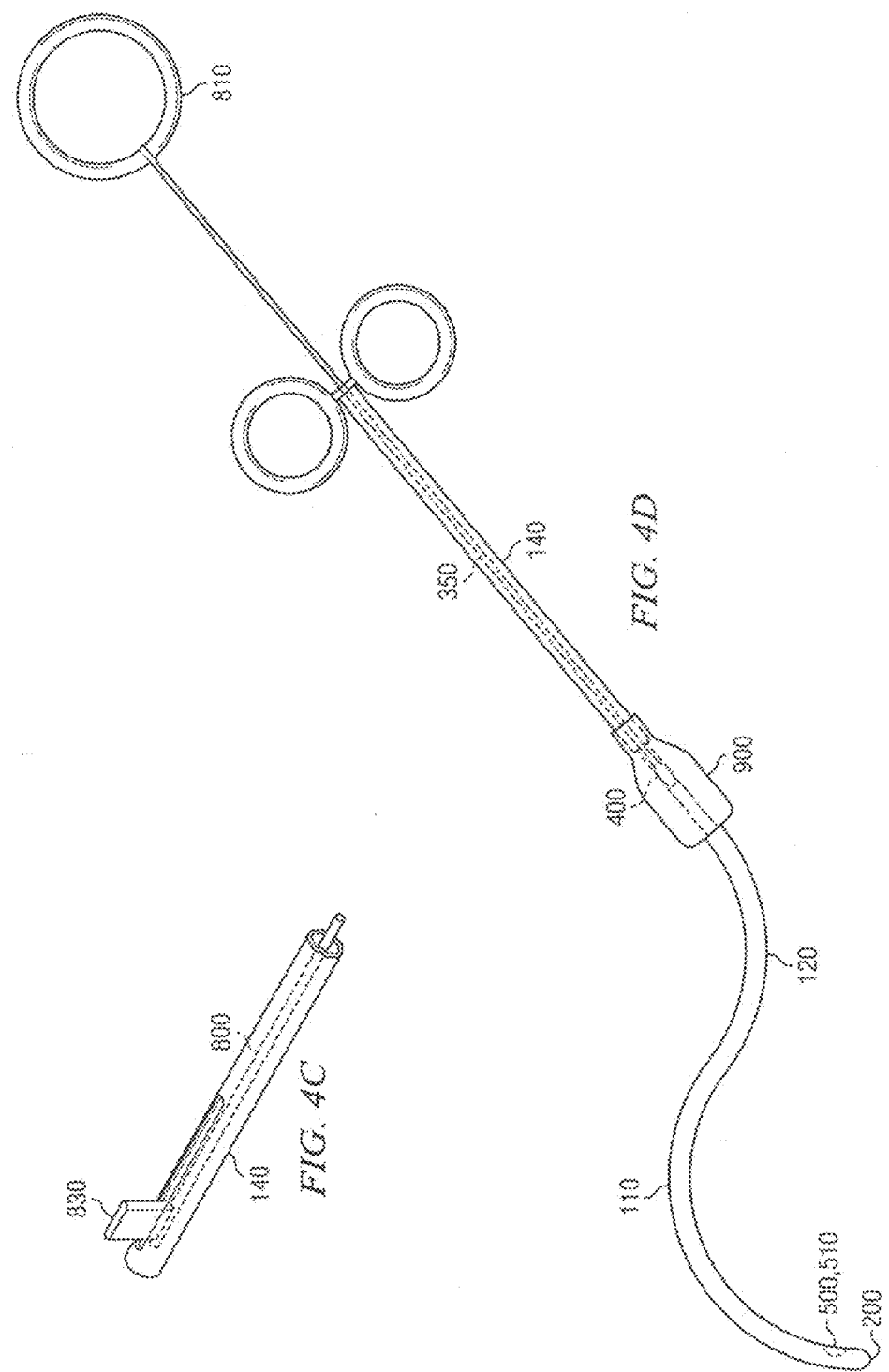

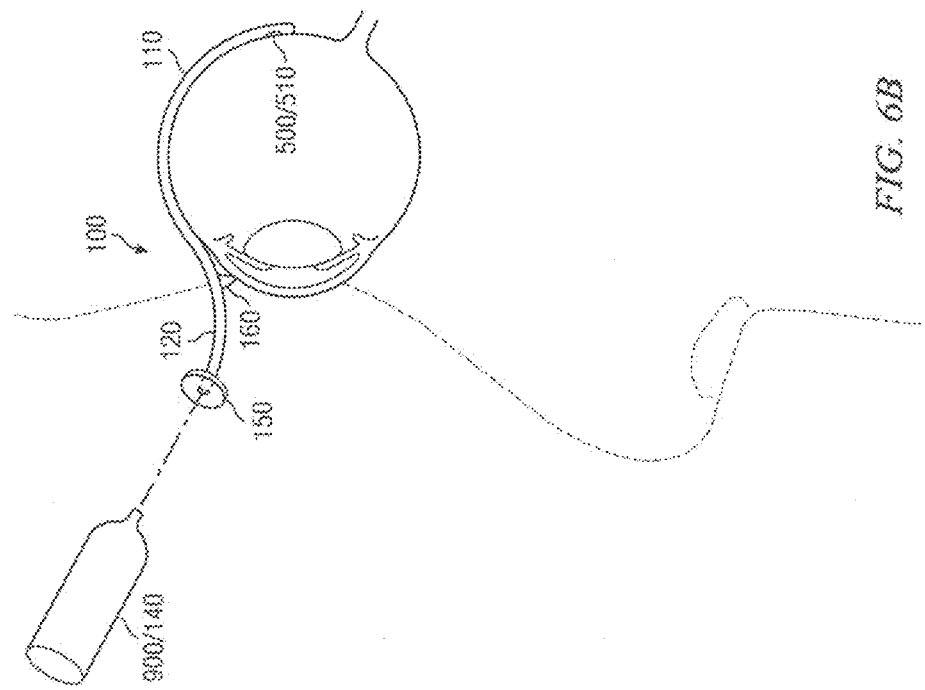
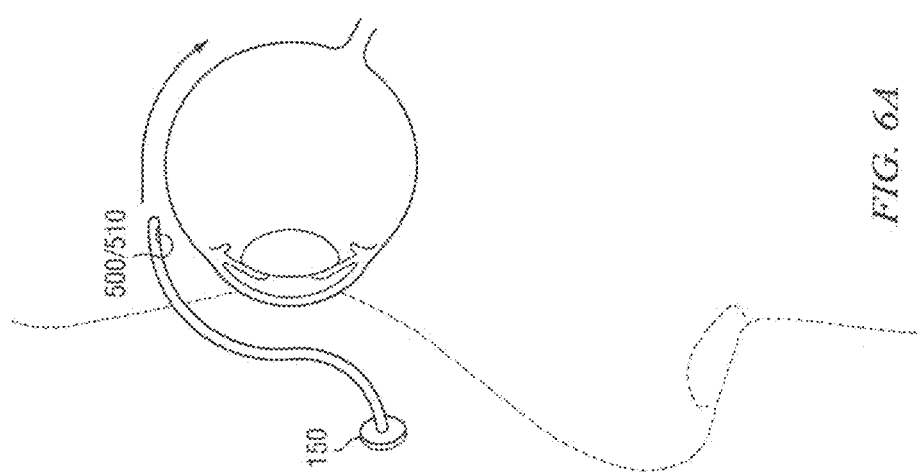
FIG. 6B
FIG. 6A

ROTATIONALLY SYMMETRICAL SHAPES

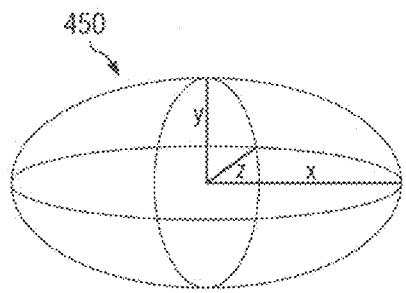
FIG. 15
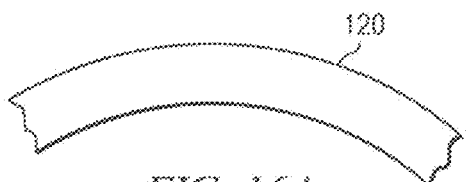
FIG. 16A
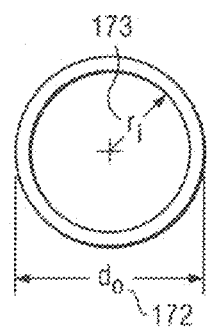 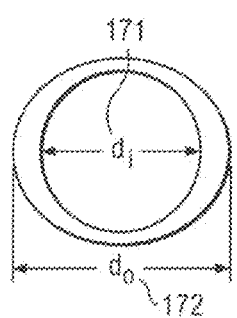 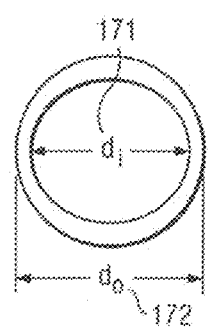
FIG. 16B     FIG. 16C     FIG. 16D TABLE 1 (dimensions in mm +/- 1 mm)

| A | b | c |
|---|---|---|
| 12 | 12 | 12 |
| 14 | 12 | 12 |
| 10 | 12 | 12 |
| 12 | 10 | 10 |
| 12 | 10 | 12 |
| 12 | 10 | 14 |
| 12 | 12 | 10 |
| 12 | 12 | 14 |
| 12 | 14 | 10 |
| 12 | 14 | 12 |
| 12 | 14 | 14 |
| 10 | 10 | 10 |
| 10 | 10 | 12 |
| 10 | 10 | 14 |
| 10 | 12 | 10 |
| 10 | 12 | 14 |
| 10 | 14 | 10 |
| 10 | 14 | 12 |
| 10 | 14 | 14 |
| 14 | 10 | 10 |
| 14 | 10 | 12 |
| 14 | 10 | 14 |
| 14 | 12 | 10 |
| 14 | 12 | 14 |
| 14 | 14 | 10 |
| 14 | 14 | 12 |
| 14 | 14 | 14 |

FIG. 26

TABLE 2 (dimensions in mm +/- 1 mm)

| D | e | f |
|---|---|---|
| 12 | 12 | 12 |
| 12 | 12 | 6 |
| 12 | 12 | 24 |
| 12 | 6 | 24 |
| 12 | 6 | 1000 |
| 12 | 24 | 1000 |
| 12 | 0 | 0 |
| 12 | 6 | 6 |
| 12 | 24 | 24 |
| 12 | 1000 | 1000 |

FIG. 27

TABLE 3

|  | Platinum | Gold | Stainless Steel | Titanium |
|---|---|---|---|---|
| Thickness (cm) | 0.01 | 0.01 | 0.033 | 0.07 |
| Density | 21.45 | 19.32 | 8.00 | 4.54 |
| Electron Energy | 0.6 | 0.6 | 0.6 | 0.6 |
| Radiative Stopping Power | 0.08662 | 0.08828 | 0.02811 | 0.02297 |
| Energy Lost | 0.01858 | 0.017056 | 0.007421 | 0.0073 |
| Fraction of Energy Lost | 0.030967 | 0.028426 | 0.012368 | 0.012166 |
| Mean Photon Energy | 0.2 | 0.2 | 0.2 | 0.2 |
| Attenuation Coefficient for water liquid | 0.137 | 0.137 | 0.137 | 0.137 |
| Fraction of photon energy lost at depth > 1cm | 0.87197 | 0.87197 | 0.87197 | 0.87197 |
| Fraction of initial electron energy lost at depth > 1cm | 0.027002 | 0.024787 | 0.010785 | 0.010609 |

FIG. 28

TABLE 4

| Depth (mm) (Distance away from source, as measured along line $l_R$) | Relative Radiation Dose |||
|---|---|---|---|
| | Sr-09 Source || P-32 Source |
| | 1.5mm size | 3.0mm size | 3.0mm size |
| 0.1 | 100 | 100 | 100 |
| 0.5 | 50.02 | 75.00 | 74.64 |
| 1.0 | 20.85 | 46.68 | 44.76 |
| 2.0 | 6.05 | 19.92 | 15.02 |
| 3.0 | 2.37 | 8.12 | 5.00 |
| 4.0 | 0.99 | 3.56 | 1.51 |
| 5.0 | 0.43 | 1.56 | 0.37 |
| 6.0 | 0.18 | 0.66 | 0.08 |
| 7.0 | 0.07 | 0.26 | 0.02 |
| 8.0 | 0.02 | 0.07 | 0.01 |

FIG. 29

Axis of handle

METHODS AND DEVICES FOR MINIMALLY-INVASIVE DELIVERY OF RADIATION TO THE EYE

CROSS REFERENCE

This application is a continuation in-part and claims benefit of U.S. patent application Ser. No. 13/953,528, filed Jul. 29, 2013, which is a non-provisional of U.S. Provisional Application No. 61/676,783, filed Jul. 27, 2012, the specification(s) of which is/are incorporated herein in their entirety by reference.

This application is a continuation in-part and claims benefit of U.S. patent application Ser. No. 13/872,941, filed Apr. 29, 2013, which is a divisional of U.S. patent application Ser. No. 12/350,079, filed Jan. 7, 2009 and now U.S. Pat. No. 8,430,804, which is a non-provisional of U.S. Provisional Application No. 61/010,322, filed Jan. 7, 2008, U.S. Provisional Application No. 61/033,238, filed Mar. 3, 2008, U.S. Provisional Application No. 61/035,371, filed Mar. 10, 2008, and U.S. Provisional Application No. 61/047,693, filed Apr. 24, 2008, the specification(s) of which is/are incorporated herein in their entirety by reference.

This application is a continuation in-part and claims benefit of U.S. patent application Ser. No. 14/486,401, filed on Sep. 15, 2014, which is a non-provisional of U.S. Provisional Patent Application No. 61/877,765, filed Sep. 13, 2013, the specification(s) of which is/are incorporated herein in their entirety by reference.

U.S. patent application Ser. No. 14/486,401 is a continuation in-part of U.S. patent application Ser. No. 13/872,941, filed Apr. 29, 2013, which is a divisional of U.S. patent application Ser. No. 12/350,079, filed Jan. 7, 2009 and now U.S. Pat. No. 8,430,804, which is a non-provisional of U.S. Provisional Application No. 61/010,322, filed Jan. 7, 2008, U.S. Provisional Application No. 61/033,238, filed Mar. 3, 2008, U.S. Provisional Application No. 61/035,371, filed Mar. 10, 2008, and U.S. Provisional Application No. 61/047,693, filed Apr. 24, 2008, the specification(s) of which is/are incorporated herein in their entirety by reference.

U.S. patent application Ser. No. 14/486,401 is a continuation in-part of U.S. patent application Ser. No. 13/953,528, filed Jul. 29, 2013, which is a non-provisional of U.S. Provisional Application No. 61/676,783, filed Jul. 27, 2012, the specification(s) of which is/are incorporated herein in their entirety by reference.

U.S. patent application Ser. No. 14/486,401 is a continuation in-part of U.S. patent application Ser. No. 14/011,516, filed Aug. 27, 2013 and now U.S. Pat. No. 9,056,201, which is a continuation in-part of U.S. patent application Ser. No. 13/742,823, filed Jan. 16, 2013 and now U.S. Pat. No. 8,597,169, which is a continuation of U.S. patent application Ser. No. 12/497,644, filed Jul. 3, 2009, which is a continuation-in-part of U.S. patent application Ser. No. 12/350,079, filed Jan. 7, 2009 and now U.S. Pat. No. 8,430,804, which is a non-provisional of U.S. Provisional Application No. 61/010,322, filed Jan. 7, 2008, U.S. Provisional Application No. 61/033,238, filed Mar. 3, 2008, U.S. Provisional Application No. 61/035,371, filed Mar. 10, 2008, and U.S. Provisional Application No. 61/047,693, filed Apr. 24, 2008, the specification(s) of which is/are incorporated herein in their entirety by reference.

U.S. patent application Ser. No. 14/011,516 is a continuation in-part of U.S. patent application Ser. No. 13/872,941, filed Apr. 29, 2013, which is a divisional of U.S. patent application Ser. No. 12/350,079, filed Jan. 7, 2009 and now U.S. Pat. No. 8,430,804, which is a non-provisional of U.S. Provisional Application No. 61/010,322, filed Jan. 7, 2008, U.S. Provisional Application No. 61/033,238, filed Mar. 3, 2008, U.S. Provisional Application No. 61/035,371, filed Mar. 10, 2008, and U.S. Provisional Application No. 61/047,693, filed Apr. 24, 2008, the specification(s) of which is/are incorporated herein in their entirety by reference.

U.S. patent application Ser. No. 14/011,516 is a continuation in-part of U.S. patent application Ser. No. 13/111,780, filed May 19, 2011 and now U.S. Pat. No. 8,608,632, which is a non-provisional of U.S. Provisional Application No. 61/347,226, filed May 21, 2010; and a continuation-in-part of U.S. patent application Ser. No. 12/497,644, filed Jul. 3, 2009, which is a continuation-in-part of U.S. patent application Ser. No. 12/350,079, filed Jan. 7, 2009 and now U.S. Pat. No. 8,430,804, which is a non-provisional of U.S. Provisional Application No. 61/010,322, filed Jan. 7, 2008, U.S. Provisional Application No. 61/033,238, filed Mar. 3, 2008, U.S. Provisional Application No. 61/035,371, filed Mar. 10, 2008, and U.S. Provisional Application No. 61/047,693, filed Apr. 24, 2008, the specification(s) of which is/are incorporated herein in their entirety by reference.

U.S. patent application Ser. No. 14/011,516 is a continuation in-part of U.S. patent application Ser. No. 12/917,044, filed Nov. 1, 2010, which is a non-provisional of U.S. Provisional Application No. 61/257,232, filed Nov. 2, 2009 and U.S. Provisional Application No. 61/376,115, filed Aug. 23, 2010, the specification(s) of which is/are incorporated herein in their entirety by reference.

U.S. patent application Ser. No. 14/011,516 is a continuation in-part of U.S. patent application Ser. No. 13/111,765, filed May 19, 2011 and now U.S. Pat. No. 8,602,959, which is a non-provisional of U.S. Provisional Application No. 61/347,233, filed May 21, 2010, the specification(s) of which is/are incorporated herein in their entirety by reference.

U.S. patent application Ser. No. 14/011,516 is a continuation in-part of U.S. patent application Ser. No. 13/953,528, filed Jul. 29, 2013, which is a non-provisional of U.S. Provisional Application No. 61/676,783, filed Jul. 27, 2012, the specification(s) of which is/are incorporated herein in their entirety by reference.

FIELD OF THE INVENTION

The present invention is directed to minimally-invasive methods and devices and dosimetry for introducing radiation to the eye for treating and/or managing eye conditions including but not limited to macula degeneration.

BACKGROUND OF THE INVENTION

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, and glaucoma are several examples.

Age related macular degeneration (ARMD) is the leading cause of blindness in the elderly. ARMD attacks the center region of the retina (i.e., macula), responsible for detailed vision and damages it, making reading, driving, recognizing faces and other detailed tasks difficult or impossible. Current estimates reveal that approximately forty percent of the population over age 75, and approximately twenty percent of the population over age 60, suffer from some degree of macular degeneration. "Wet" or exudative ARMD is the type of ARMD that most often causes blindness. In wet ARMD, newly formed choroidal blood vessels (choroidal neovascularization (CNV)) leak fluid and cause progressive damage to the retina. About 200,000 new cases of Wet ARMD occur each year in the United States alone.

Brachytherapy is treatment of a region by placing radioactive isotopes in, on, or near it. Both malignant and benign conditions are successfully treated with brachytherapy. Lesion location dictates treatment technique. For the treatment of tumors or tumor beds in the breast, tongue, abdomen, or muscle capsules, catheters are inserted into the tissue (interstitial application). Radiation may be delivered by inserting strands of radioactive seeds into these catheters for a predetermined amount of time. Permanent implants are also possible. For example, in the treatment of prostate cancer, radioactive seeds are placed directly into the prostate where they remain indefinitely. Restenosis of coronary arteries after stent implantation, a non-malignant condition, has been successfully treated by placing a catheter into the coronary artery, then inserting a radioactive source into the catheter and holding it there for a predetermined time in order to deliver a sufficient dose to the vessel wall. Beta emitters, such as phosphorus 32 (P-32) and strontium 90 (Sr-90), and gamma emitters, such as iridium 192 (Ir-192), have been used. The Collaborative Ocular Melanoma Study (COMS), a multicenter randomized trial sponsored by the National Eye Institute and the National Cancer Institute demonstrated the utility of brachytherapy for the treatment of ocular cancers and/or tumors. The technique employs an invasive surgical procedure to allow placement of a surface applicator (called an episcleral plaque) that is applied extraocullarly by suturing it to the sclera. The gold plaque contains an inner mold into which radioactive iodine 125 (I-125) seeds are inserted. The gold plaque serves to shield the tissues external to the eye while exposing the sclera, choroid, choroidal melanoma, and overlying retina to radiation. The plaque remains fixed for a few days to one week in order to deliver approximately 85 Gy to the tumor apex.

Radiotherapy has long been used to treat arteriovenous malformations (AVM), a benign condition involving pathological vessel formation, in the brain. An AVM is a congenital vascular pathology characterized by tangles of veins and arteries. The dose applicable to the treatment of neovascularization in age-related macular degeneration (WAMD) by the devices described herein may be based on stereotactic radiosurgery (SRS) treatment of arteriovenous malformations (AVM). SRS is used to deliver radiation to the AVM in order to obliterate it, and radiation is highly effective for AVM treatment. The minimum dose needed to obliterate an AVM with high probability is approximately 20 Gy. However, small AVMs (<1 cm) are often treated with a higher dose (e.g., 30 Gy) because when treating small AVMs, a significant amount of eloquent brain (e.g., brain regions wherein injury typically causes disabling neurological deficits) is not exposed to the high dose of radiation. The reported SRS doses correspond to the dose received at the periphery of the AVM, while the dose at the nidus (center) may be up to a factor of 2.5 times greater than the reported SRS dose.

The vascular region involved in WAMD is much smaller than even the smallest AVM, thus the effective doses are expected to be similar to the highest doses used for AVM. Studies of irradiation of WAMD have shown that greater than 20 Gy are required, although one study indicates some response at 16 Gy. Without wishing to limit the present invention to any theory or mechanism, the devices described herein for WAMD are expected to be effective by delivering a nearly uniform dose to the entire region of neovascularization or by delivering a nonuniform dose which may vary by a factor of 2.5 higher in the center as compared to the boundary of the region with minimum doses of 20 Gy and maximum doses of 75 Gy. A report using radiosurgery for macular degeneration describes that a dose of only 10 Gy was not effective (Haas et al, J Neurosurgery 93, 172-76, 2000). In that study, the stated dose is the peripheral dose with the center being about 10% greater. Furthermore, the study results were severely plagued by retinal complications.

Without wishing to limit the present invention to any theory or mechanism, it is believed that the devices of the present invention are advantageous over the prior art. For example, since SRS employs external photon beams which easily penetrate the ocular structures and pass through the entire brain, the patient must be positioned such that the beams may be directed towards the macula, making the geometric uncertainties of delivery a few millimeters. The devices of the present invention have geometric and dosimetric advantages because they may be placed at the macula with submillimeter accuracy, and the beta radioisotope may be used to construct the radiation source with predominately limited range.

The present invention features methods and devices for minimally-invasive delivery of radiation to the posterior portion of the eye.

SUMMARY OF THE INVENTION

The present invention features cannulas for delivering radiation to a target. In some embodiments, the cannulas are for placing under the Tenon's capsule. For example, the present invention features a cannula (e.g., a fixed shape cannula) comprising a distal portion for placement around a portion of a globe of an eye; wherein the distal portion has a radius of curvature between about 9 to 15 mm and an arc length between about 25 to 35 mm; a curved proximal portion having a radius of curvature between about an inner cross-sectional radius of the cannula and about 250 mm; an inflection point which is where the distal portion and the proximal portions connect with each other; and a handle extending from the proximal portion, the handle lies on an axis such that the axis does not intersect with the distal portion. In some embodiments, the angle $\theta_1$ between (i) a line $l_3$ tangent to the inflection point between the distal portion and the proximal portion and (ii) the proximal portion is between greater than about 0 degrees to about 180 degrees.

In some embodiments, at least a portion of the cannula is hollow. In some embodiments, at least a portion of the cannula is solid. In some embodiments, the distal portion and proximal portion are both solid.

In some embodiments, the distal portion has a radius of curvature of about 12 mm and the distal portion has an arc length of about 30 mm.

In some embodiments, the cannula further comprises a radionuclide brachytherapy source (RBS), e.g., an RBS disposed at a tip of the distal portion. In some embodiments, the tip of the distal portion has a diameter or width that is greater than that of the distal portion. In some embodiments, the handle comprises a radiation shielding pig for shielding a radionuclide brachytherapy source (RBS).

In some embodiments, the cannula has an outer cross sectional shape that is round or oval.

In some embodiments, at least a portion of the cannula is hollow, and the cannula has an internal cross sectional shape that is configured to allow a radionuclide brachytherapy source (RBS) to glide through. In some embodiments, at least a portion of the cannula is hollow, and the cannula has an internal cross sectional shape that is round or oval.

In some embodiments, an advancing mechanism is disposed in the cannula for advancing a radionuclide brachytherapy source (RBS) from a starting position in the cannula to at or near a tip of the distal portion of the cannula. In some embodiments, the advancing mechanism is selected from the group consisting of a guide wire, a non-wire plunger, an air pressure mechanism, a vacuum mechanism, a hydrostatic pressure mechanism employing a fluid, or a combination thereof.

In some embodiments, the cannula further comprises a protuberance disposed on the distal portion.

The present invention also features a cannula with a fixed shape, wherein the cannula comprises a distal portion for placement around a portion of a globe of an eye; a proximal portion connected to the distal portion via an inflection point; and a handle extending from the proximal portion, the handle lies on an axis such that the axis does not intersect with the distal portion. In some embodiments, the distal portion has a shape of an arc formed from a connection between two points located on an ellipsoid, the ellipsoid having an x-axis dimension "a", a y-axis dimension "b," and a z-axis dimension "c," wherein "a" is between about 0 to 1 meter, "b" is between about 0 to 1 meter, and "c" is between about 0 to 1 meter. In some embodiments, the proximal portion has a shape of an arc formed from a connection between two points on an ellipsoid, the ellipsoid having an x-axis dimension "d", a y-axis dimension "e," and a z-axis dimension "f," wherein "d" is between about 0 to 1 meter, "e" is between about 0 to 1 meter, and "f" is between about 0 to 1 meter. In some embodiments, the angle $\theta_1$ between (i) a line $l_3$ tangent to the inflection point between the distal portion and the proximal portion and (ii) the proximal portion is between greater than about 0 degrees to about 180 degrees.

In some embodiments, "a" is between about 0 to 50 mm, "b" is between about 0 and 50 mm, and "c" is between about 0 and 50 mm. In some embodiments, "d" is between about 0 to 50 mm, "e" is between about 0 and 50 mm, and "f" is between about 0 and 50 mm. In some embodiments, the inflection point creates a soft bend between the distal portion and the proximal portion. In some embodiments, the distal portion has an arc length of between about 25 to 35 mm. In some embodiments, the proximal portion has an arc length of between about 10 to 75 mm.

The present invention also features methods and devices for applying radiation (e.g., beta radiation) for the treatment of diseases including but not limited to wet age-related macular degeneration. The cannula size is small, which allows for minimally-invasive surgery by making a small incision in the conjunctiva and inserting the cannula under Tenon's membrane along the sclera. No dissection or manipulation of the globe is necessary. In some cases, the tip of the device may be held against the sclera, which may help to control the deposition of the radiation dose (e.g., to within a fraction of a millimeter).

In some embodiments, the devices and methods of the present invention deliver radiation to the episcleral surface. In some embodiments, the radiation source is used within a disposable applicator. In some embodiments, the dose is 24 Gy and is given to the target (e.g., wet AMD lesion) over the course of 5 to 7 minutes, depending on the source strength, e.g., 555 to 740 MBq (15-20 mCi). The present invention also features methods of determining the dose delivered to the lesion and nearby normal tissues.

The present invention features a brachytherapy devices for delivery of radiation. In some embodiments, the device comprises a curved cannula divided into a distal portion and a proximal portion, wherein the distal portion is for placement around a portion of a globe of an eye. In some embodiments, the distal portion has a radius of curvature between about 9 to 15 mm and an arc length between about 25 to 35 mm. The device may further comprise a radionuclide brachytherapy source (RBS). In some embodiments, the device comprises a shield compartment for temporarily housing the RBS. In some embodiments, the shield compartment is connected to or part of the distal portion of the cannula. In some embodiments, the shield compartment is part of or connected to the proximal portion of the cannula. In some embodiments, the RBS can be advanced to a tip region of the distal portion of the cannula. In some embodiments, the RBS is fixed in a place in the cannula. For example, in some embodiments, the RBS is disposed in the tip of the cannula (e.g., the tip of the distal portion of the cannula.

In some embodiments, the RBS is encapsulated. In some embodiments, the RBS is encapsulated in stainless steel. In some embodiments, the RBS comprises four enamel beads, each bead is impregnated with Sr-90. In some embodiments, each bead is about 0.5 mm in diameter. In some embodiments, the RBS comprises Sr-90. In some embodiments, the RBS can deliver a dose of about 24 Gy to a target.

The present invention also features a method of irradiating a target of an eye in a patient, said method comprising inserting a cannula into a potential space under a Tenon's capsule of the eye of the patient, the cannula having a radionuclide brachytherapy source (RBS) at a treatment position, wherein the RBS is positioned over the target and the RBS irradiates the target.

The present invention also features a method of irradiating a target of an eye in a patient. The method comprises inserting a cannula into a potential space under the Tenon's capsule. The cannula comprises a radionuclide brachytherapy source (RBS) at a treatment position, whereby the RBS is positioned over the target as shown, for example, in FIG. 5. The RBS irradiates the target. In some embodiments, the treatment position is a location on or within the cannula (e.g., the middle of the cannula, along the length or a portion of the length of the cannula, near the end of the cannula). In some embodiments, the treatment position comprises a window on the cannula. In some embodiments, the treatment position is configured to receive an RBS. In some embodiments, an indentation tip and/or a light source is disposed at the treatment position.

In some embodiments, the Tenon's capsule guides the insertion of the cannula and provides positioning support for the cannula. In some embodiments, the target is a lesion associated with the retina. In some embodiments, the target is located on the vitreous side of the eye. In some embodiments, the target (e.g., lesion) is a benign growth or a malignant growth.

In some embodiments, method comprises inserting a cannula between the Tenon's capsule and the sclera of the eye, for example at the limbus, a point posterior to the limbus of the eye, a point between the limbus and the fornix. In some embodiments, any appropriate cannula may be used in accordance with the present invention for the subtenon procedure. In some embodiments, cannulas that may be used in accordance with the present invention include flexible cannulas, fixed shape cannulas (or a combination of a flexible and fixed shape cannula), and cannulas which are tapered to provide a larger circumferential surface in the portion of the cannula which remains in the Tenon's capsule upon insertion, thereby providing additional positioning support to maintain the cannula over the target. In some embodiments, the arc length of the distal portion of the cannula is suitably of sufficient length to penetrate the Tenon's capsule and extend around the outside of the globe of the eye to a distal end position in close proximity to the macular target.

In some embodiments, the cannula employed in the inventive subtenon procedure comprises a distal portion, which is a portion of the cannula that is placed around a portion of the globe of the eye. The cannula has a radionuclide brachytherapy source ("RBS") at a treatment position (e.g., in the middle of the cannula, near the end, in the middle, along the length of the cannula). The cannula may be "preloaded" with an RBS or "afterloaded". For example, in some embodiments, the RBS is loaded into the cannula before the cannula is inserted. For example, in U.S. Pat. No. 7,070,554 to White, the brachytherapy device comprises a "preloaded" radiation source, i.e., a radiation source affixed at the tip of the device prior to the insertion of the device into the eye. In some embodiments, the RBS is loaded into the cannula after the cannula is inserted. For example, see FIG. 6, where the radiation source is loaded to near the tip after the cannula has been inserted into the eye. Also, for example, see FIGS. 1C and 1D where the radiation source is advanced from the handle/pig after positioning the distal portion. The method further comprises positioning the RBS over the sclera portion that corresponds with the target (e.g., lesion), and the RBS irradiates the target (e.g., lesion) through the sclera.

The cannula may be of various shapes and sizes and constructed from a variety of materials. In some embodiments, the cannula is a fixed shape cannula. In some embodiments, the cannula is a flexible cannula, including an endoscope-like device. In some embodiments, the cannula is tapered (e.g., a larger circumferential area in the portion which remains in the Tenon's capsule upon insertion.

In some embodiments, the target is a lesion associated with the retina. In some embodiments, the target (e.g., lesion) is a neovascular lesion.

Neovascular lesions of wet macula degeneration generally cannot be seen via indirect/direct ophthalmoscopy. In some embodiments, an angiogram (or other localizing technology such as optical coherence tomography, ultrasound) is performed, for example before the cannula is inserted between the Tenon's capsule and sclera. The angiogram may help locate the cannula and the target (e.g., lesion), and direct the cannula to the correct position over the target. For example, while localizing the target (e.g., lesion) via the surrounding landmarks and in reference to the previously obtained angiogram, the cannula may be directed to a precise position. In some embodiments, the cannula comprises a window and/or an orifice, and the window/orifice of the cannula can be placed directly behind the target (e.g., lesion). In some embodiments, a photograph or video may be taken during the procedure to document the placement of the cannula.

In some embodiments, an angiogram, optical coherence tomography, ultrasound, or other localizing technology is performed, for example after the cannula is inserted between the Tenon's capsule and sclera. The localizing technology (e.g., angiogram) may help locate the cannula and the target (e.g., lesion), and direct the cannula to the correct position over the target. For example, while visualizing the target (e.g., lesion) via the localizing technology (e.g., angiogram), the cannula may be directed to a precise position. In some embodiments, the cannula comprises a window and/or an orifice, and the window/orifice of the cannula can be placed directly behind the target (e.g., lesion). In some embodiments, the localizing technology (e.g., angiogram) is a real-time procedure. In some embodiments, localizing technology is optical coherence tomography or ultrasound or other technology. In some embodiments, a photograph or video may be taken during the procedure to document the placement of the cannula.

The RBS can be constructed to provide any dose rate to the target. In some embodiments, the RBS provides a dose rate of between about 0.1 to 1 Gy/min, between about 1 to 10 Gy/min, between about 10 to 20 Gy/min, between about 20 to 30 Gy/min, between about 30 to 40 Gy/min, between about 40 to 50 Gy/min, between about 50 to 60 Gy/min, between about 60 to 70 Gy/min, between about 70 to 80 Gy/min, between about 80 to 90 Gy/min, between about 90 to 100 Gy/min, or greater than 100 Gy/min to the target (e.g., lesion).

The present invention also features a method of irradiating a target (e.g., lesion associated with the retina) of an eye in a patient. The method comprises inserting a cannula into the potential space under the Tenon's capsule (e.g., between the Tenon's capsule and the sclera) of the eye. In some embodiments, the cannula is inserted at the limbus, a point posterior to the limbus, or a point between the limbus and the fornix. In some embodiments, the cannula comprises a distal portion (e.g., a portion of the cannula that is placed over a portion of the globe of the eye). In some embodiments, the distal portion of the cannula is placed on or near the sclera behind the target (e.g., a lesion on the retina). A radionuclide brachytherapy source (RBS) is advanced through the cannula, for example to the treatment position (e.g., in the middle of the cannula, near a tip/end of distal portion), via a means for advancing the RBS. (In some embodiments, the means for advancing the RBS comprises a guide wire. In some embodiments, the means for advancing the RBS comprises a ribbon). The target is exposed to the RBS. The RBS may be loaded before the cannula is inserted or after the cannula is inserted.

The cannula may be constructed in various shapes and sizes. In some embodiments, the distal portion is designed for placement around a portion of the globe of the eye. In some embodiments, the distal portion has a radius of curvature between about 9 to 15 mm and an arc length between about 25 to 35 mm. In some embodiments, the cannula further comprises a proximal portion having a radius of curvature between about the inner cross-sectional radius of the cannula and about 1 meter. In some embodiments, the cannula further comprises an inflection point, which is where the distal portion and the proximal portions connect with each other. In some embodiments, the angle $\theta_1$ between the line $l_3$ tangent to the globe of the eye at the inflection point and the proximal portion is between greater than about 0 degrees to about 180 degrees.

The present invention also features a hollow cannula with a fixed shape. The cannula comprises a distal portion for placement around a portion of the globe of an eye, wherein the distal portion has a radius of curvature between about 9 to 15 mm and an arc length between about 25 to 35 mm. The cannula further comprises a proximal portion having a radius of curvature between about the inner cross-sectional radius of the cannula and about 1 meter. The cannula further comprises an inflection point, which is where the distal portion and the proximal portions connect with each other. In some embodiments, the angle $\theta_1$ between the line $l_3$ tangent to the globe of the eye at the inflection point and the proximal portion is between greater than about 0 degrees to about 180 degrees.

In some embodiments, once the distal end of the distal portion is positioned within the vicinity of the target, the proximal portion is curved away from the visual axis as to allow a user to have direct visual access in the eye.

The present invention also features a cannula with a fixed shape. The cannula comprises a distal portion for placement around a portion of a globe of an eye and a proximal portion connected to the distal portion via an inflection point. In some embodiments, the distal portion has a shape of an arc formed from a connection between two points located on an ellipsoid, wherein the ellipsoid has an x-axis dimension "a", a y-axis dimension "b," and a z-axis dimension "c." In some embodiments, "a" is between about 0 to 1 meter, "b" is between about 0 to 1 meter, and "c" is between about 0 to 1 meter. In some embodiments, the proximal portion has a shape of an arc formed from a connection between two points on an ellipsoid, wherein the ellipsoid has an x-axis dimension "d", a y-axis dimension "e," and a z-axis dimension "f." In some embodiments, "d" is between about 0 to 1 meter, "e" is between about 0 to 1 meter, and "f" is between about 0 to 1 meter. In some embodiments, the angle $\theta_1$ between the line $l_3$ tangent to the globe of the eye at the inflection point and the proximal portion is between greater than about 0 degrees to about 180 degrees.

The present invention further features a "fine positioning" surgical technique. For example, after inserting a cannula into a potential space under a Tenon's capsule of the eye of the patient, the surgeon observes the position of (through the patient's pupil via a "visual axis", see for example FIG. 5) the treatment position of the cannula in a posterior pole of the eye, and adjust it accordingly to accurately localize it over the target as shown in FIG. 5. In some embodiments, the physician observes the position of the treatment position and adjusts it while the patient's eye is in a primary gaze position. A primary gaze position is when the patient looks straight ahead. In some embodiments, the physician observes the position of the treatment position and adjusts it while the patient's eye is in any one of the following position: elevated, depressed, adducted, elevated and adducted, elevated and abducted, depressed and adducted, and depressed and abducted. By seeing the position of the treatment position, the surgeon can adjust the cannula to position the treatment position over a target, as shown for example in FIG. 5. In some embodiments, one of the advantages of the present "fine positioning" technique is that it allows for convenient and accurate placement of the RBS at the appropriate location behind the eye. In some embodiments, the fine positioning technique allows for placement of the cannula with millimetric precision.

In some embodiments, the inventive methods of the present invention can be performed under general or local anesthesia (e.g., retro- or peribulbar) to the eye. When a general or local anesthesia is administered to the patient's eye, the eye will be in a primary position, and the patient has no motor movement of the eye. Accordingly, after the general or local anesthesia, the patient's eye will be in a primary gaze position, i.e., looking straight forward. The present inventive surgical methods and device allow for the surgeon to administer the radiation accurately to the target in the eye while the eye is in a primary gaze position. In some embodiments, the advantage of being able to perform the treatment while the patient's eye is in a primary gaze position is that it does not require the surgeon to perform additional surgical steps to secure the eye to a non-primary gaze position, as such securing steps may traumatize the eye.

The present invention also features a method of delivering radiation to an eye. The method comprises irradiating a target (e.g., a lesion associated with the retina, a target on the vitreous side of the eye, a benign growth, a malignant growth) from an outer surface of the sclera. In some embodiments, the target receives a dose rate of greater than about 10 Gy/min.

The present invention also features a method of irradiating a target (e.g., a target/lesion associated with the retina) of an eye in a patient. The method comprises placing a radionuclide brachytherapy source (RBS) at or near a portion of the eye (e.g., sclera) that corresponds with the target. The RBS irradiates the target through the sclera, wherein more than 1% of the radiation from the RBS is deposited on a tissue at or beyond a distance of 1 cm from the RBS. In some embodiments, about 1% to 15% of the radiation from the RBS is deposited on a tissue or beyond a distance of 1 cm from the RBS. In some embodiments, about less than 99% of the radiation from the RBS is deposited on a tissue at a distance less than 1 cm from the RBS.

The methods of the present invention also allow for delivering a smaller volume/area of radiation as compared to other procedures. For example, a radionuclide brachytherapy source ("RBS") in the shape of a disk can provide a controlled projection of radiation (e.g., a therapeutic dose) onto the target, while allowing for the radiation dose to fall off quickly at the periphery of the target. This keeps the radiation within a limited area/volume and may help prevent unwanted exposure of structures such as the optic nerve and/or the lens to radiation. Without wishing to limit the present invention to any theory or mechanism, it is believed that low areas/volumes of irradiation enables the use of higher dose rates, which in turn allows for faster surgery time and less complications.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 1A-1B shows views of various fixed shape cannula 100 according to the present invention. FIG. 1A shows a side view of a fixed shape cannula 100 comprising a distal portion 110, a proximal portion 120, an inflection point 130, and a handle 140. Also shown is a tip 200, the arc length 185 of the distal portion 110, and the arc length 195 of the proximal portion 120. FIG. 1B shows a perspective view of the fixed shape cannula 100 from FIG. 1A. FIG. 1C shows the distal region 112 of the distal portion 110, the middle region 113 of the distal portion, a window 510, a seed-shaped RBS 400, and a guide wire 350 having a distal end 320 wherein the wire 350 is housed in the handle 140 of the fixed shape cannula 100. FIG. 1D shows the guide wire 350 extended through the proximal portion 120 and the distal portion 110 of the fixed shape cannula 100. FIG. 1F shows the circle 191 defined by the curvature of the proximal portion 120, the radius 192 of circle 191, and the radius of curvature 190 of the proximal portion 120.

Figure 1E:
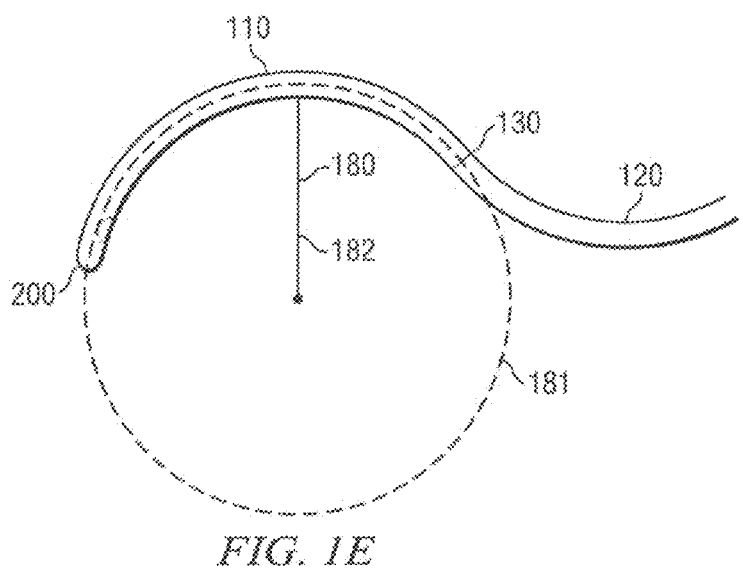
FIG. 1E shows the circle 181 defined by the curvature of the distal portion 110, the radius 182 of circle 181, and the radius of curvature 180 of the distal portion 110.

FIG. 2A-2M shows side views of various tips 200 of distal portions 110 according to the present invention. Various tips 200 may comprise an orifice 500 or a window 510 and/or a light source 610, and/or an indentation tip 600. FIG. 2J illustrates a memory wire 300 wherein the memory wire 300 forms a flat spiral 310 when extended from the tip 200. FIG. 2K shows a distal chamber 210 wherein a memory wire 300 forms a flat spiral 310 when extended into the distal chamber 210.

FIG. 3 shows a side view of a distal portion 110 and a proximal portion 120 according to the present invention.

FIG. 4A-4D shows perspective views of handles 140 according to the present invention. FIG. 4A shows a handle 140 comprising a thumb ring 810, wherein the handle comprises a non-wire plunger 800. FIG. 4B shows a handle 140 comprising a graduated dial 820. FIG. 4C shows a handle 140 comprising a slider 830. FIG. 4D shows an example of a fixed shape cannula comprising a radiation shielding pig 900 between the proximal portion 120 and the handle 140. A seed-shaped RBS 400 is attached to a guide wire 350, and the seed-shaped RBS 400 is housed within the pig 900.

Figure 5:
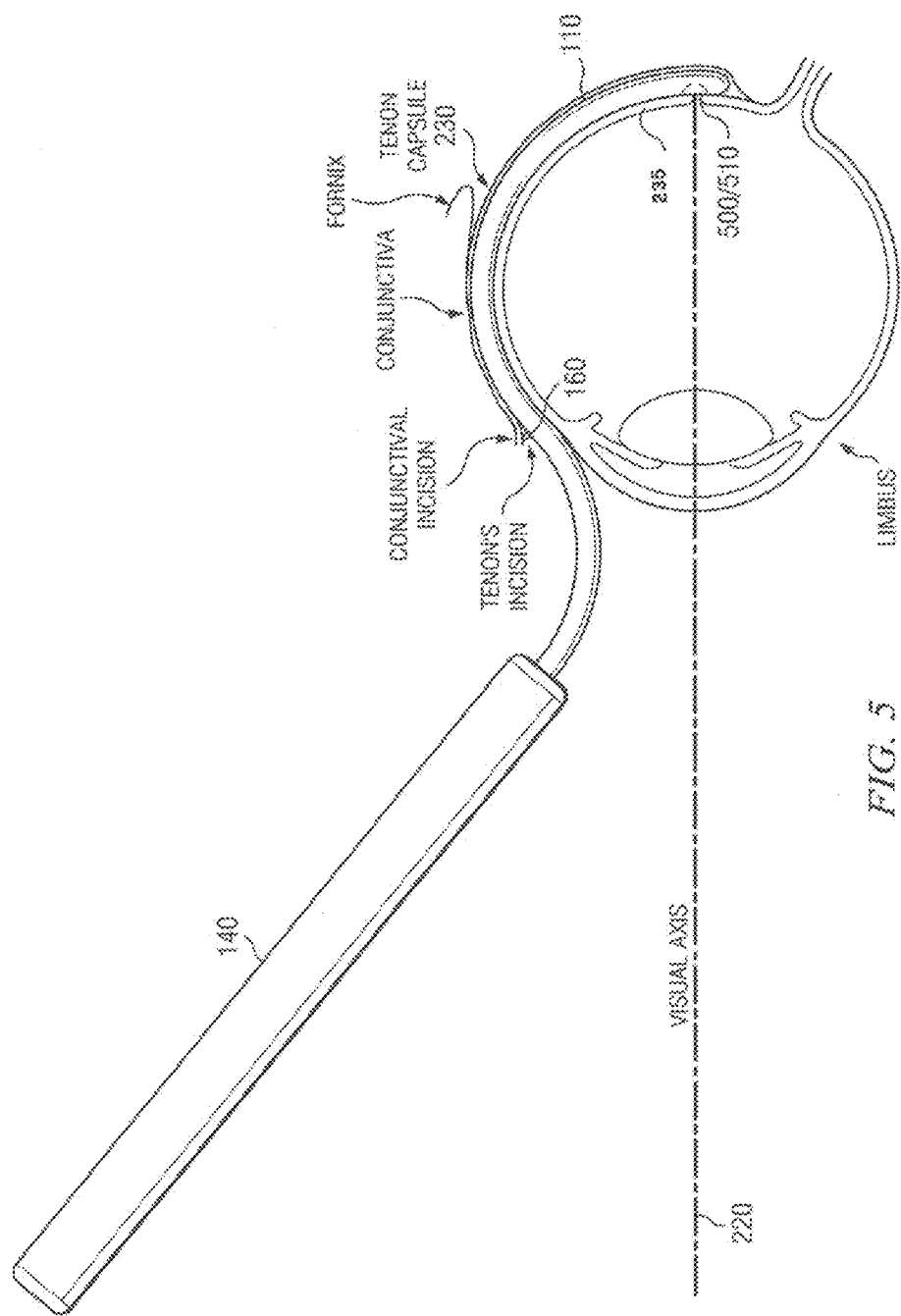

FIG. 5 shows the insertion of an assembled fixed shape cannula 100 according to the present invention. The fixed shape cannula 100 comprises a locator 160. The handle 140 and proximal portion 120 are out of the visual axis 220 of the physician and the patient. Tenon's capsule a layer of tissue running from the limbus anteriorly to the optic nerve posteriorly. The Tenon's capsule is surrounded anteriorly by the bulbar conjunctiva that originates at the limbus and reflects posteriorly into the tarsal conjunctiva at the conjunctival fornix.

FIG. 6A-6B shows the insertion of an unassembled fixed shape cannula 100 according to the present invention, wherein the handle 140 and/or radiation shielding pig 900 is attached to the proximal portion 120 via a connector 150 after the fixed shape cannula 100 is in place.

Figure 7:
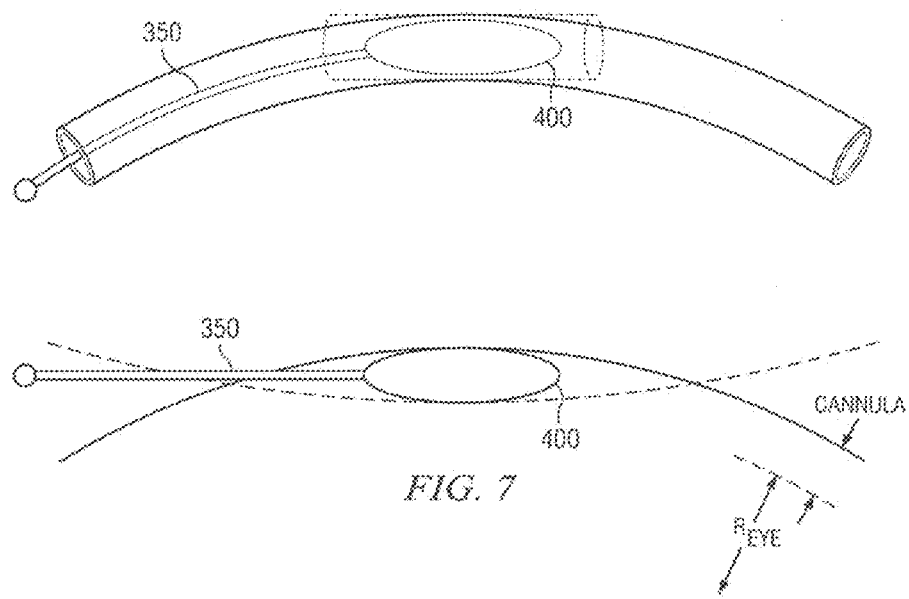

FIG. 7 shows an example of a radionuclide brachytherapy source ("RBS") (e.g., seed-shaped RBS 400) inserted into a fixed shape cannula.

Figure 8:
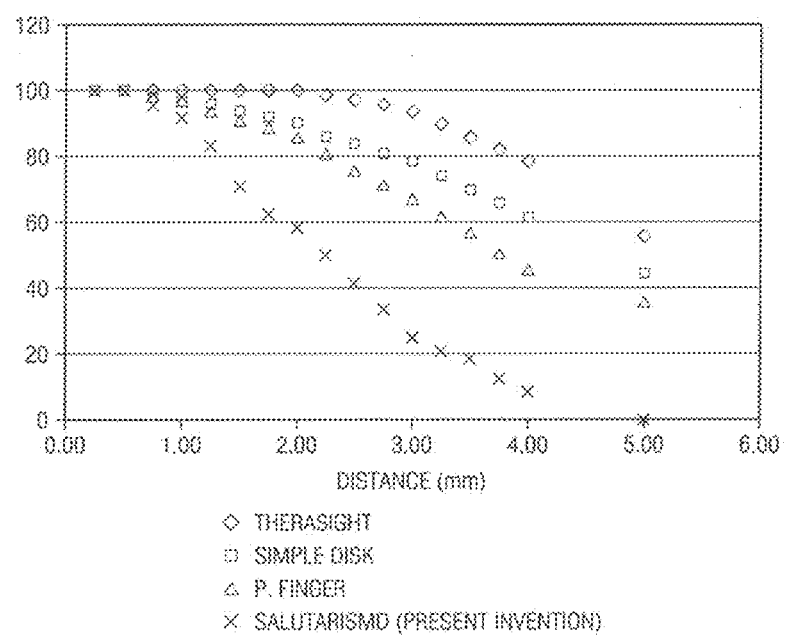

FIG. 8 shows lateral radiation dose profile of various devices, including that of the present device (SalutarisMD). The graph represents an example of relative radiation doses (y-axis) measured at distances from the center of the target (x-axis). The SalutarisMD device presents a more rapid decline in radiation dose as the distance away from the target periphery (e.g., area within about 1 mm from center of target) increases.

Figure 9:
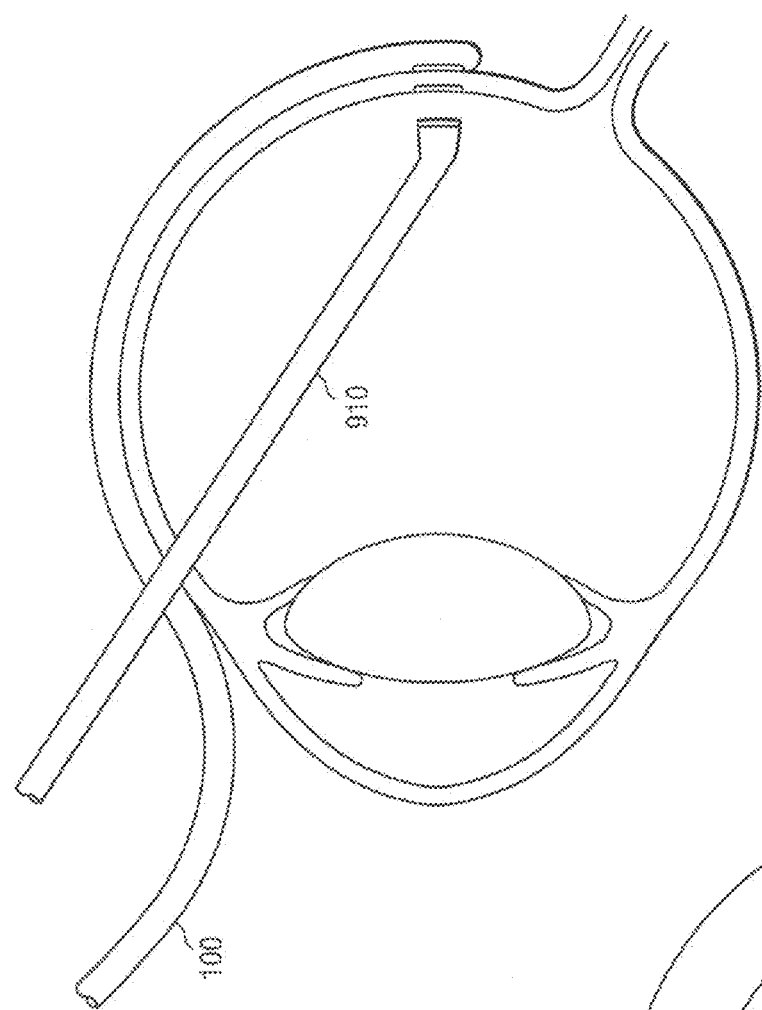

FIG. 9 shows a comparison of the insertion of a fixed shape cannula 100 of the present invention (e.g., according to a posterior radiation approach) to the insertion of a device used for an intravitreal radiation approach 910.

Figure 10:
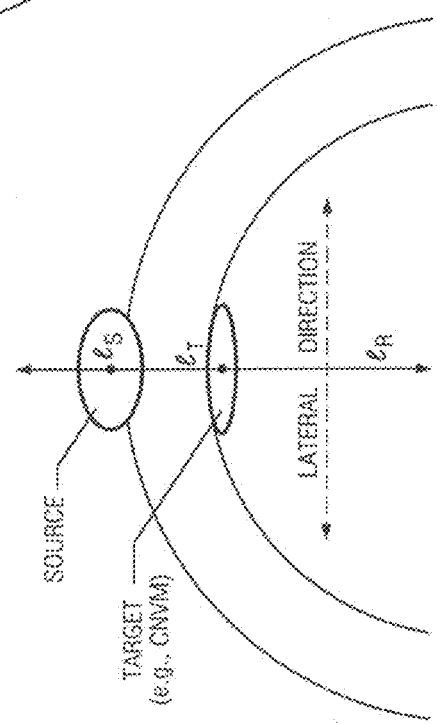

FIG. 10 is an illustration defining the term "lateral." The drawing may be representative of a horizontal cross-section of an eye ball, wherein the target is the choroidal neovascular membrane (CNVM), the source is the radioactive source (e.g., seed-shaped RBS 400), and the sclera is located between the source and the target.

Figure 11:
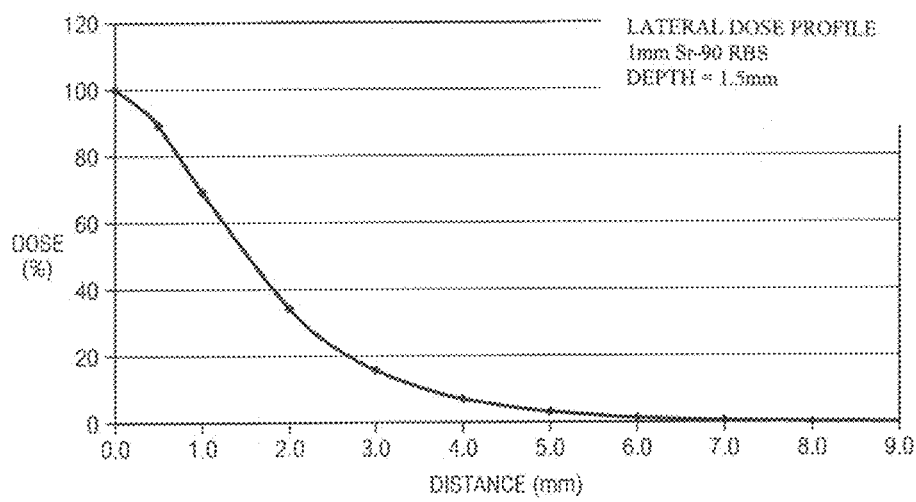

FIG. 11 shows an example of a radiation dose profile of a 1 mm Sr-90 source as measured laterally at a 1.5 mm depth.

Figure 12:
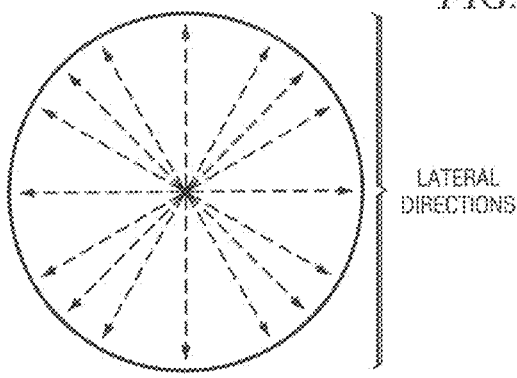

FIG. 12 shows an example of lines that are perpendicular to line $l_R$ as viewed looking above the RBS/target downward along line $l_R$.

Figure 13:
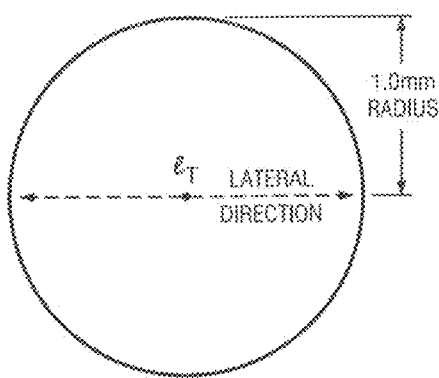

FIG. 13 shows an example of an isodose (e.g., the area directly surrounding the center of the target wherein the radiation dose is substantially uniform), perpendicular to line $l_R$, as viewed looking above the RBS/target downward along line $l_R$. In this example, the area wherein the radiation dose is substantially uniform extends up to about 1.0 mm away from the center of the target.

Figure 14A:
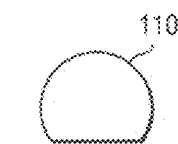
Figure 14B:
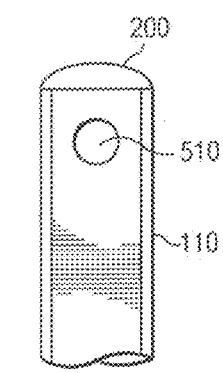
Figure 14C:
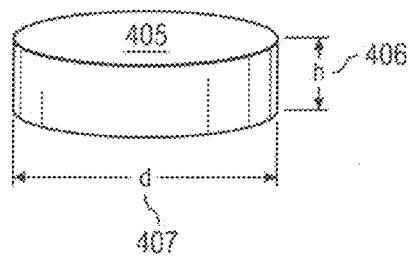
Figure 14D:
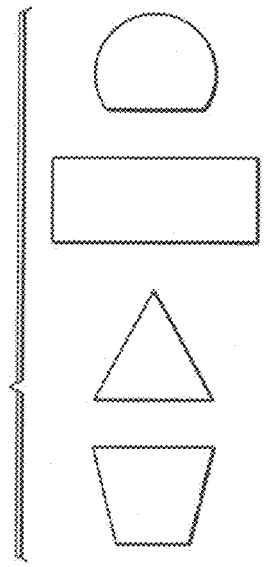
Figure 14E:
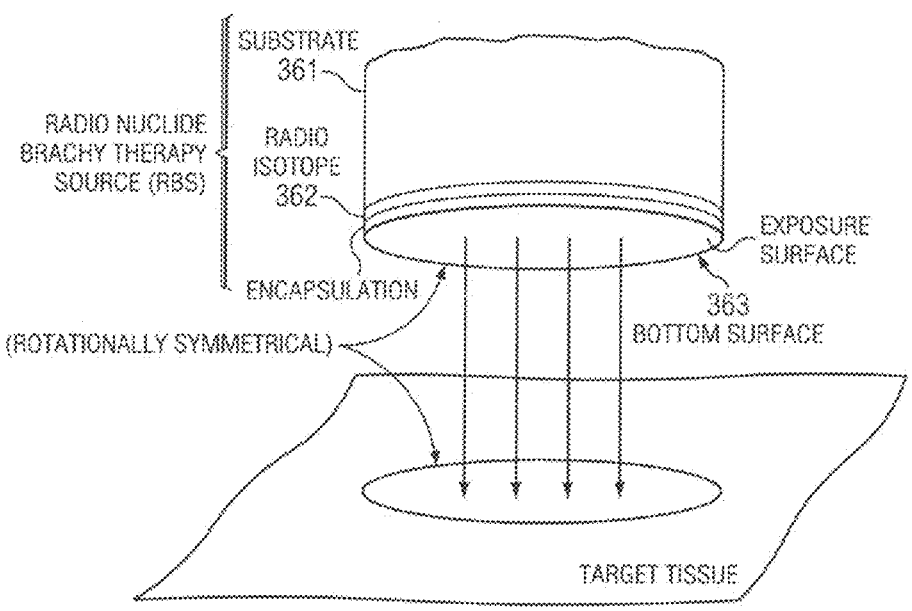
Figure 14F:
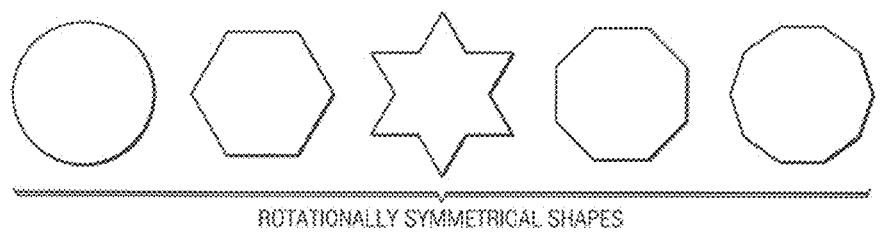
Figure 14G:
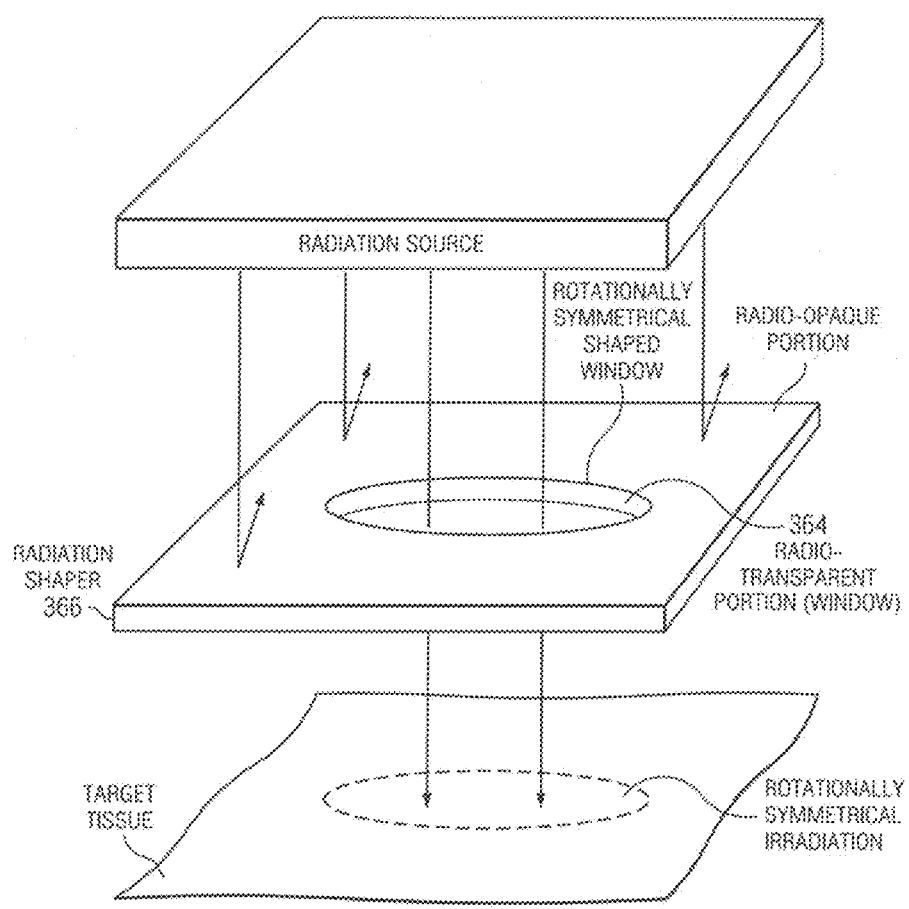

FIG. 14A is a front cross sectional view of the distal portion 110 of the fixed shape cannula 100 wherein the top of the fixed shape cannula 100 (e.g., distal portion 110) is rounded and the bottom is flat. FIG. 14B is a bottom view of the distal portion 110 of FIG. 14A. FIG. 14C is a perspective view of an example of the RBS in the form of a disk 405 having a height "h" 406 and a diameter "d" 407. FIG. 14D shows a variety of side cross sectional views of RBSs having various shapes (e.g, rectangle, triangle, trapezoid). FIG. 14E shows an example of a RBS comprising a disk-shaped substrate 361. On the bottom surface 363 of the substrate 361 is an isotope 362. FIG. 14F shows examples of rotationally symmetrical shapes. The present invention is not limited to the shapes shown in FIG. 14F. FIG. 14G shows an example of a radiation shaper 366 comprising a window 364 (e.g., rotationally symmetrically-shaped window). The window 364 is generally radio-transparent and the radiation shaper 366 is generally radio-opaque. Radiation from a RBS is substantially blocked or attenuated by the radiation shaper 366 but not the window 364.

FIG. 15 shows an example of an ellipsoid 450 with an x-axis dimension, a y-axis dimension, and a z-axis dimension.

FIG. 16A shows a side view of the proximal portion 120 of the fixed shape cannula 100. FIG. 16B-D shows examples of inner diameters 171, outer diameters 172, and an inner radius 173 of a cross-section of the proximal portion 120 of the fixed shape cannula 100.

Figure 17:
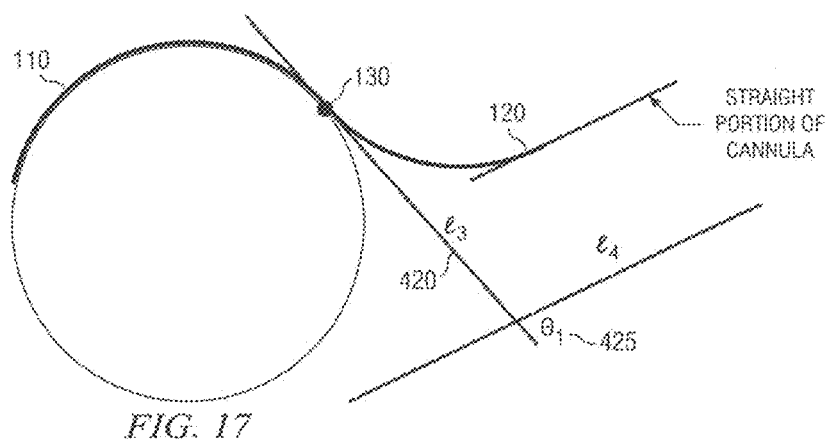

FIG. 17 shows an example of angle $\theta_1$ 425 which is between line $l_3$ 420 tangent to the globe of the eye at the inflection point 130 and the proximal portion 120.

Figure 18A:
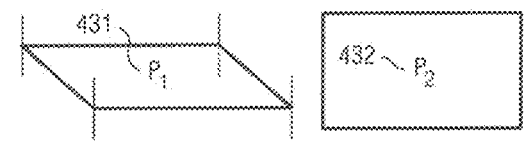
Figure 18B:
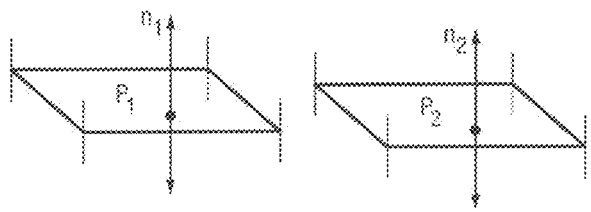
Figure 18C:
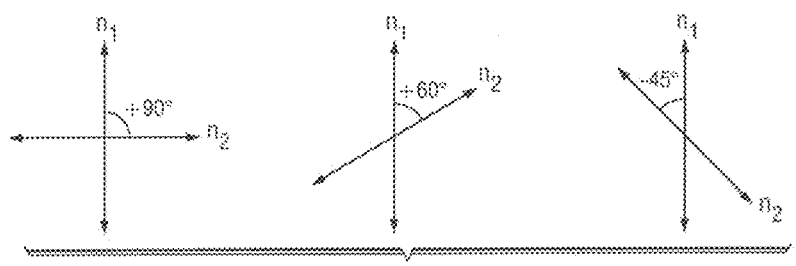

FIG. 18A shows two different planes $P_1$ 431 and $P_2$ 432. FIG. 18B shows plane $P_1$ 431 as defined by the normal to the plane $n_1$ and plane $P_2$ 432 defined by the normal to the plane $n_2$. FIG. 18C shows examples of angles between $P_1$ 431 and $P_2$ 432.

Figure 19A:
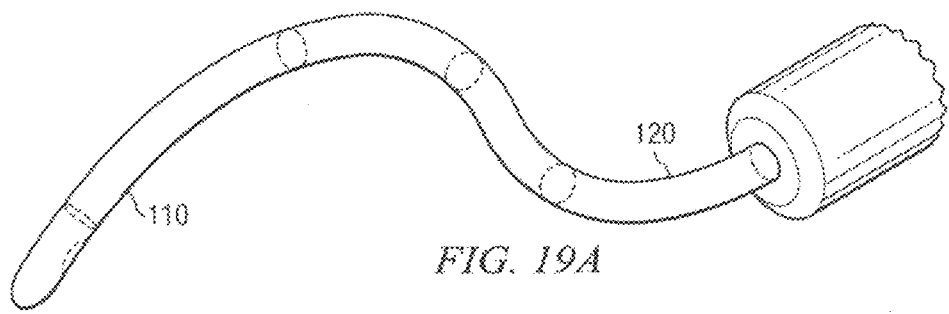

FIG. 19A shows a perspective view of a fixed shape cannula 100 wherein the cross section of the distal portion 110 and the proximal portion 120 are generally circular.

Figure 19B:
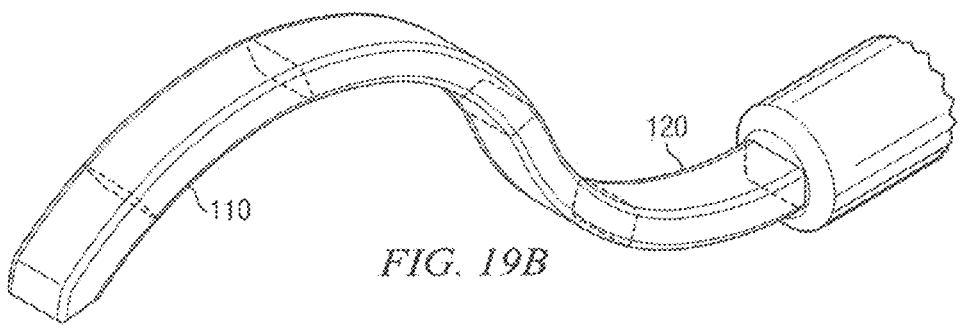

FIG. 19B is a perspective view of a fixed shape cannula 100 wherein the cross section of the distal portion 110 and the proximal portion 120 is flattened in a ribbon-like configuration.

Figure 20A:
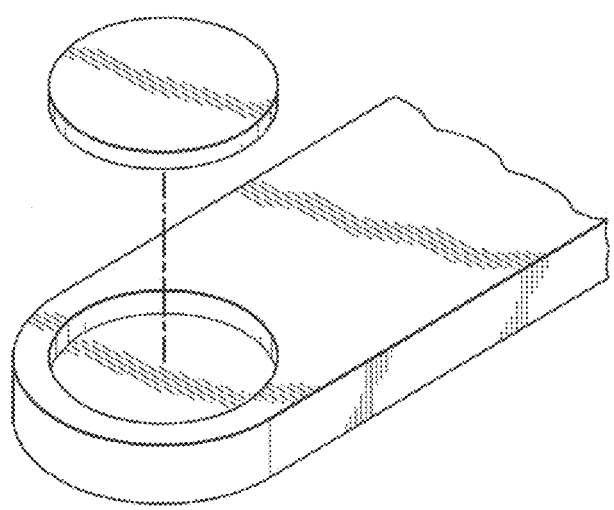

FIG. 20A shows a perspective view of a disk-shaped RBS inserted into a means for advancing the RBS toward the tip 200 of the fixed shape cannula 100.

Figure 20B:
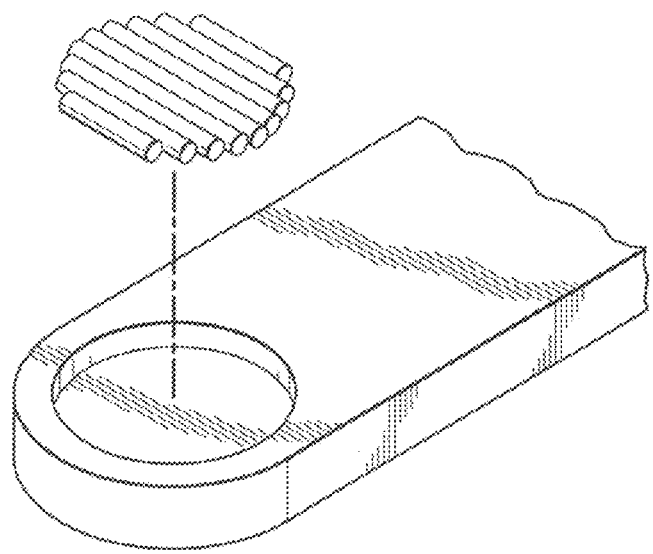

FIG. 20B is a perspective view of a plurality of cylindrical RBSs inserted into a means for advancing the RBS toward the tip 200 of the fixed shape cannula 100.

Figure 21:
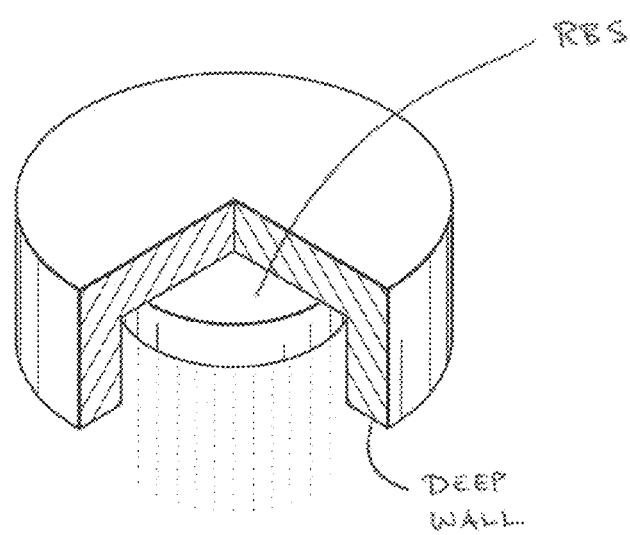

FIG. 21 shows a perspective view of a well having radio opaque walls, and a radionuclide brachytherapy source is set in the well.

Figure 22:
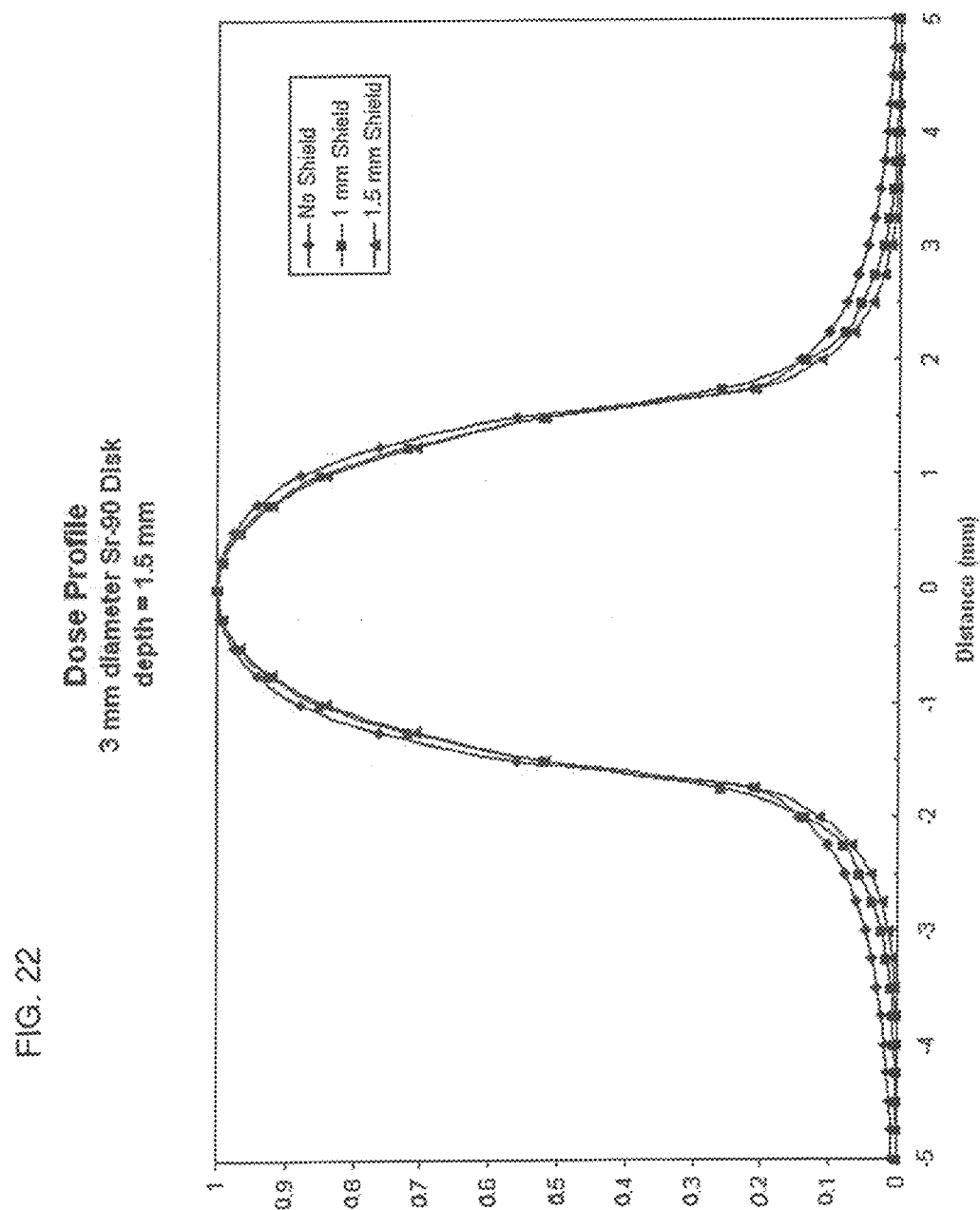

FIG. 22 shows the radiation profiles where the intensity of the radiation at the edge falls off significantly, i.e., there is a fast fall of at the target edge. When a shielding is employed, the radiation fall off at the edge is faster compared to when there is no shielding.

Figure 23:
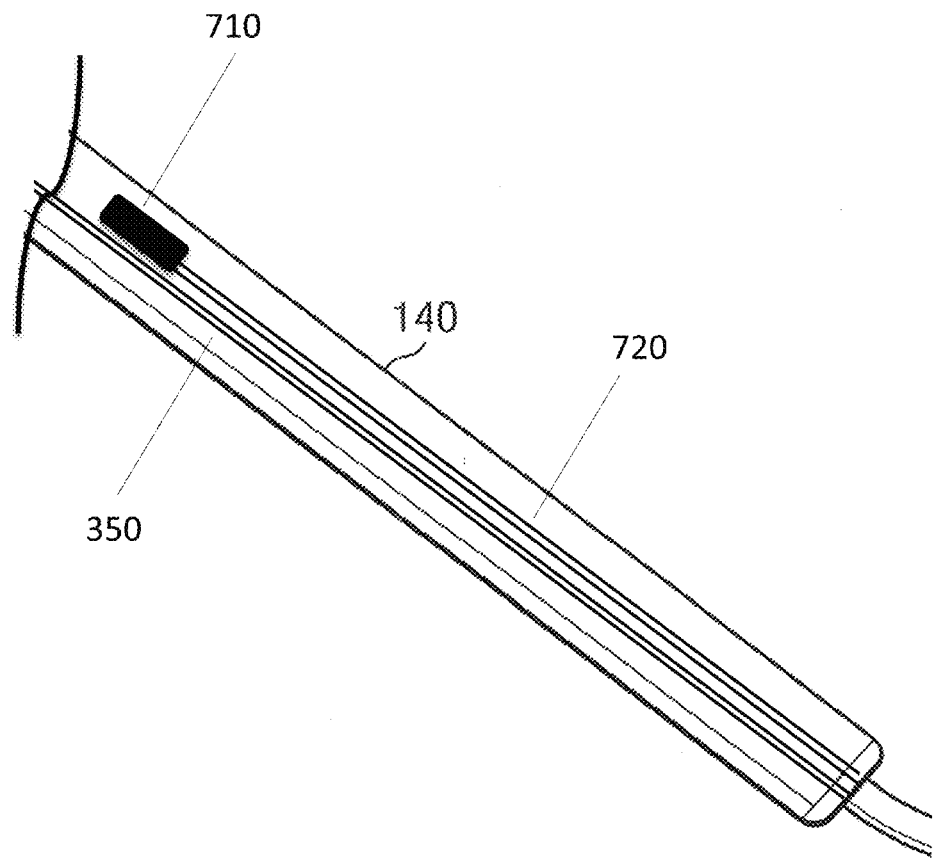
Figure 23A:
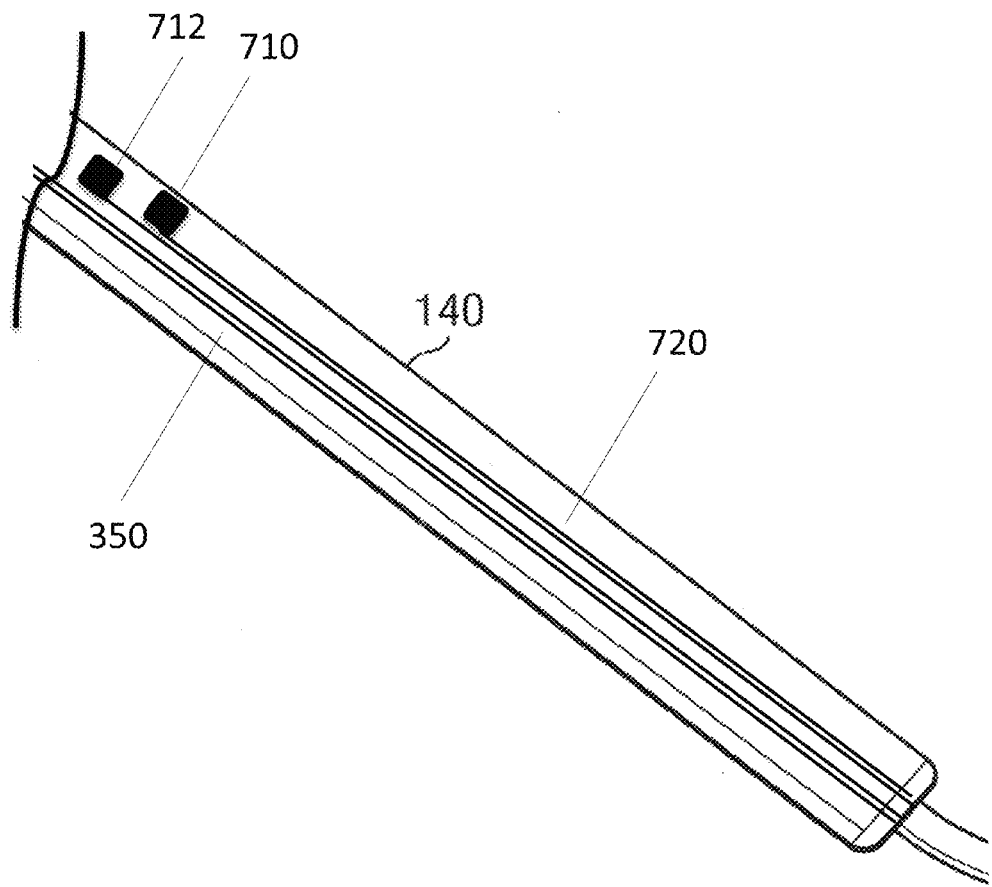

FIG. 23 shows a side view of the handle. FIG. 23A shows an alternate side view of the handle.

Figure 24:
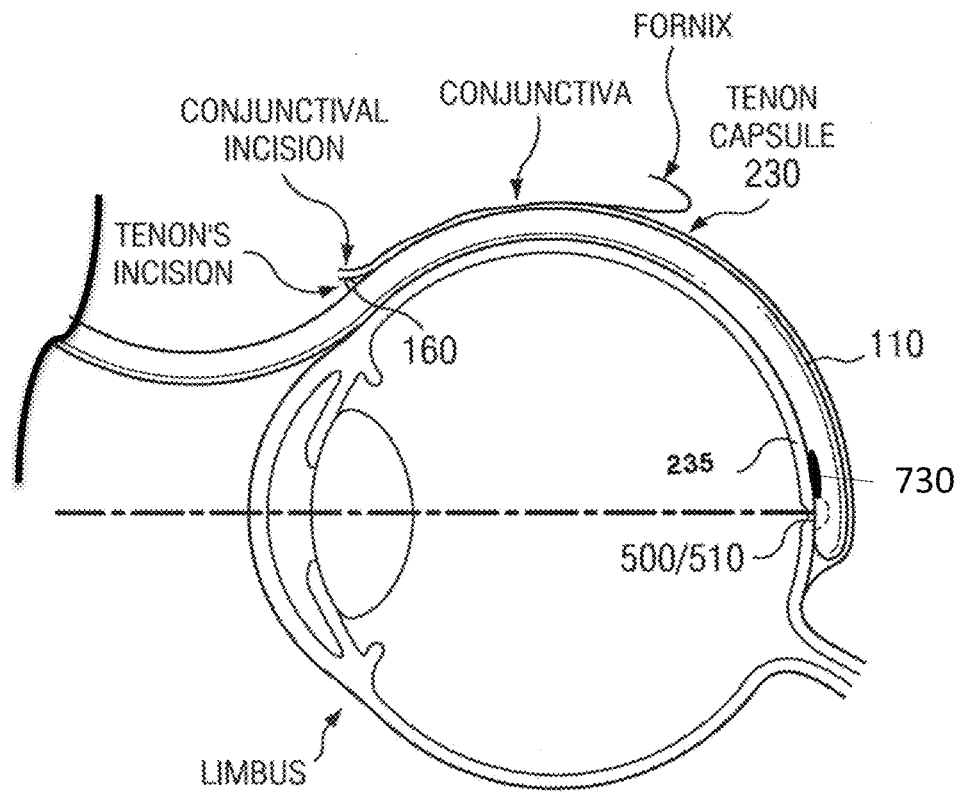
Figure 24A:
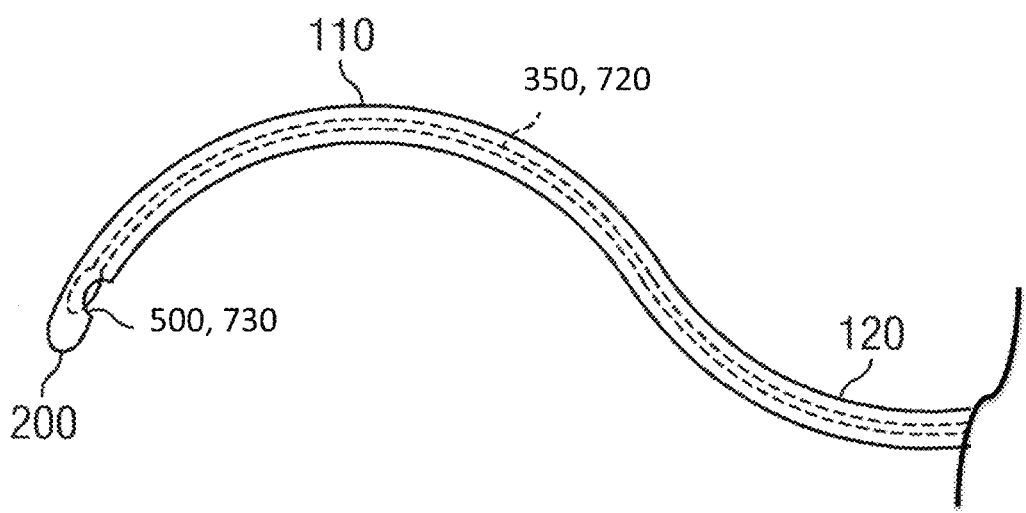

FIG. 24 shows the insertion of the cannula into the eye. FIG. 24A shows a side view of a cannula.

Figure 25:
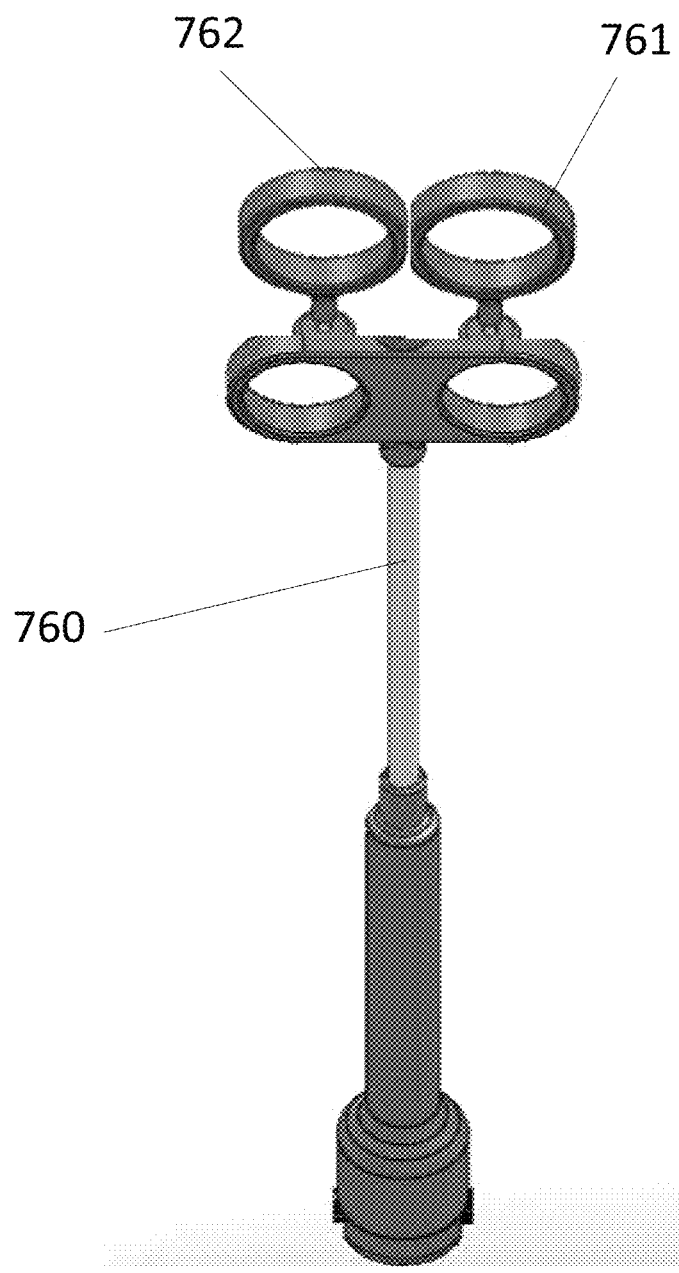

FIG. 25 shows a perspective view of the present device.

FIG. 26 shows a table with combinations of dimensions for a, b and c.

FIG. 27 shows a table with combinations of dimensions for d, e and f.

FIG. 28 shows a table with a listing for non-limiting examples of such Sr-90-constructed radioactive seeds.

FIG. 29 shows a table with various relative radiation doses according to depth (distance away from source).

Figure 30:
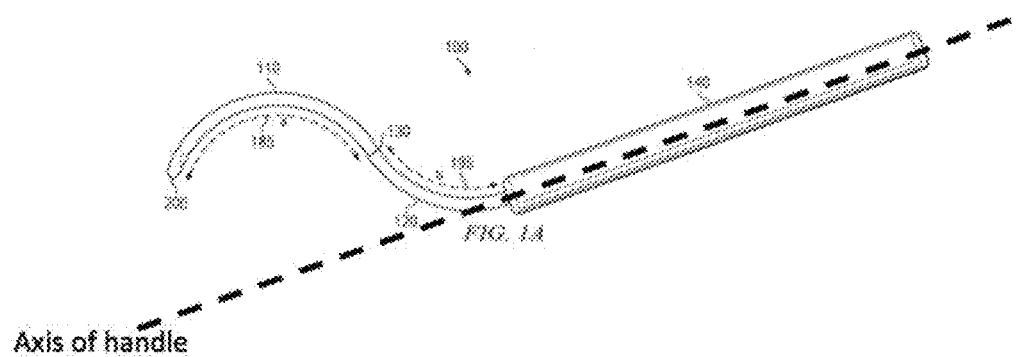

FIG. 30 shows the axis of the handle (wherein the axis does not intersect with the distal portion, e.g., the tip of the distal portion). Without wishing to limit the present invention to any theory or mechanism, this configuration may be helpful for providing better visualization for a physician (e.g., the handle does not obstruct the visual axis for the physician).

Figure 31:
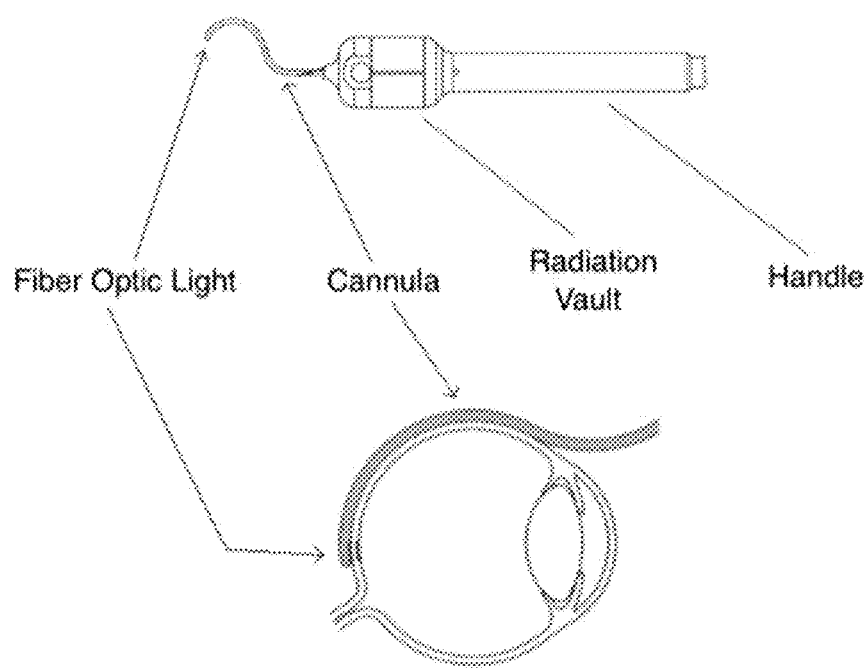

FIG. 31 is a side view of a device of the present invention comprising a handle, a shield compartment (e.g., PIC), a cannula with a curved distal portion, and a fiber optic light near the tip of the device. FIG. 31 also shows the curvature of the cannula portion of the device, wherein the cannula curves around a portion of the eye to deliver the tip of the device to the back of the eye.

Figure 32:
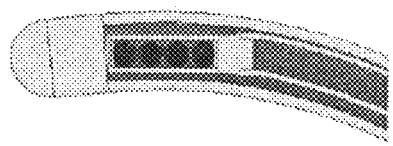

FIG. 32 is a detailed view of an example of a radionuclide brachytherapy source (RBS) (or radiation source) at the tip of the cannula of the device of the present invention.

Figure 33:
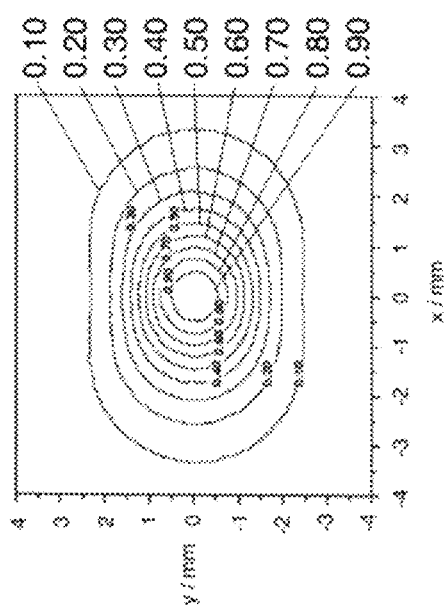

FIG. 33 is a diagram showing the relative dose distribution in Gy/min at 1.5 mm distance from the source. The isodose lines are normalized to the central point.

Figure 34:
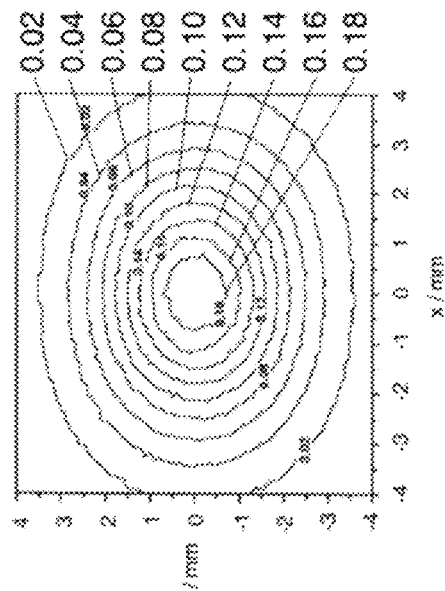

FIG. 34 is a diagram showing the relative dose distribution in Gy/min at 3 mm distance from the source. The isodose lines are normalized to the central point at 1.5 mm depth.

Figure 35:
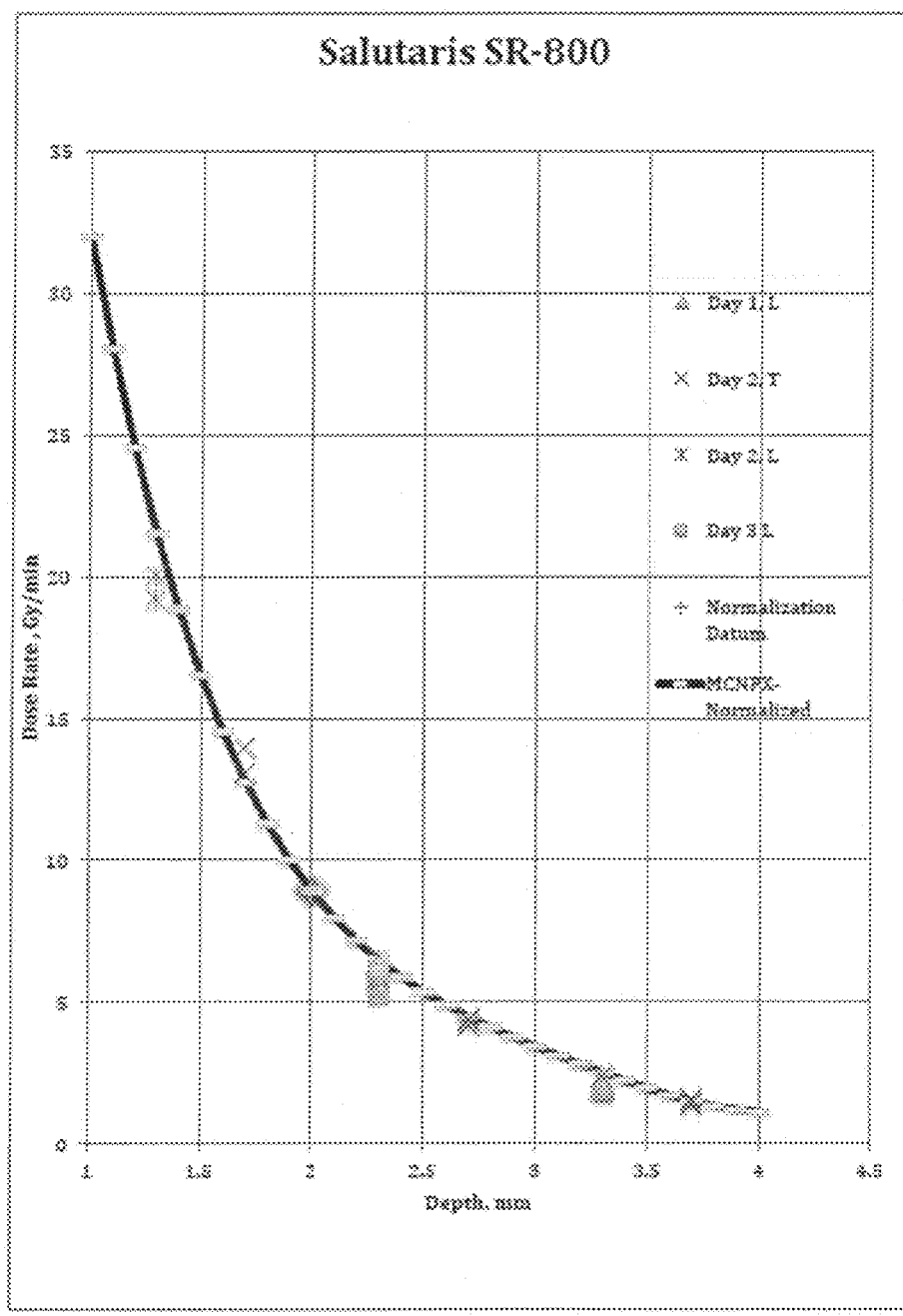

FIG. 35 is a diagram showing the several central axis dose determinations on different days and the two different techniques for setting the depths. The dose rate is shown as a function of depth from the source center for the several measurements conducted, the one determination at 2.0 by the manufacturer, and the MCNPX calculations normalized to 8.9 Gy/min at 2.0 mm. Experimental dose rates were determined from the dose measured from an exposure divided by the time of the exposure. The label "T" refers to measurement in the treatment configuration (cylindrical phantom) while "L" refers to the lateral measurement using the side of the cannula on the flat phantom.

Figure 36:
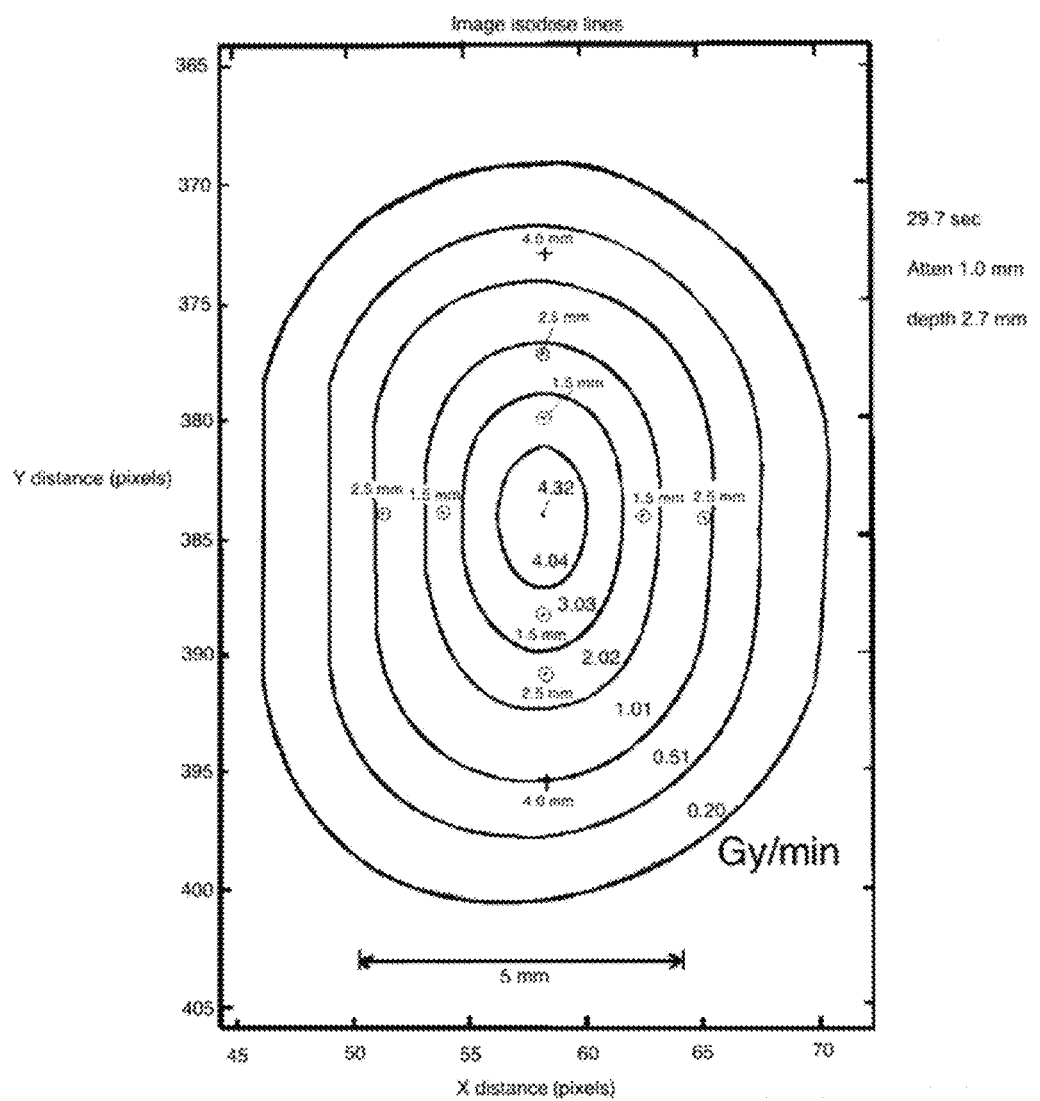

FIG. 36 is a diagram showing isodose lines at 2.7 mm determined experimentally and analyzed by hand. The dose rates are determined from the absolute doses measured for this exposure divided by the time of the exposure.

Figure 37:
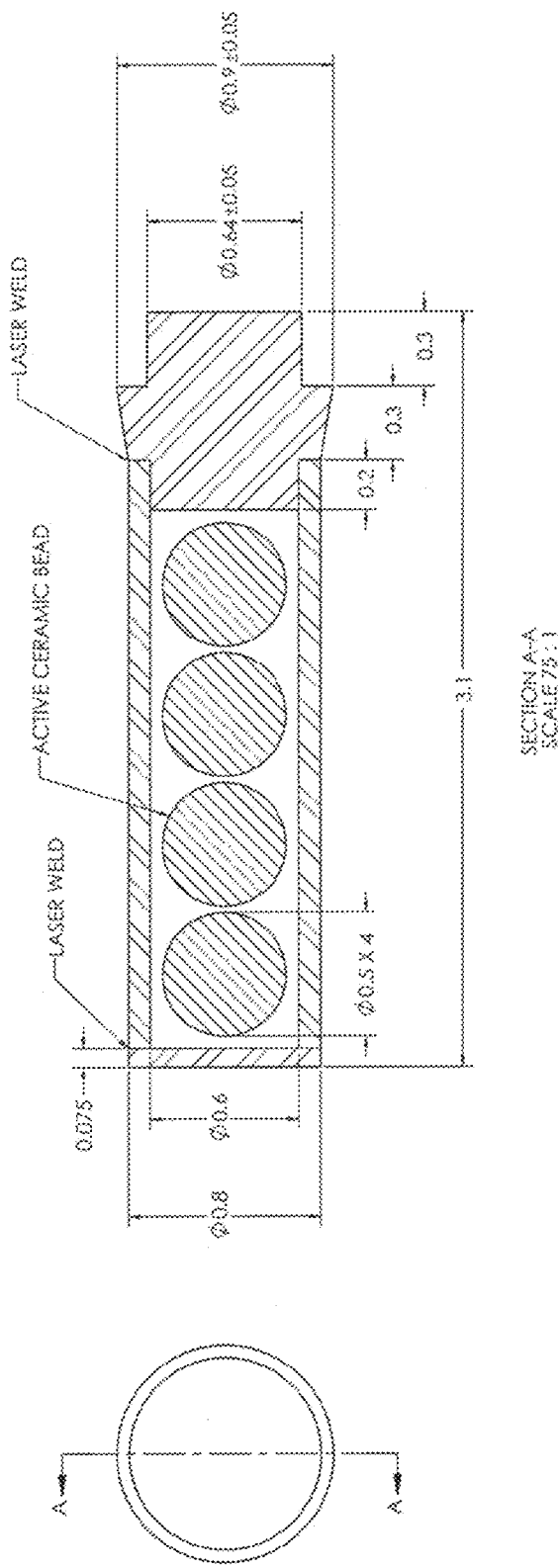

FIG. 37 shows a schematic view of a radionuclide brachytherapy source (RBS, radiation source) of the present invention.

DESCRIPTION OF PREFERRED EMBODIMENTS

The present invention features methods and devices for minimally-invasive delivery of radiation to the posterior portion of the eye. Without wishing to limit the present invention to any theory or mechanism, it is believed that the sub-tenon method of delivering radiation to the posterior portion of the eye of the present invention is advantageous for several reasons. For example, the sub-tenon procedure is minimally invasive and does not require extensive surgical dissections. Thus, this unique procedure is faster, easier, and will present fewer side effects and/or complications the prior art methods that otherwise require dissections. Moreover, the sub-tenon method may allow for simple office-based procedures with faster recovery times.

The sub-tenon method also allows for the tenon's capsule and other structures (e.g., sclera) to help guide and hold the device in place when in use. Keeping the cannula in a fixed location and at a distance from the target during the treatment reduces the likelihood of errors and increases the predictability of dose delivery. In an intravitreal approach (e.g., irradiating the target area by directing the radiation from within the vitreous chamber from anteriorly to the retina of the eye back towards the target), a physician is required to hold the device in a fixed location and a fixed distance from the target in the spacious vitreous chamber (see FIG. 9). It may be difficult for the physician to hold precisely that position for any length of time. Furthermore, it is generally not possible for the physician/surgeon to know the exact distance between the probe and the retina; he/she can only estimate the distance.

The methods of the present invention direct radiation from the posterior side of the eye forwardly to a target; radiation is shielded in the back. Without wishing to limit the present invention to any theory or mechanism, it is believed that these methods will spare the patient from receiving ionizing radiation in the tissues behind the eye and deeper than the eye. A pre-retinal approach (e.g., irradiating the target area by directing the radiation from the anterior side of the retina back toward the target) irradiates the anterior structures of the eye (e.g., cornea, iris, ciliary body, lens) and has the potential to irradiate the tissues deeper than the lesion, such as the periorbital fat, bone, and the brain. An intravitreal radiation approach also has the potential to irradiate the tissues deeper than the lesion (e.g., periorbital fat, bone, brain) and also, in a forward direction, the lens, ciliary body and cornea.

Prior to the present invention, radiotherapy as applied to the eye generally involves invasive eye surgeries. For example, an authoritative report in the radiation therapy industry known as the "COMS study" discloses a protocol that employs an invasive surgical procedure to dissect the periocular tissues and place the brachytherapy device. This is unlike the presently inventive minimally invasive sub-tenon method.

The prior art has disclosed a number of brachytherapy devices and methods of using same for irradiating a lesion from behind the eye. However, these techniques do not employ the minimally invasive subtenon approach of the present invention. Upon reading the disclosures of the prior art, one of ordinary skill would easily recognize that the procedure being disclosed is quadrant dissection approach or a retro-bulbar intra-orbital approach, neither of which is the minimally invasive subtenon approach.

The following is a listing of numbers corresponding to a particular element refer to herein:
  100 fixed shape cannula
  110 distal portion
  112 distal region of distal portion
  113 middle region of distal portion
  120 proximal portion
  130 inflection point
  140 handle
  150 connector
  160 locator
  171 inner diameter of cannula
  172 outer diameter of cannula
  173 inner radius of proximal portion 180 radius of curvature of distal portion
181 circle/oval defined by curve of distal portion
182 radius of circle/oval defined by curve of distal portion
185 arc length of distal portion
190 radius of curvature of proximal portion
191 circle/oval defined by curve of proximal portion
192 radius of circle/oval defined by curve of proximal portion
195 arc length of proximal portion
200 tip
210 distal chamber (disc-shaped)
220 visual axis of user
230 Tenon's capsule
235 sclera
300 memory wire
310 flat spiral
320 distal end of wire
350 guide wire
361 substrate
362 isotope (or "radionuclide")
363 bottom surface of substrate
364 window of radiation shaper
366 radiation shaper
400 seed-shaped RBS
405 disk
406 height of disk
407 diameter of disk
410 radioactive source portion of wire
420 line $l_3$
425 angle $\theta_1$
431 plane $P_1$
432 plane $P_2$
450 ellipsoid
500 orifice
510 window
520 distal edge of orifice/window
600 indentation tip
610 light source
800 non-wire plunger
810 thumb ring
820 graduated dial
830 slider
900 radiation shielding pig
910 device used for intravitreal radiation approach As used herein, the term "about" means plus or minus 10% of the referenced number. For example, an embodiment wherein an angle is about 50 degrees includes an angle between 45 and 55 degrees.

The Eye

The mammalian eye is a generally spherical structure that performs its visual function by forming an image of an exterior illuminated object on a photosensitive tissue, the retina. The basic supporting structure for the functional elements of the eye is the generally spherical tough, white outer shell, the sclera 235, which is comprised principally of collagenous connective tissue and is kept in its spherical shape by the internal pressure of the eye. Externally the sclera 235 is surrounded by the Tenon's capsule 230 (fascia bulbi), a thin layer of tissue running from the limbus anteriorly to the optic nerve posteriorly. The Tenon's capsule 230 is surrounded anteriorly by the bulbar conjunctiva, a thin, loose, vascularized lymphatic tissue that originates at the limbus and reflects posteriorly into the tarsal conjunctiva at the conjunctival fornix. Anteriorly the sclera 235 joins the cornea, a transparent, more convex structure. The point where the sclera and cornea is called the limbus. The anterior portion of the sclera 235 supports and contains the elements that perform the function of focusing the incoming light, e.g., the cornea and crystalline lens, and the function of regulating the intensity of the light entering the eye, e.g., the iris. The posterior portion of the globe supports the retina and associated tissues.

In the posterior portion of the globe (referred to herein as the "posterior portion of the eye") immediately adjacent the interior surface of the sclera 235 lays the choroid, a thin layer of pigmented tissue liberally supplied with blood vessels. The portion of the choroid adjacent its interior surface is comprised of a network of capillaries, the choriocapillaris, which is of importance in the supply of oxygen and nutrients to the adjacent layers of the retina. Immediately anterior to the choroid lies the retina, which is the innermost layer of the posterior segment of the eye and receives the image formed by the refractive elements in the anterior portion of the globe. The photoreceptive rod and cone cells of the retina are stimulated by light falling on them and pass their sensations via the retinal ganglion cells to the brain. The central region of the retina is called "macula"; it is roughly delimited by the superior and inferior temporal branches of the central retina artery, it is mostly responsible for color vision, contrast sensitivity and shape recognition. The very central portion of the macula is called "fovea" and is responsible for fine visual acuity.

Novel Subtenon Approach to Introduce a Radionuclide Brachytherapy Source ("RBS") to Posterior of Eye Globe The present invention features a method of introducing radiation to the posterior portion of the eye in a minimally-invasive manner (by respecting the intraocular space). Generally, the method comprises irradiating from the outer surface of the sclera 235 to irradiate a target. The target may be the macula, the retina, the sclera 235, and/or the choroid. In some embodiments, the target may be on the vitreous side of the eye. In some embodiments, the target is a neovascular lesion. In some embodiments, the target receives a dose rate of radiation of greater than about 10 Gy/min.

In some embodiments, the method comprises using a hollow cannula 100 to deliver a RBS to the region of the sclera 235 corresponding to the target. (Although a cannula 100 of the present invention is used in the subtenon approach, other instruments such as an endoscope may also be used in accordance with present novel subtenon approach). The cannula 100 may be slid on the exterior curvature of the eye to reach the posterior portion of the eye. More specifically, in some embodiments, the method comprises introducing a cannula 100 comprising a RBS to the posterior portion of the eye between the Tenon's capsule 230 and the sclera 235 and exposing the posterior portion of the eye to the radiation. The cannula 100 may be inserted at a point posterior to the limbus of the eye (e.g., any point between the limbus and the conjunctival fornix).

The method may further comprise advancing a RBS through the cannula 100 to the tip 200 of the distal portion 110 via a means for advancing the RBS.

In some embodiments, the method further comprises the step of exposing the target (e.g., macula) of the eye to the radiation. In some embodiments, the method comprises targeting a neovascular growth in the macula.

In some embodiments, the RBS is placed in the subtenon space in close proximity to the portion of the sclera 235 that overlays a portion of choroid and/or retina affected by an eye condition (e.g., WAMD, tumor). As used herein, a RBS that is placed "in close proximity" means that the RBS is about 0 mm to about 10 mm from the surface of the sclera 235. In some embodiments, the radiation irradiates through the sclera 235 to the choroid and/or retina.

In some embodiments, the step of inserting the cannula 100 between the Tenon's capsule 230 and the sclera 235 further comprises inserting the cannula 100 into the superior temporal quadrant of the eye. In some embodiments, the step of inserting the cannula 100 between the Tenon's capsule 230 and the sclera 235 further comprises inserting the cannula 100 into the inferior temporal quadrant of the eye. In some embodiments, the step of inserting the cannula 100 between the Tenon's capsule 230 and the sclera 235 further comprises inserting the cannula 100 into the superior nasal quadrant of the eye. In some embodiments, the step of inserting the cannula 100 between the Tenon's capsule 230 and the sclera 235 further comprises inserting the cannula 100 into the inferior nasal quadrant of the eye.

A RBS disposed at the distal end of a cannula 100 irradiates the target, and the target receives a dose rate of greater than about 10 Gy/min. In some embodiments, the RBS provides a dose rate of greater than about 11 Gy/min to the target. In some embodiments, the RBS provides a dose rate of greater than about 12 Gy/min to the target. In some embodiments, the RBS provides a dose rate of greater than about 13 Gy/min to the target. In some embodiments, the RBS provides a dose rate of greater than about 14 Gy/min to the target. In some embodiments, the RBS provides a dose rate of greater than about 15 Gy/min to the target. In some embodiments, the RBS provides a dose rate between about 10 to 15 Gy/min. In some embodiments, the RBS provides a dose rate between about 15 to 20 Gy/min. In some embodiments, the RBS provides a dose rate between about 20 to 30 Gy/min. In some embodiments, the RBS provides a dose rate between about 30 to 40 Gy/min. In some embodiments, the RBS provides a dose rate between about 40 to 50 Gy/min. In some embodiments, the RBS provides a dose rate between about 50 to 60 Gy/min. In some embodiments, the RBS provides a dose rate between about 60 to 70 Gy/min. In some embodiments, the RBS provides a dose rate between about 70 to 80 Gy/min. In some embodiments, the RBS provides a dose rate between about 80 to 90 Gy/min. In some embodiments, the RBS provides a dose rate between about 90 to 100 Gy/min. In some embodiments, the RBS provides a dose rate of greater than 100 Gy/min.

In some embodiments, the distance from the RBS to the target is between about 0.4 to 2.0 mm. In some embodiments, the distance from the RBS to the target is between about 0.4 to 1.0 mm. In some embodiments, the distance from the RBS to the target is between about 1.0 to 1.6 mm. In some embodiments, the distance from the RBS to the target is between about 1.6 to 2.0 mm.

In some embodiments, the RBS provides a dose rate between about 15 to 20 Gy/min to the target. In some embodiments, the RBS provides a dose rate between about 20 to 25 Gy/min to the target. In some embodiments, the RBS provides a dose rate between about 25 to 30 Gy/min to the target. In some embodiments, the RBS provides a dose rate between about 30 to 35 Gy/min to the target. In some embodiments, the RBS provides a dose rate between about 35 to 40 Gy/min to the target. In some embodiments, the RBS provides a dose rate between about 40 to 50 Gy/min to the target. In some embodiments, the RBS provides a dose rate between about 50 to 60 Gy/min to the target. In some embodiments, the RBS provides a dose rate between about 60 to 70 Gy/min to the target. In some embodiments, the RBS provides a dose rate between about 70 to 80 Gy/min to the target. In some embodiments, the RBS provides a dose rate between about 80 to 90 Gy/min to the target. In some embodiments, the RBS provides a dose rate between about 90 to 100 Gy/min to the target. In some embodiments, the RBS provides a dose rate greater than about 100 Gy/min to the target.

The present methods may be effective for treating and/or managing a condition (e.g., an eye condition). For example, the present methods may be used to treat and/or manage wet (neovascular) age-related macula degeneration. The present methods are not limited to treating and/or managing wet (neovascular) age-related macular degeneration. For example, the present methods may also be used to treat and/or manage conditions including macula degeneration, abnormal cell proliferation, choroidal neovascularization, retinopathy (e.g., diabetic retinopathy, vitreoretinopathy), macular edema, and tumors (e.g., intra ocular melanoma, retinoblastoma).

Advantages of Subtenon Procedure

Without wishing to limit the present invention to any theory or mechanism, it is believed that the novel subtenon methods of the present invention are advantageous over the prior art because they are less invasive (e.g., they do not invade the intraocular space), they require only local anesthesia, and they provide a quicker patient recovery time. For example, the technique of introducing radiation to the posterior portion of the eye by suturing a radioactive plaque on the sclera 235 at the posterior portion of the eye requires a 360° peritomy (e.g., dissection of the conjunctiva), isolation of the four recti muscles and extensive manipulation of the globe. Furthermore, when the plaque is left in place and then removed a few days later, a second surgery is required. The methods of the present invention are easier to perform. Also, the intraocular method of exposing the posterior pole of the eye to radiation involves performing a vitrectomy as well as positioning and holding the radioactive probe in the preretinal vitreous cavity for a significant length of time without a stabilizing mechanism. This technique is difficult to perform, requires a violation of the intraocular space, and is prone to a number of possible complications such as the risk of retinal detachment, cataracts, glaucoma, and/or endophthalmitis. Because of the complexity of this technique, a fellowship in vitreoretina surgery is required. The methods of the present invention are easier to perform, minimally-invasive, and do not impose a risk of damage to the intraocular structures. Moreover, the methods of the present invention do not require additional vitreoretina fellowship training as these methods can be employed by any surgical ophthalmologist.

As used herein, the term "minimally-invasive" method means a method that does not require that an instrument be introduced into the intraocular space (anterior, posterior, or vitreous chamber) of the eye for delivery of a radioactive source to the posterior portion of the eye or a method that does not require the suturing of a radioactive plaque on the sclera 235 or extensive conjunctiva peritomy. For example, the minimally-invasive methods of the present invention only require a small incision of conjunctiva and Tenon's capsule 230 for inserting of a cannula 100 comprising a RBS to the posterior portion of the eye. The preferred approach is through the superotemporal quadrant, however entrance through the supero nasal, the inferotemporal or the inferonasal quadrant can be employed.

The present invention features a method of introducing radiation to a human eye comprising the steps of inserting a cannula 100 between the Tenon's capsule 230 and the sclera 235 of the human eye at a point posterior to the limbus of the human eye; wherein the cannula 100 comprises a distal portion 110 having a radius of curvature 180 between about 9 to 15 mm and an arc length 185 between about 25 to 35 mm; a proximal portion 120; and a means for advancing a RBS toward the tip 200 of the cannula 100 (e.g., tip 200 of distal portion 110); placing the distal portion 110 on or near the sclera 235 behind a neovascular lesion; advancing the RBS to the tip 200 of the distal end 110; and exposing the neovascular lesion to the RBS.

In some embodiments, the area of sclera 235 exposed to the radiation is about 0.1 mm to about 0.5 mm in diameter. In some embodiments, the area of sclera 235 exposed to the radiation is about 0.5 mm to about 2 mm in diameter. In some embodiments, the area of sclera 235 exposed to the radiation is about 2 mm to 3 mm in diameter. In some embodiments, the area of sclera 235 exposed to the radiation is about 3 mm to 5 mm in diameter. In some embodiments, the area of sclera 235 exposed to the radiation is about 5 mm to 10 mm in diameter. In some embodiments, the area of sclera 235 exposed to the radiation is about 10 mm to 25 mm in diameter.

The Cannula

The present invention features a fixed shape cannula 100 for delivering a RBS to the back of the eye. The fixed shape cannula 100 has a defined, fixed shape and comprises a distal portion 110 connected to a proximal portion 120 via an inflection point 130. The distal portion 110 of the fixed shape cannula 100 is for placement around a portion of the globe of the eye. In some embodiments, the distal portion 110 of the fixed shape cannula 100 is inserted below the Tenon capsule 230 and above the sclera 235. In some embodiments, the fixed shape cannula 100 is hollow.

As used herein, a fixed shape cannula 100 having a "fixed" shape refers to a fixed shape cannula 100 that has a single permanent shape and cannot be manipulated into another shape. For example, the fixed shape cannula 100 of the present invention has a "fixed" shape because it generally has one shape, whereas an endoscope does not have a "fixed" shape because it is flexible and can be manipulated into another shape. A fixed shape cannula 100 having a "fixed" shape may also be constructed from a material that has some flexibility. Accordingly, when a pressure is applied onto the fixed shape cannula 100 of the present invention it may bend. However, when the pressure is removed, the fixed shape cannula 100 of the present invention may resume its original fixed shape or retain a portion of the deformation shape.

In some embodiments, an inflection point 130 may be defined as a point on a curve in which the sign or direction of the curvature changes. In some embodiments, there may be a straight portion of the fixed shape cannula between the distal portion and proximal portion. Accordingly, in some embodiments, the proximal and distal portions are separated at an inflection point where the curvature changes sign. In some embodiments, the proximal portion ends at a point where the curvature changes from a finite value to zero.

In some embodiments, the inflection point 130 helps to bend the proximal portion 120 of the fixed shape cannula 100 away from the visual axis 220 of the subject (e.g., patient) and of the user (e.g., physician) who inserts the fixed shape cannula 100 into a subject. In some embodiments, the user may visualize the posterior portion of the eye of the subject by employing a coaxial ophthalmoscopic device such as an indirect ophthalmoscope or a surgical microscope while the fixed shape cannula 100 is in place.

Distal Portion Dimensions of the Fixed Shape Cannula

The dimensions of the globe of the eye are fairly constant in adults, usually varying by no more than about 1 mm in various studies. However, in hyperopia and myopia, the anteroposterior diameter of the globe may vary significantly from the normal measurement.

The outer anteroposterior diameter of the globe ranges between about 21.7 mm to 28.75 mm with an average of about 24.15 mm (radius ranges from about 10.8 mm to 14.4 mm with an average of about 12.1 mm) in emmetropic eyes, whereas the internal anteroposterior diameter averages about 22.12 mm (radius averages about 11.1 mm). In high hypermetropia and myopia, the anteroposterior diameter is frequently as low as about 20 mm and as high as about 29 mm or more, respectively.

The transverse diameter (e.g., the diameter of the globe at the anatomic equator measured from the nasal to the temporal side) averages about 23.48 mm (radius averages about 11.75 mm), and the vertical diameter (e.g., the diameter of the globe at the anatomic equator measured superiorly to inferiorly) averages about 23.48 mm (radius averages about 11.75 mm). The circumference of the globe at the anatomic equator averages about 74.91 mm. The volume of the globe of the eye averages between about 6.5 mL to 7.2 mL, and has a surface area of about 22.86 cm$^2$.

The distal portion 110 of the fixed shape cannula 100 may be designed in a number of ways. In some embodiments, the distal portion 110 of the fixed shape cannula 100 has an arc length 185 between about 25 to 35 mm.

In some embodiments, the arc length 185 of the distal portion 110 (e.g., length of the arc 111 of the distal portion 110) may be of various lengths. For example, hyperopic or pediatric patients may have smaller eyes and may require a smaller arc length 185 of the distal portion 110. Or, for example, different insertion points (e.g., limbus, conjunctival fornix) of the fixed shape cannula 100 may require different arc lengths 185 of the distal portion 110. In some embodiments, the arc length 185 of the distal portion 110 may be between about 10 mm to about 15 mm. In some embodiments, the arc length 185 of the distal portion 110 may be between about 15 mm to about 20 mm. In some embodiments, the arc length 185 of the distal portion 110 may be between about 20 mm to about 25 mm. In some embodiments, the arc length 185 of the distal portion 110 may be between about 25 mm to about 30 mm. In some embodiments, the arc length 185 of the distal portion 110 may be between about 30 mm to about 35 mm. In some embodiments, the arc length 185 of the distal portion 110 may be between about 35 mm to about 50 mm. In some embodiments, the arc length 185 of the distal portion 110 may be between about 50 mm to about 75 mm.

As used herein, the term "arc length" 185 of the distal portion 110 of the fixed shape cannula refers to the arc length measured from the tip 200 of the distal portion 110 to the inflection point 130. The term "radius of curvature" 180 of the distal portion 110 of the fixed shape cannula 100 refers to the length of the radius 182 of the circle/oval 181 defined by the curve of the distal portion 110 (see FIG. 19A). In some embodiments, the invention employs a unique sub-tenon insertion methodology, wherein the arc length is designed to be of sufficient length to traverse the Tenon's capsule and portion of the eye which is interposed between the Tenon's capsule entry point and the target (e.g., macula) area.

In some embodiments, the distal portion 110 of the fixed shape cannula 100 has a radius of curvature 180 between about 9 to 15 mm. In some embodiments, the radius of curvature 180 of the distal portion 110 is between about 9 mm to about 10 mm. In some embodiments, the radius of curvature 180 of the distal portion 110 is between about 10 mm to about 11 mm. In some embodiments, the radius of curvature 180 of the distal portion 110 is between about 11 mm to about 12 mm. In some embodiments, the radius of curvature 180 of the distal portion 110 is between about 12 mm to about 13 mm. In some embodiments, the radius of curvature 180 of the distal portion 110 is between about 13 mm to about 14 mm. In some embodiments, the radius of curvature 180 of the distal portion 110 is between about 14 mm to 15 mm. In some embodiments, the arc length 185 of the distal portion 110 and the inflection point 130 may also serve to limit the depth of insertion of the fixed shape cannula 100 along the sclera 235, preventing the tip 200 of the distal portion 110 from accidentally damaging posterior ciliary arteries or the optic nerve.

In some embodiments, the distal portion 110 has a radius of curvature 180 substantially equal to the radius of curvature of the sclera 235 of an adult human eye. Without wishing to limit the present invention to any theory or mechanism, it is believed that having the radius of curvature 180 of the distal portion 110 be substantially equal to the radius of curvature of the sclera 235 of an adult human eye is advantageous because it will ensure that the area that is exposed to the radiation is the outer surface of the sclera 235, generally above the macula. In addition, the design permits accurate placement of the RBS and allows a user (e.g., a surgeon) to have the RBS remain fixed in the correct position with minimal effort during the application of the radiation dose. This enables improved geometric accuracy of dose delivery and improved dosing.

In some embodiments, the radius of curvature 180 of the distal portion 110 is constant. For example, the radius of curvature 180 in the distal portion 110 may be a constant 12 mm. In some embodiments, the radius of curvature 180 of the distal portion 110 is variable. For example, the radius of curvature 180 in the distal portion 110 may be larger at the distal region 112 and smaller at the middle region 113.

Without wishing to limit the present invention to any theory or mechanism, it is believed that different and variable radii of curvature may provide for easier and more accurate positioning in special cases, such as that of a myopic eye in which the anteroposterior diameter is greater than the vertical diameter. In this case, it may be advantageous to use a fixed shape cannula 100 having a distal portion 110 with an overall larger radius of curvature 180 and specifically having a relatively shorter radius of curvature in the distal region 112 as compared to the radius of curvature in the middle region 113. Similarly, it may be advantageous to use a fixed shape cannula 100 having a distal portion 110 with an overall smaller radius of curvature 180 and specifically having a relatively larger radius of curvature in the distal region 112 as compared to the radius of curvature in the middle region 113.

The distal portion 110 and the proximal portion 120 of the fixed shape cannula 100 each have an inner diameter 171 and outer diameter 172 of the respective vertical cross sections. As shown in FIG. 16, in some embodiments, the inner diameter 171 of the vertical cross section of the distal portion 110 is constant (e.g., the inside of the fixed shape cannula 100 has a circular cross section). In some embodiments, the inner diameter 171 of the vertical cross section of the distal portion 110 is variable (e.g., the inside of the fixed shape cannula 100 has an oval cross section). In some embodiments, the outer diameter 172 of vertical cross section of the distal portion 110 is constant (e.g., the outside of the fixed shape cannula 100 has a circular cross section). In some embodiments, the outer diameter 172 of the vertical cross section of the distal portion 110 is variable (e.g., the outside of the fixed shape cannula 100 has an oval cross section).

In some embodiments, the fixed shape cannula 100 has an outer cross sectional shape that is generally circular. In some embodiments, the fixed shape cannula 100 has an outer cross sectional shape that is generally round. In some embodiments, the fixed shape cannula 100 has an outer cross sectional shape that is oval, rectangular, egg-shaped, or trapezoidal.

In some embodiments, the fixed shape cannula 100 has an internal cross sectional shape that is configured to allow a RBS to be passed through.

In some embodiments, the fixed shape cannula 100 has an internal cross sectional shape that is generally circular. In some embodiments, the fixed shape cannula 100 has an outer cross sectional shape that is generally round. In some embodiments, the fixed shape cannula 100 has an inner cross sectional shape that is oval, rectangular, egg-shaped, or trapezoidal.

In some embodiments, the average outer diameter 172 of the vertical cross section of the distal portion 110 is between about 0.1 mm and 0.4 mm. In some embodiments, the average outer diameter 172 of the distal portion 110 is between about 0.4 mm and 1.0 mm. In some embodiments, the average outer diameter 172 of the distal portion 110 is about 0.9 mm. In some embodiments, the average outer diameter 172 of the distal portion 110 is between about 1.0 mm and 2.0 mm. In some embodiments, the average outer diameter 172 of the distal portion 110 is between about 2.0 mm and 5.0 mm. In some embodiments, the average outer diameter 172 of the distal portion 110 is between about 5.0 mm and 10.0 mm.

In some embodiments, the average inner diameter 171 of the vertical cross section of the distal portion 110 is between about 0.1 mm and 0.4 mm. In some embodiments, the average inner diameter 171 of the distal portion 110 is between about 0.4 mm and 1.0 mm. In some embodiments, the average inner diameter 171 of the distal portion 110 is about 0.9 mm. In some embodiments, the average inner diameter 171 of the distal portion 110 is between about 1.0 mm and 2.0 mm. In some embodiments, the average inner diameter 171 of the distal portion 110 is between about 2.0 mm and 5.0 mm. In some embodiments, the average inner diameter 171 of the distal portion 110 is between about 5.0 mm and 10.0 mm.

In some embodiments, the average outer diameter 172 of the vertical cross section of the distal portion 110 is about 0.4 mm and the average inner diameter 171 of the vertical cross section of the distal portion 110 is about 0.1 mm (e.g., the wall thickness is about 0.15 mm). In some embodiments, the average outer diameter 172 of the vertical cross section of the distal portion 110 is about 0.7 mm and the average inner diameter 171 of the vertical cross section of the distal portion 110 is about 0.4 mm (e.g., the wall thickness is about 0.15 mm). In some embodiments, the average outer diameter 172 of the distal portion 110 is about 0.9 mm and the average inner diameter 171 of the distal portion 110 is about 0.6 mm (e.g., the wall thickness is about 0.15 mm). In some embodiments, the average outer diameter 172 of the distal portion 110 is about 1.3 mm and the average inner diameter 171 of the distal portion is about 0.8 mm (e.g., the wall thickness is about 0.25 mm). In some embodiments, the average outer diameter 172 of the distal portion 110 is about 1.7 mm and the average inner diameter 171 of the distal portion 110 is about 1.2 mm (e.g., the wall thickness is about 0.25 mm). In some embodiments, the average outer diameter 172 of the distal portion 110 is about 1.8 mm and the average inner diameter 171 of the distal portion 110 is about 1.4 mm (e.g., the wall thickness is about 0.20 mm). In some embodiments, the average outer diameter 172 of the distal portion 110 is about 2.1 mm and the average inner diameter 171 of the distal portion is about 1.6 mm (e.g., the wall thickness is about 0.25 mm).

In some embodiments, the diameter of the distal portion 110 is between a 12 gauge and 22 gauge wire needle size.

In some embodiments, the thickness of the distal portion wall (e.g., as measured between the inner diameter 171 of the distal portion 110 and the outer diameter 172 of the distal portion 110) is between about 0.01 mm to about 0.1 mm. In some embodiments, the thickness of the distal portion wall (e.g., as measured between the inner diameter 171 of the distal portion 110 and the outer diameter 172 of the distal portion 110) is between about 0.1 mm to about 0.3 mm. In some embodiments, the thickness of the distal portion wall is between about 0.3 mm to about 1.0 mm. In some embodiments, the thickness of the distal portion wall is between about 1.0 mm to about 5.0 mm. In some embodiments, the thickness of the distal portion wall is constant along the length of the distal portion 110. As shown in FIG. 16B, in some embodiments, the thickness of the distal portion wall is constant about the inner diameter 171 and outer diameter 172. In some embodiments, the thickness of the distal portion wall varies throughout the distal portion 110, for example along the length of the distal portion 110. As shown in FIGS. 16C and 16D, in some embodiments, the thickness of the distal portion wall varies about the inner diameter 171 and outer diameter 172.

Proximal Portion Dimensions of the Fixed Shape Cannula

The proximal portion 120 of the fixed shape cannula 100 may also be designed in a number of ways. In some embodiments, the proximal portion 120 of the fixed shape cannula 100 has an arc length 195 between about 10 to 75 mm.

The arc length 195 of the proximal portion 120 (e.g., length of the arc of the proximal portion 120) may be of various lengths. In some embodiments, the arc length 195 of the proximal portion 120 may be between about 10 mm to about 15 mm. In some embodiments, the arc length 195 of the proximal portion 120 may be between about 15 mm to about 18 mm. In some embodiments, the arc length 195 of the proximal portion 120 may be between about 18 mm to about 25 mm. In some embodiments, the arc length 195 of the proximal portion 120 may be between about 25 mm to about 50 mm. In some embodiments, the arc length 195 of the proximal portion 120 may be between about 50 mm to about 75 mm.

As used herein, the term "arc length" 195 of the proximal portion 120 of the fixed shape cannula 100 refers to the arc length measured from the inflection point 130 to the opposite end of the proximal portion 120. The term "radius of curvature" 190 of the proximal portion 120 of the fixed shape cannula 100 refers to the length of the radius 192 of the circle/oval 191 defined by the curve of the proximal portion 120 (see FIG. 19B).

In some embodiments, the proximal portion 120 of the fixed shape cannula 100 has a radius of curvature 190 between about an inner radius 173 of the proximal portion 120 of the fixed shape cannula 100, for example between 0.1 mm to 1 meter. In some embodiments, the radius of curvature 190 of the proximal portion 120 is constant. In some embodiments, the radius of curvature 190 of the proximal portion 120 is variable.

The distal portion 110 and the proximal portion 120 of the fixed shape cannula 100 each have an inner diameter 171 and outer diameter 172 of the respective vertical cross sections. As shown in FIG. 16, in some embodiments, the inner diameter 171 of the vertical cross section of the proximal portion 120 is constant (e.g., the inside of the fixed shape cannula 100 has a circular cross section). In some embodiments, the inner diameter 171 of the vertical cross section of the proximal portion 120 is variable (e.g., the inside of the fixed shape cannula 100 has an oval cross section). In some embodiments, the outer diameter 172 of vertical cross section of the proximal portion 120 is constant (e.g., the outside of the fixed shape cannula 100 has a circular cross section). In some embodiments, the outer diameter 172 of the vertical cross section of the proximal portion 120 is variable (e.g., the outside of the fixed shape cannula 100 has an oval cross section).

In some embodiments, the fixed shape cannula 100 has an outer cross sectional shape that is generally round. In some embodiments, the fixed shape cannula 100 has an outer cross sectional shape that is oval, rectangular, egg-shaped, or trapezoidal.

In some embodiments, the fixed shape cannula 100 has an internal cross sectional shape that is configured to allow a RBS to be passed through.

In some embodiments, the fixed shape cannula 100 has an internal cross sectional shape that is generally round. In some embodiments, the fixed shape cannula 100 has an inner cross sectional shape that is oval, rectangular, egg-shaped, or trapezoidal.

As shown in FIG. 17, line $l_3$ 420 represents the line tangent to the globe of the eye at the inflection point 130 and/or limbus. Line $l_3$ 420 and line $l_4$ (the straight portion of the fixed shape cannula 100 or a line parallel to the straight portion of the fixed shape cannula 100) form angle $\theta_1$ 425 (see FIG. 17). The fixed shape cannula 100 may be constructed in many ways, therefore angle $\theta_1$ 425 may have various values. In some embodiments, the angle $\theta_1$ 425 is between greater than about 0 to 180 degrees. In some embodiments, if the fixed shape cannula 100 bends through a larger angle, the value of angle $\theta_1$ 425 is greater.

In some embodiments, angle $\theta_1$ 425 is between about 1 to 10 degrees. In some embodiments, angle $\theta_1$ 425 is between about 10 to 20 degrees. In some embodiments, angle $\theta_1$ 425 is between about 20 to 30 degrees. In some embodiments, angle $\theta_1$ 425 is between about 30 to 40 degrees. In some embodiments, angle $\theta_1$ 425 is between about 40 to 50 degrees. In some embodiments, angle $\theta_1$ 425 is between about 50 to 60 degrees. In some embodiments, angle $\theta_1$ 425 is between about 60 to 70 degrees. In some embodiments, angle $\theta_1$ 425 is between about 70 to 80 degrees. In some embodiments, angle $\theta_1$ 425 is between about 80 to 90 degrees.

In some embodiments, angle $\theta$, 425 is between about 90 to 100 degrees. In some embodiments, angle $\theta_1$ 425 is between about 100 to 110 degrees. In some embodiments, angle $\theta_1$ 425 is between about 110 to 120 degrees. In some embodiments, angle $\theta_1$ 425 is between about 120 to 130 degrees. In some embodiments, angle $\theta_1$ 425 is between about 140 to 150 degrees. In some embodiments, angle $\theta_1$ 425 is between about 150 to 160 degrees. In some embodiments, angle $\theta_1$ 425 is between about 160 to 170 degrees. In some embodiments, angle $\theta_1$ 425 is between about 170 to 180 degrees.

Figure 1F:
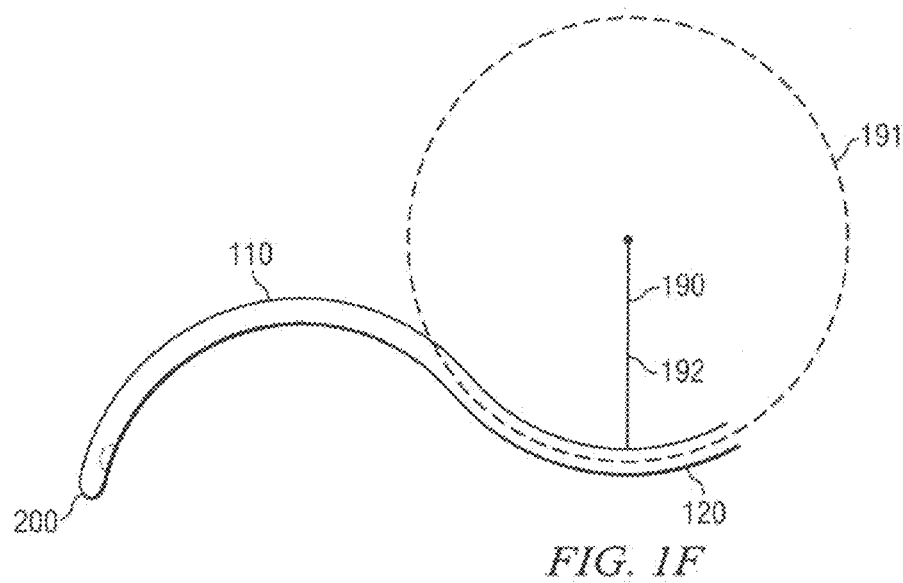

As shown in FIG. 1, FIG. 3, and FIG. 5, in some embodiments, the distal portion 110 and the proximal portion 120 lie in the same plane. In some embodiments, the proximal portion 120 is off at an angle from the distal portion 110, for example the proximal portion 120 is rotated or twisted with respect to the distal portion 110 such that the distal portion 110 and the proximal portion 120 lie in different planes. As shown in FIGS. 18A and 18B, in some embodiments, the distal portion 110 lies in plane $P_1$ 431 and the proximal portion 120 lies in plane $P_2$ 432. Plane $P_1$ 431 and plane $P_2$ 432 can be defined by their respective normal lines, for example $n_1$ for plane $P_1$ 431 and $n_2$ for plane $P_2$ 432. Given that the distal portion 110 can be represented as $n_1$ and the proximal portion 120 can be represented as $n_2$, in some embodiments, the distal portion 110 and proximal portion 120 can be rotated/twisted with respect to each other between about −90° and +90°. FIG. 18C illustrates several examples of spatial relationships between the proximal portion 120 $P_2$ 432 and distal portion 110 $P_1$ 431. The spatial relationships between the proximal portion 120 and distal portion 110 are not limited to the examples in FIG. 18.

In some embodiments, the region around the inflection point 130 is a gently curving bend such that a radiation source (e.g., a disk-shaped 405 RBS, a seed-shaped 400 RBS) may be pushed through the fixed shape cannula 100 (e.g., from the proximal portion 120 to the distal portion 110).

In some embodiments, the inflection point 130 of the fixed shape cannula 100 extends into a segment of straight fixed shape cannula between the distal portion 110 and the proximal portion 120. In some embodiments, the segment is between about 0 to 2 mm. In some embodiments, the segment is between about 2 to 5 mm. In some embodiments, the segment is between about 5 to 7 mm. In some embodiments, the segment is between about 7 to 10 mm. In some embodiments, the segment is more than about 10 mm.

The present invention also features a fixed shape cannula 100 with a fixed shape comprising a distal portion 110, a proximal portion 120, and an inflection point 130 connecting the distal portion 110 and the proximal portion 130, wherein the distal portion 110 and/or proximal portion 120 has a shape of an arc formed from a connection between a first point and a second point located on an ellipsoid 450, the ellipsoid 450 having an x-axis, a y-axis, and a z-axis (see FIG. 15). Ellipsoids can be defined by the equation below:

$$\frac{x^2}{a^2}+\frac{y^2}{b^2}+\frac{z^2}{c^2}=1$$

In some embodiments, the distal portion 110 has the shape of an arc derived from the ellipsoid 450 having the x-axis dimension "a," the y-axis dimension "b," and the z-axis dimension "c." In some embodiments, "a" is between about 0 to 1 meter, "b" is between about 0 to 1 meter, and "c" is between about 0 to 1 meter. For example, in some embodiments, "a" is between about 0 to 50 mm, "b" is between about 0 and 50 mm, and "c" is between about 0 and 50 mm.

In some embodiments, the ellipsoid 450 has a dimension "a", "b", and/or "c" between about 1 to 3 mm. In some embodiments, the ellipsoid 450 has a dimension "a", "b", and/or "c" between about 3 to 5 mm. In some embodiments, the ellipsoid 450 has a dimension "a", "b", and/or "c" between about 5 to 8 mm. In some embodiments, the ellipsoid 450 has a dimension "a", "b", and/or "c" between about 8 to 10 mm. In some embodiments, the ellipsoid 450 has a dimension "a", "b", and/or "c" between about 10 to 12 mm. In some embodiments, the ellipsoid 450 has a dimension "a", "b", and/or "c" between about 12 to 15 mm. In some embodiments, the ellipsoid 450 has a dimension "a", "b", and/or "c" between about 15 to 18 mm. In some embodiments, the ellipsoid 450 has a dimension "a", "b", and/or "c" between about 18 to 20 mm. In some embodiments, the ellipsoid 450 has a dimension "a", "b", and/or "c" between about 20 to 25 mm. In some embodiments, the ellipsoid 450 has a dimension "a", "b", and/or "c" greater than about 25 mm. In some embodiments, the ellipsoid 450 has dimensions "a" and "b" which are both between about 9 and 15 mm, for example about 12.1 mm. This ellipsoid 450 may be appropriate for designing a fixed shape cannula 100 for an emmetropic eye, wherein the eye is generally spherical. In some embodiments, the ellipsoid 450 has a dimension "a" between about 11 mm and 17 mm, for example about 14 mm, and a dimension "b" between about 9 mm and 15 mm, for example about 12.1 mm. This ellipsoid 450 may be appropriate for designing a fixed shape cannula 100 for a myopic eye, wherein the axial length is about 28 mm. In some embodiments, the ellipsoid 450 has a dimension "a" between about 7 to 13 mm, for example 10 mm, and a dimension "b" between about 9 to 15 mm, for example 12 mm. This ellipsoid 450 may be appropriate for a hyperopic eye, wherein the axial length is about 20 mm.

In some embodiments, the proximal portion 120 has the shape of an arc derived from the ellipsoid 450 having the x-axis dimension "d," the y-axis dimension "e," and the z-axis dimension "f." In some embodiments, "d" is between about 0 to 1 meter, "e" is between about 0 to 1 meter, and "f" is between about 0 to 1 meter. In some embodiments, "d" is between about 0 to 50 mm, "e" is between about 0 and 50 mm, and "f" is between about 0 and 50 mm.

In some embodiments, the ellipsoid 450 has a dimension "d", "e", and/or "f" between about 1 to 3 mm. In some embodiments, the ellipsoid 450 has a dimension "d", "e", and/or "f" between about 3 to 5 mm. In some embodiments, the ellipsoid 450 has a dimension "d", "e", and/or "f" between about 5 to 8 mm. In some embodiments, the ellipsoid 450 has a dimension "d", "e", and/or "f" between about 8 to 10 mm. In some embodiments, the ellipsoid 450 has a dimension "d", "e", and/or "f" between about 10 to 12 mm. In some embodiments, the ellipsoid 450 has a dimension "d", "e", and/or "f" between about 12 to 15 mm. In some embodiments, the ellipsoid 450 has a dimension "d", "e", and/or "f" between about 15 to 18 mm. In some embodiments, the ellipsoid 450 has a dimension "d", "e", and/or "f" between about 18 to 20 mm. In some embodiments, the ellipsoid 450 has a dimension "d", "e", and/or "f" between about 20 to 25 mm. In some embodiments, the ellipsoid 450 has a dimension "d", "e", and/or "f" between about 25 to 30 mm. In some embodiments, the ellipsoid 450 has a dimension "d", "e", and/or "f" between about 30 to 40 mm. In some embodiments, the ellipsoid 450 has a dimension "d", "e", and/or "f" between about 40 to 50 mm. In some embodiments, the ellipsoid 450 has a dimension "d", "e", and/or "f" greater than about 50 mm.

The ellipsoid 450 may be a sphere, wherein "a" is equal to "b", and "b" is equal to "c". The ellipsoid 450 may be a scalene ellipsoid (e.g., triaxial ellipsoid) wherein "a" is not equal to "b", "b" is not equal to "c", and "a" is not equal to "c".

In some embodiments, the ellipsoid 450 is an oblate ellipsoid wherein "a" is equal to "b", and both "a" and "b" are greater than "c". In some embodiments, the ellipsoid 450 is a prolate ellipsoid wherein "a" is equal to "b", and both "a" and "b" are less than "c".

In some embodiments, "a" is about equal to "b" (e.g., for an emmetropic eye). In some embodiments, "a" is not equal to "b" (e.g., for an emmetropic eye). In some embodiments, "b" is about equal to "c". In some embodiments, "b" is not equal to "c". In some embodiments, "a" is about equal to "c". In some embodiments, "a" is not equal to "c". In some embodiments, "d" is about equal to "e". In some embodiments, "d" is not equal to "e". In some embodiments, "e" is about equal to "f". In some embodiments, "e" is not equal to "f". In some embodiments, "d" is about equal to "f". In some embodiments, "d" is not equal to "f".

The dimensions of "a," "b," and "c" may vary. In FIG. 26, Table 1 lists several combinations of dimensions. The dimensions of "a," "b," and "c" are not limited to those listed in Table 1.

The dimensions of "d," "e," and "f" may vary. In FIG. 27, Table 2 lists several combinations of dimensions. The dimensions of "d," "e," and "f" are not limited to those listed in Table 2.

In some embodiments, the ellipsoid 450 is egg-shaped or a variation thereof.

The present invention also features a hollow fixed shape cannula 100 with a fixed shape comprising a distal portion 110 for placement around a portion of a globe of an eye, wherein the distal portion 110 has a radius of curvature 180 between about 9 to 15 mm and an arc length 185 between about 25 to 35 mm. The fixed shape cannula 100 comprises a proximal portion 120 having a radius of curvature 190 between about an inner cross-sectional radius 173 of the fixed shape cannula 100 (e.g., proximal portion 120 of fixed shape cannula 100) and about 1 meter and an inflection point 130, which is where the distal portion 110 and the proximal portion 120 connect with each other. In some embodiments, once the distal end (e.g., tip 200, distal region 112) of the distal portion 110 is positioned within the vicinity of the target, the proximal portion 120 is curved away from the visual axis 220 as to allow a user (e.g., physician) to have direct visual access in the eye.

In some embodiments, the present invention features a new cannula, said new cannula comprising: (a) a distal segment for placement around a portion of a globe of an eye; wherein the distal segment has a radius of curvature between about 9 to 15 mm and an arc length between about 25 to 35 mm; (b) a proximal segment having a radius of curvature between about an inner cross-sectional radius of said new cannula and about 1 meter; and (c) an inflection point which is where the distal segment and the proximal segments connect with each other; wherein an angle $\theta_1$ between a line $l_3$ tangent to the globe of the eye at the inflection point and the proximal segment is between greater than about 0 degrees to about 180 degrees. In some embodiments, the proximal end of the distal segment of said new cannula is tapered such the circumference of the proximal end is larger than the circumference of the distal end of the distal segment. In some embodiments, the distal segment of said new cannula has an arc length which is at least $\pi/4$ times the diameter of the globe of the eye under treatment. In some embodiments, the distal segment of said new cannula has sufficient arc length to penetrate the Tenon's capsule of the eye being treated and to extend around the outer diameter of said eye such that the distal end of the distal segment is positioned in the proximity of, and behind, the macula. In some embodiments, there is a means of advancing a RBS which is disposed within said new cannula and wherein said new cannula is for delivering the RBS to the back of the eye, said RBS having a rotationally symmetrical exposure surface capable of more than 1% of the total source radiation energy flux beyond a distance of 1 cm from the exposure surface.

Locator on the Cannula

In some embodiments, the cannula 100 comprises a locator 160. In some embodiments, a locator 160 is a physical mark (e.g., a visible mark and/or a physical protrusion) disposed on the cannula 100. In some embodiments, the locator 160 is for aligning the cannula 100 to facilitate the positioning of the distal portion 110 and/or tip 200 and/or RBS. In some embodiments, the locator 160 is disposed on the cannula 100 such that it will align with the limbus when the cannula 100 is in place (see for example FIG. 5, FIG. 6B). In some embodiments, the inflection point 130 located on cannula 100 may serve as a locator 160. For example, the user can position the inflection point 130 at the limbus as an indication that the tip 200 of the cannula 100 is approximately at the sclera 235 region that corresponds with the target, e.g., the macula.

Materials of Cannula

In some embodiments, the cannula 100 is constructed from a material comprising stainless steel, gold, platinum, titanium, the like, or a combination thereof. In some embodiments, the distal portion 110 and/or the proximal portion 120 are constructed from a material comprising surgical stainless steel. In some embodiments, the distal portion 110 and/or the proximal portion 120 are constructed from a material comprising other conventional materials such as Teflon, other metals, metal alloys, polyethylene, polypropylene, other conventional plastics, or combinations of the foregoing may also be used. For example, the distal portion 110 may be constructed from a material comprising a plastic. As another example, a part of the tip of the distal portion 110 may be constructed from a material comprising a plastic, and the remainder of the distal portion 110 and the proximal portion 120 may be constructed from a material comprising a metal. Without wishing to limit the present invention to any theory or mechanism, it is believed that the plastic has sufficient softness and/or flexibility to minimize the possibility of penetration of the sclera 235 or the Tenon's capsule 230 when the cannula 100 is inserted into the eye, as described herein. In addition, the length of the plastic portion of the distal portion 110, as well as the specific plastic, are preferably selected so that distal portion 110 maintains its radius of curvature 180 when the cannula 100 is inserted into the eye.

Handle, Extruding/Advancing Mechanism, Guide Wire

In some embodiments, the cannula 100 is functionally connected with a handle 140 (see FIG. 1, FIG. 4, FIG. 5). The handle 140 may be connected to the proximal portion 120 of the cannula 100. In some embodiments, the cannula 100 is free of a proximal portion 120, and a handle 140 is attached to the distal portion 110 at around the location where the proximal portion 120 normally connects to the distal portion 110 (e.g., the inflection point 130). Without wishing to limit the present invention to any theory or mechanism, it is believed that a handle 140 may provide the user with a better grip on the cannula 100 and allow for the user to more easily reach the posterior portion of the eye. In some embodiments, the handle 140 is attached to the cannula 100 by a frictional fit and/or conventional fastening means. In some embodiments, the handle 140 comprises a radiation shielding material. In some embodiments, the cannula 100 and handle 140 are preassembled as one piece. In some embodiments, the cannula 100 and handle 140 are assembled prior to inserting into the eye. In some embodiments, the cannula 100 and handle 140 are assembled after inserting the cannula 100 into posterior portion of the eye according to the present invention.

In some embodiments, the proximal portion 120 and/or handle 140 comprise one or more mechanisms for advancing the RBS (e.g., disk 405, seed-shaped RBS 400). Examples of such mechanisms include a slide mechanism, a dial mechanism, a thumb ring 810, a graduated dial 820, a slider 830, a fitting, a Toughy-Burst type fitting, the like, or a combination thereof (see FIG. 4).

In some embodiments, the cannula 100 further comprises a non-wire plunger 800 (see FIG. 4). Non-limiting examples of a non-wire plunger 800 include a solid stick, a piston, or a shaft. In some embodiments, the non-wire plunger 800 is constructed from a material comprising a plastic, a metal, a wood, the like, or a combination thereof. In some embodiments, the RBS is extended from and retracted into the cannula 100 with the non-wire plunger 800. In some embodiments, the non-wire plunger 800 is air tight. In some embodiments, the non-wire plunger 800 is not air tight. In some embodiments, the cannula 100 further comprises a spring.

In some embodiments, the cannula 100 comprises a guide wire 350 and/or a non-wire plunger 800 which function to advance the RBS. In some embodiments, the guide wire 350 and the non-wire plunger 800 are substituted by another mechanism which functions to advance the RBS. In some embodiments, the RBS may be advanced and retracted by hydrostatic pressure employing a fluid (e.g., a saline, an oil, or another type of fluid) using a syringe or other method. In some embodiments, the RBS is advanced and/or retracted by a pneumatic mechanism (e.g., air pressure) and retracted by a vacuum.

In some embodiments, the non-wire plunger 800 and/or the guide wire 350 comprise stainless steel. In some embodiments, the non-wire plunger 800 and/or the guide wire 350 are braided. In some embodiments, the guide wire 350 comprises a material that is the same material used to encase the RBS (e.g., disk 405, seed-shaped RBS 400) such as gold, silver stainless steel, titanium, platinum, the like, or a combination thereof. In some embodiments, the guide wire 350 comprises a material that is the same material that the radiation has been deposited into. In some embodiments, the RBS may be advanced and retracted by a Nitinol wire.

Orifice on the Cannula

In some embodiments, the cannula 100 comprises an orifice 500 located on an interior side (e.g., bottom) of the distal portion 110 (see FIG. 2). The orifice 500 may be for allowing the radiation to pass through the cannula 100 and reach the target. In some embodiments, the orifice 500 may be located on the tip 200 of the distal portion 110 or on other areas of the distal portion 110. In some embodiments, the distal portion 110 may have multiple orifices 500. In some embodiments, the orifice 500 has a round shape (e.g., circular). The orifice 500 may also have alternate shapes such as a square, an oval, a rectangle, an ellipse, or a triangle. In some embodiments, the orifice 500 has an area of about 0.01 mm$^2$ to about 0.1 mm$^2$. In some embodiments, the orifice 500 has an area of about 0.1 mm$^2$ to about 1.0 mm$^2$. In some embodiments, the orifice 500 has an area of about 1.0 mm$^2$ to about 10.0 mm$^2$.

In some embodiments, the size of the orifice 500 is smaller than the size of the RBS (e.g., disk 405, seed-shaped RBS 400). In some embodiments, the orifice 500 is circular and has a diameter of about 0.1 millimeters. In some embodiments, the orifice 500 is circular and has a diameter between about 0.01 millimeters and about 0.1 millimeters. In some embodiments, the orifice 500 is circular and has a diameter between about 0.1 millimeters and 1.0 millimeters. In some embodiments, the orifice 500 is circular and has a diameter between about 1.0 millimeters and 5.0 millimeters. In some embodiments, the orifice 500 is circular and has a diameter between about 5.0 millimeters and 10.0 millimeters.

In some embodiments, the orifice 500 is rectangular. In some embodiments, the orifice 500 is rectangular and is about 1.0 mm by 2.5 mm. In some embodiments, the orifice 500 is rectangular and is about 0.5 mm by 2.5 mm. In some embodiments, the orifice 500 is rectangular and is about 0.5 by 2.0 mm. In some embodiments, the orifice 500 is rectangular and is about 0.5 mm by 1.5 mm. In some embodiments, the orifice 500 is rectangular and is about 0.5 mm by 1.0 mm. In some embodiments, the orifice 500 is rectangular and is about 0.5 mm by 0.5 mm. In some embodiments, the orifice 500 is rectangular and is about 0.25 mm by 2.5 mm. In some embodiments, the orifice 500 is rectangular and is about 0.25 mm by 2.0 mm. In some embodiments, the orifice 500 is rectangular and is about 0.25 mm by 1.5 mm. In some embodiments, the orifice 500 is rectangular and is about 0.25 mm by 1.0 mm. In some embodiments, the orifice 500 is rectangular and is about 0.25 mm by 0.5 mm. In some embodiments, the orifice 500 is rectangular and is about 0.25 mm by 0.25 mm.

In some embodiments, the distal edge 520 of the orifice 500 is located between about 0.1 mm and 0.5 mm from the tip 200 of the distal portion 110. In some embodiments, the distal edge 520 of the orifice 500 is located between about 0.5 mm and 1.0 mm from the tip 200 of the distal portion 110. In some embodiments, the distal edge 520 of the orifice 500 is located between about 1.0 mm and 2.0 mm from the tip 200 of the distal portion 110. In some embodiments, the distal edge 520 of the orifice 500 is located between about 2.0 mm and 5.0 mm from the tip 200 of the distal portion 110. In some embodiments, the distal edge 520 of the orifice 500 is located between about 5.0 mm and 10.0 mm from the tip 200 of the distal portion 110. In some embodiments, the distal edge 520 of the orifice 500 is located between about 10.0 mm and 20.0 mm from the tip 200 of the distal portion 110.

Window on the Cannula

As used herein, the term "radiotransparent" refers to a material that absorbs less than about $10^{-1}$ or less than about $10^{-2}$ of the radiation flux. For example, a window 510 comprising a radiotransparent material includes a window 510 comprising a material that absorbs $10^{-5}$ of the radiation flux.

In some embodiments, the cannula 100 comprises a window 510. In some embodiments, the cannula 100 comprises an orifice 500 and a window 510, both generally disposed at the distal portion 110 of the cannula 100 (see FIG. 2). In some embodiments, the window 510 of the cannula 100 comprises a material that allows for more radiation transmission than other portions of the cannula 100. A window 510, for example, may comprise a lower density material or comprise a material having a lower atomic number. In some embodiments, the window 510 may comprise the same material as the cannula 100 but have a smaller wall thickness. In some embodiments, the window 510 comprises a radiotransparent material. In some embodiments, the window 510 comprises the same material as the cannula 100 and has the same wall thickness of the cannula 100. In some embodiments, the window 510 is the area of the cannula 100 from where the radiation is emitted.

In some embodiments, the cannula 100 comprises a window 510 located on an interior side (e.g., bottom) of the distal portion 110. The window 510 may be used to allow the radiation to pass through the cannula 100 and reach a target tissue. In some embodiments, the window 510 is a portion of the cannula 100 having a thickness that is less than the thickness of a cannula wall. In some embodiments, the window 510 is a portion of the cannula 100 having a thickness that is equal to the thickness of a cannula wall. In some embodiments, the window 510 is a portion of the cannula 100 having a thickness that is greater than the thickness of a cannula wall.

In some embodiments, the distal portion 110 may have multiple windows 510. In some embodiments, the window 510 has a round shape (e.g., circular). The window 510 may also have alternate shapes such as a square, an oval, a rectangle, or a triangle. In some embodiments, the window 510 has an area of about 0.01 mm$^2$ to about 0.1 mm$^2$. In some embodiments, the window 510 has an area of about 0.1 mm$^2$ to about 1.0 mm$^2$. In some embodiments, the window 510 has an area of about 1.0 mm$^2$ to about 10.0 mm$^2$. In some embodiments, the window 510 has an area of about 2.5 mm$^2$. In some embodiments, the window 510 has an area of greater than 2.5 mm$^2$, for example 50 mm$^2$ or 100 mm$^2$.

In some embodiments, the window 510 is rectangular. In some embodiments, the window 510 is rectangular and is about 1.0 mm by 2.5 mm. In some embodiments, the window 510 is rectangular and is about 0.5 mm by 2.5 mm. In some embodiments, the window 510 is rectangular and is about 0.5 by 2.0 mm. In some embodiments, the window 510 is rectangular and is about 0.5 by 1.5 mm. In some embodiments, the window 510 is rectangular and is about 0.5 by 1.0 mm. In some embodiments, the window 510 is rectangular and is about 0.5 mm by 0.5 mm. In some embodiments, the window 510 is rectangular and is about 0.25 mm by 2.5 mm. In some embodiments, the window 510 is rectangular and is about 0.25 mm by 2.0 mm. In some embodiments, the window 510 is rectangular and is about 0.25 mm by 1.5 mm. In some embodiments, the window 510 is rectangular and is about 0.25 mm by 1.0 mm. In some embodiments, the window 510 is rectangular and is about 0.25 mm by 0.5 mm. In some embodiments, the window 510 is rectangular and is about 0.25 mm by 0.25 mm. In some embodiments, the window 510 has an area of greater than 2.5 mm$^2$, for example, 50 mm$^2$, or 100 mm$^2$.

In some embodiments, the size of the window 510 is smaller than the size of the RBS (e.g., disk 405, seed-shaped RBS 400). In some embodiments, the size of the window 510 is larger than the size of the RBS. In some embodiments, the window 510 is elliptical and has axis dimensions of about 0.1 millimeters. In some embodiments, the window 510 is elliptical and has axis dimensions between about 0.1 millimeters and 1.0 millimeters. In some embodiments, the window 510 is elliptical and has axes dimensions between about 1.0 millimeters and 5.0 millimeters.

In some embodiments, the distal edge 520 of the window 510 is located between about 0.1 mm and 0.5 mm from the tip 200 of the distal portion 110. In some embodiments, the distal edge 520 of the window 510 is located between about 0.5 mm and 1.0 mm from the tip 200 of the distal portion 110. In some embodiments, the distal edge 520 of the window 510 is located between about 1.0 mm and 2.0 mm from the tip 200 of the distal portion 110. In some embodiments, the distal edge 520 of the window 510 is located between about 2.0 mm and 5.0 mm from the tip 200 of the distal portion 110. In some embodiments, the distal edge 520 of the window 510 is located between about 5.0 mm and 10.0 mm from the tip 200 of the distal portion 110. In some embodiments, the distal edge 520 of the window 510 is located between about 10.0 mm and 20.0 mm from the tip 200 of the distal portion 110.

Radiation Shielding

In some embodiments, the handle 140 and/or the proximal portion 120 and/or distal portion 110 of the cannula 100 is constructed from a material that can further shield the user from the RBS (e.g., disk 405). In some embodiments, the handle 140 and/or the proximal portion 120 comprises a material that is denser than the cannula 100. In some embodiments, the handle 140 and/or proximal portion 120 comprises a material that is thicker than the cannula 100. In some embodiments, the handle 140 and/or the proximal portion 120 comprise more layers of material than the cannula 100.

In some embodiments, a part of the distal portion 110 is constructed from a material that can further shield the user and/or the patient from the RBS. For example, the side of the distal portion 110 opposite the side that contacts the sclera 235 is constructed from a material that can further shield the patient from the RBS.

In some embodiments, the proximal portion 120 and/or the handle 140 comprises a container that provides radiation shielding, herein referred to as a radiation shielding "pig" 900 (see FIG. 4, FIG. 6). The radiation shielding pig 900 allows for the RBS (e.g., a disk 405, a seed-shaped RBS 400) to be stored in a retracted position. In some embodiments, the radiation shielding pig 900 provides for the storage of the RBS so that the device may be safely handled by the user.

In some embodiments, the proximal portion 120 and/or the handle 140 of the cannula 100 has a wall thickness designed to shield the RBS. In some embodiments, the proximal portion 120 and/or the handle 140 of the cannula 100 comprises stainless steel and has a thickness between about 1 mm to about 2 mm. In some embodiments, the proximal portion 120 and/or the handle 140 of the cannula 100 comprises stainless steel and has a thickness between about 2 mm to about 3 mm. In some embodiments, the proximal portion 120 and/or the handle 140 of the cannula 100 comprises stainless steel and has a thickness between about 3 mm to about 4 mm. In some embodiments, the proximal portion 120 and/or the handle 140 of the cannula comprises stainless steel and has a thickness between about 4 mm to about 5 mm. In some embodiments, the proximal portion 120 and/or the handle 140 of the cannula 100 comprises stainless steel and has a thickness between about 5 mm to about 10 mm.

In some embodiments, the proximal portion 120 and/or the handle 140 of the cannula 100 comprises a plurality of layers. In some embodiments, the proximal portion 120 and/or the handle 140 comprises a plurality of materials. In some embodiments, the plurality of materials comprises a tungsten alloy. Tungsten alloys are well known to those skilled in the art. For example, in some embodiments, the tungsten alloy has a high tungsten content and a low amount of NiFe, as is sometimes used in radiation shielding.

In some embodiments, shielding a beta isotope in a RBS may be difficult. In some embodiments, a material having a low atomic number (Z) may be used for shielding (e.g., polymethyl methacrylate). In some embodiments, one or more layers of material are used for shielding, wherein an inner layer comprises a material having a low atomic number (e.g., polymethyl methacrylate) and an outer layer comprises lead. In some embodiments, the proximal portion 120 and/or the handle 140 and/or the radiation shielding pig 900 comprises an inner layer surrounded by an outer layer. In some embodiments, the proximal portion 120 and/or the handle 140 and/or the radiation shielding pig 900 comprises an inner layer of polymethyl methacrylate (or other material) surrounded by an outer layer of lead (or other material).

In some embodiments, the inner layer is between about 0.1 mm to 0.25 mm. In some embodiments, the inner layer is between about 0.25 mm to 0.50 mm thick. In some embodiments, the inner layer is between about 0.5 to 1.0 mm thick. In some embodiments, the inner layer is between about 1.0 mm to 1.5 mm thick. In some embodiments, the inner layer is between about 1.5 mm and 2.0 mm thick. In some embodiments, the inner layer is between about 2.0 mm and 5.0 mm thick.

In some embodiments, the outer layer is between about 0.01 mm to 0.10 mm thick. In some embodiments, the outer layer is between about 0.10 mm to 0.15 mm thick. In some embodiments, the outer layer is between about 0.15 to 0.20 mm thick. In some embodiments, the outer layer is between about 0.20 mm to 0.50 mm thick. In some embodiments, the outer layer is between about 0.50 mm and 1.0 mm thick.

In some embodiments, the inner layer (e.g., polymethyl methacrylate or other material) is about 1.0 mm thick and the outer layer (e.g., lead or other material) is about 0.16 mm thick. In some embodiments, the inner layer (e.g., polymethyl methacrylate or other material) is between about 0.1 mm to 1.0 mm thick and the outer layer (e.g., lead or other material) is between about 0.01 mm to 0.10 mm thick. In some embodiments, the inner layer (e.g., polymethyl methacrylate or other material) is between about 0.1 mm to 1.0 mm thick and the outer layer (e.g., lead or other material) is between about 0.10 mm to 0.20 mm thick. In some embodiments, the inner layer (e.g., polymethyl methacrylate or other material) is between about 1.0 mm to 2.0 mm thick and the outer layer (e.g., lead or other material) is between about 0.15 mm to 0.50 mm thick. In some embodiments, the inner layer (e.g., polymethyl methacrylate or other material) is between about 2.0 mm to 5.0 mm thick and the outer layer (e.g., lead or other material) is between about 0.25 mm to 1.0 mm thick.

As shown in FIG. 1, FIG. 4, and FIG. 5, in some embodiments, the cannula 100 is terminated with a handle 140. In some embodiments, the proximal portion 120 further comprises a connector 150. In some embodiments, a handle 140 and/or a radiation shielding pig 900 may be fitted to the cannula 100 via the connector 150. In some embodiments, the radiation shielding pig 900 further comprises a plunger mechanism. In some embodiments, the cannula 100 is assembled prior to inserting it into a patient. In some embodiments, the cannula 100 is not assembled prior to insertion, for example the cannula 100 is assembled after the distal portion 110 is inserted it into a patient.

In some embodiments, the handle 140 and/or the pig 900 is attached to the cannula 100 after the cannula 100 is inserted via the subtenon approach. Without wishing to limit the present invention to any theory or mechanism, it is believed that attaching the handle 140 and/or the pig 900 to the cannula 100 after the cannula 100 has been inserted is advantageous because the handle 140 and/or the pig 900 would not interfere with the placement of the cannula 100. Additionally, the placement of the cannula 100 may be easier because the handle 140 and/or pig 900, which may be bulky, would not interfere with the physical features of the patient.

Tip of Cannula, Indentation Tip

The distal portion 110 comprises a tip 200. In some embodiments, the distal portion 110 comprises a tip 200 having a rounded shape (see FIG. 2). In some embodiments, the tip 200 is blunt-ended. In some embodiments, the tip 200 of the distal portion 110 is open. In some embodiments, the tip 200 of the distal portion 110 is closed. In some embodiments, the distal portion 110 has a tip 200 wherein the tip 200 is blunt so as to prevent damage to blood vessels and/or nerves in the periocular tissues and to pass smoothly over the sclera 235. In some embodiments, the tip 200 of the distal portion 110 further comprises a protuberance (e.g., indentation tip 600) projecting from the cannula 100 so as to indent the sclera 235 and functions as a visual aid to guide the distal portion 110 of the cannula 100 to the correct position at the back of the eye (for example, see FIG. 2). In some embodiments, the indentation of the sclera 235 may be observed in the posterior pole of the eye by viewing through the pupil.

In some embodiments, the protuberance (e.g., indentation tip 600) is over the RBS (see FIG. 2). In some embodiments, the combined thickness of the cannula wall and the indentation tip 600 (which may both comprise stainless steel) is about 0.33 mm thick and the RBS thus creates x-rays that deposit more than 1% of the energy radiated by the RBS beyond 1 cm.

In some embodiments, the protuberance (e.g., indentation tip 600) is between about 0.01 mm and 0.10 mm thick. In some embodiments, the protuberance (e.g., indentation tip 600) is between about 0.10 mm and 0.20 mm thick. In some embodiments, the indentation tip 600 is between about 0.20 mm and 0.33 mm thick. In some embodiments, the indentation tip 600 is between about 0.33 and 0.50 mm thick. In some embodiments, the indentation tip 600 is between about 0.50 mm and 0.75 mm thick. In some embodiments, the indentation tip 600 is between about 0.75 mm and 1.0 mm thick. In some embodiments, the indentation tip 600 is between about 1.0 mm and 5.0 mm thick.

Light Source on the Cannula

In some embodiments, the distal portion 110 comprises a tip 200 and a light source 610 disposed at the tip 200 (see FIG. 2). In some embodiments, the distal portion 110 comprises a light source 610 that runs a portion of the length of the distal portion 110. In some embodiments, the cannula 100 comprises a light source 610 that runs the length of the cannula 100. Without wishing to limit the present invention to any theory or mechanism, it is believed that a light source 610 that runs the length of the cannula 100 may be advantageous because illuminating the entire cannula 100 may assist the user (e.g., physician, surgeon) in guiding the placement of the cannula 100 and/or observing the physical structures in the area of placement.

In some embodiments, the light source 610 comprises a light-emitting diode (LED) at the tip 200 of the cannula 100. The LED light may be seen through transillumination and may help guide the surgeon to the correct positioning of the cannula 100. In some embodiments, the light source 610 is directed through the cannula 100 by fiberoptics. In some embodiments, a light source 610, an indentation tip 600, and a window 510 or an orifice 500 are coaxial.

In some embodiments, the light source 610 illuminates the target area. In some embodiments, the light source 610 illuminates a portion of the target area. In some embodiments, the light source 610 illuminates the target area and a non-target area. As used herein, a "target area" is the area receiving about 100% of the intended therapeutic radiation dose. In some embodiments, the cannula 100 comprises a light source 610 that illuminates more than the targeted radiation zone. Without wishing to limit the present invention to any theory or mechanism, it is believed that a light 610 is advantageous because a light 610 may create a diffuse illumination through lateral scattering that may be used in lieu of an indirect ophthalmoscope light. The light from the light source 610 may extend beyond the lesion to make reference points (e.g., optic nerve, fovea, vessels) visible which may help orient the user (e.g., physician, surgeon).

In some embodiments, a part of or the entire cannula 100 glows. This may allow the user (e.g., physician, surgeon) to observe the insertion of the cannula 100 and/or observe the target. In some embodiments, the cannula 100 is not illuminated in the area that is to be placed over the target (e.g., everything but the target is illuminated).

Radionuclide Brachytherapy Source

According to the Federal Code of Regulations, a radionuclide brachytherapy source (RBS) comprises a radionuclide encased in an encapsulation layer. For example, the Federal Code of Regulations defines a radionuclide brachytherapy source as follows:

"A radionuclide brachytherapy source is a device that consists of a radionuclide which may be enclosed in a sealed container made of gold, titanium, stainless steel, or platinum and intended for medical purposes to be placed onto a body surface or into a body cavity or tissue as a source of nuclear radiation for therapy."

The present invention features a novel radionuclide brachytherapy source ("RBS"). The RBS of the present invention is constructed in a manner that is consistent with the Federal Code of Regulations, but is not limited to the terms mentioned in the Code. For example, the RBS of the present invention may optionally further comprise a substrate (discussed below). Also, for example, in addition to being enclosed by the mentioned "gold, titanium, stainless steel, or platinum", in some embodiments the radionuclide (isotope) of the present invention may be enclosed by a combination of one or more of "gold, titanium, stainless steel, or platinum". In some embodiments, the radionuclide (isotope) of the present invention may be enclosed by one or more layers of an inert material comprising silver, gold, titanium, stainless steel, platinum, tin, zinc, nickel, copper, other metals, ceramics, or a combination of these.

The RBS may be constructed in a number of ways, having a variety of designs and/or shapes and/or distributions of radiation. In some embodiments, the RBS comprises a substrate 361, a radioactive isotope 362 (e.g., Strontium-90), and an encapsulation. FIG. 14E. In some embodiments, the isotope 362 is coated on the substrate 361, and both the substrate 361 and isotope 362 are further coated with the encapsulation. In some embodiments, the radioactive isotope 362 is embedded in the substrate 361. In some embodiments, the radioactive isotope 362 is part of the substrate 361 matrix. In some embodiments, the encapsulation may be coated onto the isotope 362, and optionally, a portion of the substrate 361. In some embodiments, the encapsulation is coated around the entire substrate 361 and the isotope 362. In some embodiments, the encapsulation encloses the isotope 362. In some embodiments, the encapsulation encloses the entire substrate 361 and the isotope 362. In some embodiments, the radioactive isotope 362 is an independent piece and is sandwiched between the encapsulation and the substrate 361.

The RBS is designed to provide a controlled projection of radiation in a rotationally symmetrical (e.g., circularly symmetrical) shape onto the target. In some embodiments, the RBS has an exposure surface that has a rotationally symmetrical shape to provide for the projection of a rotationally symmetrical irradiation onto the target.

A shape having n sides is considered to have n-fold rotational symmetry if n rotations each of a magnitude of 360°/n produce an identical figure. In some embodiments, shapes described herein as being rotationally symmetrical are shapes having n-fold rotational symmetry, wherein n is a positive integer of 3 or greater.

In some embodiments, the rotationally symmetrical shape has at least 5-fold rotational symmetry (n=5). In some embodiments, the rotationally symmetrical shape has at least 6-fold rotational symmetry (n=6). In some embodiments, the rotationally symmetrical shape has at least 7-fold rotational symmetry (n=7). In some embodiments, the rotationally symmetrical shape has at least 8-fold rotational symmetry (n=8). In some embodiments, the rotationally symmetrical shape has at least 9-fold rotational symmetry (n=9). In some embodiments, the rotationally symmetrical shape has at least 10-fold rotational symmetry (n=10). In some embodiments, the rotationally symmetrical shape has infinite-fold rotational symmetry (n=∞). Examples of rotationally symmetrical shapes such as a circle, a square, an equilateral triangle, a hexagon, an octagon, a six-pointed star, and a twelve-pointed star can be found in FIG. 14F.

Without wishing to limit the present invention to any theory or mechanism, it is believed that the rotationally symmetrical geometry provides a fast fall off at the target periphery. In some embodiments, the rotationally symmetrical geometry provides a uniform fall off of radiation at the target periphery. In some embodiments, the fast fall off of radiation at the target periphery reduces the volume and/or area irradiated.

Rotationally Symmetrical Exposure Surface Controlled by the Shape of the Substrate In some embodiments, a surface on the substrate 361 is shaped in a manner to provide a controlled projection of radiation in a rotationally symmetrical shape onto the target. For example, in some embodiments, the bottom surface 363 of the substrate 361 is rotationally symmetrical, e.g., circular, hexagonal, octagonal, decagonal, and/or the like. When the radioactive isotope 362 is coated onto such rotationally symmetrical bottom surface 363 of the substrate 362 a rotationally symmetrical exposure surface is created.

In some embodiments, the substrate 361 is a disk 405, for example a disk 405 having a height 406 and a diameter 407 (see FIG. 14). In some embodiments, the height 406 of the disk 405 is between about 0.1 mm and 10 mm. For example, in some embodiments, the height 406 of the disk 405 is between about 0.1 to 0.2 mm. In some embodiments, the height 406 of the disk 405 is between about 0.2 to 2 mm, such as 1.5 mm. In some embodiments, the height 406 of the disk 405 is between about 2 to 5 mm. In some embodiments, the height 406 of the disk 405 is between about 5 to 10 mm. In some embodiments, the diameter 407 of the disk 405 is between about 0.1 to 0.5 mm. In some embodiments, the diameter 407 of the disk is between about 0.5 to 10 mm. For example, in some embodiments, the diameter 407 of the disk 405 is between about 0.5 to 2.5 mm, such as 2 mm. In some embodiments, the diameter 407 of the disk 405 is between about 2.5 to 5 mm. In some embodiments, the diameter 407 of the disk 405 is between about 5 to 10 mm. In some embodiments, the diameter 407 of the disk 405 is between about 10 to 20 mm.

The substrate 361 may be constructed from a variety of materials. For example, in some embodiments the substrate 361 is constructed from a material comprising, a silver, an aluminum, a stainless steel, tungsten, nickel, tin, zirconium, zinc, copper, a metallic material, a ceramic material, a ceramic matrix, the like, or a combination thereof. In some embodiments, the substrate 361 functions to shield a portion of the radiation emitted from the isotope 362. For example, in some embodiments, the substrate 361 has thickness such that the radiation from the isotope 362 cannot pass through the substrate 361. In some embodiments, the density times the thickness of the substrate 361 is between about 0.01 g/cm$^2$ to 10 g/cm$^2$.

The substrate 361 may be constructed in a variety of shapes. For example, the shape may include but is not limited to a cube, a sphere, a cylinder, a rectangular prism, a triangular prism, a pyramid, a cone, a truncated cone, a hemisphere, an ellipsoid, an irregular shape, the like, or a combination of shapes. As shown in FIG. 14, in some embodiments, the substrate 361 may have a generally rectangular side cross section. In some embodiments, the substrate 361 may have a generally triangular or trapezoidal side cross section. In some embodiments, the substrate 361 may have generally circular/oval side cross section. The side cross section of the substrate 361 may be a combination of various geometrical and/or irregular shapes.

Rotationally Symmetrical Exposure Surface Controlled by the Shape of the Isotope In some embodiments, the isotope 362 is coated on the entire substrate 361. In some embodiments, the isotope 362 is coated or embedded on a portion of the substrate 361 (e.g., on the bottom surface 363 of the substrate 361) in various shapes. For example, the coating of the isotope 362 on the substrate 361 may be in the shape of a rotationally symmetrical shape, e.g., a circle, a hexagon, an octagon, a decagon, or the like. The rotationally symmetrical shape of the isotope 362 coating on the bottom surface 363 of the substrate 361 provides for the rotationally symmetrical exposure surface, which results in a controlled projection of radiation in a rotationally symmetrical shape onto the target.

Rotationally Symmetrical Exposure Surface Controlled by the Shape of the Encapsulation In some embodiments, the encapsulation is constructed to provide a rotationally symmetrical exposure surface for a controlled projection of radiation having a rotationally symmetrical shape on the target. In some embodiments, the encapsulation has variable thickness so that it shields substantially all of the radiation in some portions and transmits substantially all of the radiation in other portions. For example, in one embodiment, the density times the thickness of the encapsulation is 1 g/cm$^2$ at distances greater than 1 mm from the center of the radioactive portion of the source and the density times the thickness of the encapsulation is 0.01 g/cm$^2$ at distances less than 1 mm from the center of the radioactive portion of the source. For a Sr-90 source, this encapsulation would block substantially all of the radiation emitted more than 1 mm from the center of the radioactive portion of the source, yet permit substantially all of the radiation emitted within 1 mm of the center of the radioactive portion of the source to pass through. In some embodiments, the thickness of the encapsulation varies between 0.001 g/cm$^2$ and 10 g/cm$^2$. In some embodiments, rotationally symmetric shapes of the high and low density regions as described above are used.

The encapsulation may be constructed from a variety of materials, for example from one or more layers of an inert material comprising a steel, a silver, a gold, a titanium, a platinum, another bio-compatible material, the like, or a combination thereof. In some embodiments, the encapsulation is about 0.01 mm thick. In some embodiments, the encapsulation is between about 0.01 to 0.10 mm thick. In some embodiments, the encapsulation is between about 0.10 to 0.50 mm thick. In some embodiments, the encapsulation is between about 0.50 to 1.0 mm thick. In some embodiments, the encapsulation is between about 1.0 to 2.0 mm thick. In some embodiments, the encapsulation is more than about 2.0 mm thick, for example about 3, mm, about 4 mm, or about 5 mm thick. In some embodiments, the encapsulation is more than about 5 mm thick, for example, 6 mm, 7 mm, 8 mm, 9 mm, or 10 mm thick.

Rotationally Symmetrical Exposure Surface Controlled by Other Components

In some embodiments, a radiation-shaper 366 can provide a controlled projection of radiation in a rotationally symmetrical shape onto the target. (FIG. 14G). A radiation-shaper 366 comprises a radio-opaque portion and a substantially radioactive transparent portion (hereinafter "window 364"). In some embodiments, the radiation shaper 366 is placed under the RBS. The radiation from the portion of the RBS that overlaps the window 364 is emitted through the window 364 toward the target, and the radiation from the portion that does not overlap the window 364 is blocked by the radio-opaque portion from reaching the target. Thus, a window 364 having a rotationally symmetrical shape will allow for a projection of a rotationally symmetrical irradiation of the target.

In some embodiments, the window 510 (or orifice 500) of the cannula 100 may be the window 364 of the radiation shaper 366 to provide a controlled projection of radiation in a rotationally symmetrical shape onto the target. For example, in some embodiments, the window 510 is circular.

As discussed, a controlled projection of radiation in a rotationally symmetrical shape onto the target allows for a fast fall off at the edge of the target. Also intended to be within the scope of the present invention are the various combinations of arrangements of the components of the RBS and/or cannula 100 to produce a controlled projection of radiation in a rotationally symmetrical shape onto a target. Based on the disclosures herein, one of ordinary skill would know how to develop these various combinations to produce a controlled projection of radiation in a rotationally symmetrical shape onto the target allows for a fast fall off at the edge of the target. Fast fall off at the edge of the target may also be enhanced by recessing the RBS in a well having deep radio opaque walls. For example, FIG. 21 shows an RBS recessed in a well with deep walls, where the walls can enhance and even faster fall off of radiation at the target edge.

Isotopes & Radioactivity

Various isotopes may be employed within the scope of the present invention. Beta emitters such as phosphorus 32 and strontium 90 were previously identified as being useful radioactive isotopes because they are beta emitters that have limited penetration and are easily shielded. In some embodiments, the isotope 362 comprises phosphorus 32 (P-32), strontium-90 (Sr-90), ruthenium 106 (Ru-106), yttrium 90 (Y-90), the like, or a combination thereof.

Although they are distinctly different from beta emitters, in some embodiments, the RBS may comprise an isotope 362 such as a gamma emitter and/or an alpha emitter. For example, in some embodiments, the isotope 362 comprises iodine 125 (I-125), palladium 103 (Pd-103), cesium 131 (Cs-131), cesium 137 (Cs-137), cobalt 60 (co-60), the like, or a combination thereof. In some embodiments, the RBS comprises a combination of various types of isotopes 362. For example, in some embodiments, the isotope 362 comprises a combination of Sr-90 and P-32. In some embodiments, the isotope 362 comprises a combination of Sr-90 and Y-90.

To achieve a particular dose rate at the target, the activity of the isotope that is to be used is determined for a given distance between the isotope and the target. For example, if the radiation source is a strontium-yittrium-90 titanate internally contained in a silver-clad matrix forming a disk about 4 mm in diameter and having a height of about 0.06 mm, sealed in titanium that is about 0.8 mm thick on one flat surface of the disk and around the circumference and is about 0.1 mm thick on the opposite flat surface of the disk (target side of the disk), the target is at a depth of about 1.5 mm (in tissue) and the desired dose rate is about 24 Gy/min at the target, an activity of about 100 mCi may be used. Or, if all aspects of the source are kept the same except that the diameter of the strontium-yittrium-90 titanate internally contained in a silver-clad matrix disk is about 3 mm in diameter, the target is at a depth of about 2.0 mm (in tissue) and the desired dose rate is about 18 Gy/min at the target, an activity of about 150 mCi may be used. Or, if all aspects of the source are kept the same except that the diameter of the strontium-yittrium-90 titanate internally contained in a silver-clad matrix disk is about 3 mm in diameter, the target is at a depth of about 0.5 mm (in tissue) and the desired dose rate is about 15 Gy/min at the target, an activity of about 33 mCi may be used. Or, if all aspects of the source are kept the same except that the diameter of the strontium-yittrium-90 titanate internally contained in a silver-clad matrix disk is about 2 mm in diameter, the target is at a depth of about 5.0 mm (in tissue) and the desired dose rate is about 30 Gy/min at the target, an activity of about 7100 mCi may be used.

In some embodiments, the isotope has about 5 to 20 mCi, for example, 10 mCi.

In some embodiments, to achieve a particular dose rate at the target, the radioactivity of the isotope 362 that is to be used is determined for a given distance between the isotope 362 and the target. For example, if the Sr-90 isotope 362 is about 5 mm from the target (in tissue) and the desired dose rate is about 20 Gy/min at the target, a Sr-90 isotope 362 having a radioactivity of about 5,000 mCi may be used. Or, if the P-32 isotope 362 is about 2 mm from the target and the desired dose rate is about 25 Gy/min at the target, a P-32 isotope 362 having a radioactivity of about 333 mCi may be used.

In some embodiments, the isotope 362 has an activity of between about 0.5 to 5 mCi. In some embodiments, the isotope 362 has an activity of between about 5 to 10 mCi. In some embodiments, the isotope 362 has an activity of between about 10 to 50 mCi. In some embodiments, the isotope 362 has an activity of between about 50 to 100 mCi. In some embodiments, the isotope 362 has an activity of between about 100 to 500 mCi. In some embodiments, the isotope 362 has an activity of between about 500 to 1,000 mCi. In some embodiments, the isotope has an activity of between about 1,000 to 5,000 mCi. In some embodiments, the isotope has an activity of between about 5,000 to 10,000 mCi. In some embodiments, the isotope 362 has an activity of more than about 10,000 mCi.

Guide & Memory Wire

In some embodiments, the RBS (e.g., substrate and/or encapsulation) is attached to the guide wire 350 or ribbon that runs through the cannula. In some embodiments, the attachment of the substrate 361 and/or the encapsulation to the guide wire 350 may be achieved using a variety of methods. In some embodiments, the substrate 361 and/or encapsulation is attached by welding. In some embodiments, the substrate 361 and/or encapsulation is attached to the guide wire 350 by glue. In some embodiments, the substrate 361 and/or encapsulation is attached to the guide wire 350 (or ribbon) by being enveloped in a plastic sleeve having an extension which forms a plastic guide wire 350. In some embodiments, this may be achieved using a method such as heat shrink tubing. In some embodiments, the substrate 361 and/or encapsulation is coated onto the guide wire 350 or the ribbon that runs through the cannula.

In some embodiments, the RBS is in the form of a deployable wafer. In some embodiments, the wafer is in the shape of a cylinder, an ellipse, or the like. In some embodiments, the wafer comprises nickel titanium (NiTi) either doped with or surface coated with a radioisotope that opens up when deployed. In some embodiments, the wafer is coated with a bio-inert material if it is to be left in place for an extended period of time.

In some embodiments, the memory wire 300 comprises the RBS. In some embodiments, the memory wire 300 functions like a disk 405 or seed-shaped RBS 400. The seed-shaped RBS 400 may have a spherical or ellipsoidal shape. The shape of the seed-shaped RBS 400 is not limited to the aforementioned shapes. In some embodiments, the shape of the seed-shaped RBS 400 is determined by dimensions so as to maximize the area and/or the volume that can pass through a cannula 100 per the cannula 100 description. For example, in some embodiments, the RBS is in the shape of a curved cylinder. In some embodiments, the curved cylinder has a rounded distal end and a rounded proximal end so to further accommodate the curvature of the cannula 100.

In some embodiments, the RBS is for inserting into a cannula 100. In some embodiments, the RBS is designed to traverse a length of the cannula 100. In some embodiments, more than one RBS is used to deliver radiation to a target. For example, in some embodiments, two disks 405 may be used inside the cannula 100.

Construction of RBS Wherein More than 1% of the Total Source Radiation Energy Flux Extends Beyond a Distance of 1 CM Without wishing to limit the present invention to any theory or mechanism, it is believed that an effective design for a medical device for treating wet age-related macular degeneration should have a radiation dose distribution such that greater than 1% of the total source radiation energy flux (e.g., total radiation energy flux at the source center along the line $l_R$) is transmitted to greater than or equal to 1 cm distance from the RBS (along the line $l_R$).

In some embodiments, the present invention has a RBS that deposits less than about 99% (e.g., 98%, 97%, etc.) of its total source radiation energy flux at distance of 1 cm or less from the RBS.

In some embodiments, the present invention has a RBS that deposits more than 1% (e.g., 2%, 3%, 4% etc.) of its total source radiation energy flux at distance of 1 cm or more from the RBS. In some embodiments, the present invention has a RBS that deposits between 1% to 15% of its total source radiation energy flux at distance of 1 cm or more from the RBS.

In some embodiments, the interaction of the isotope radiation (e.g., beta radiation) with the encapsulation (e.g., gold, titanium, stainless steel, platinum) converts some of the beta radiation energy to an emission of bremsstrahlung x-rays. These x-rays may contribute to the entire radiotherapy dose both in the prescribed target area and also penetrate further than beta radiation. Thus such a device as constructed with the aforementioned desirable attributes with a primary beta source will produce a radiation pattern in which 1% or greater of all radiation from the source is absorbed at a distance greater than 1 cm (e.g., the radiation energy flux at a distance of 1 cm away from the center of the target is greater than 1% of the total source radiation energy flux). See Table 3. In some embodiments, the present invention features a device wherein the RBS comprises an isotope, wherein the isotope comprises a beta radiation isotope, wherein about 1% of the total source radiation energy flux falls at a distance greater than 1 cm from the center of the target.

Without wishing to limit the present invention to any theory or mechanism, it is believed that it is desirable to construct the RBS as described in the present invention for ease of manufacturing and so it is inert to the body (due to encasing the RBS in a bio-compatible material). A RBS that is constructed in this manner may produce a radiation pattern comprising beta rays, x-rays, or both beta rays and x-rays, such that greater than 1% of the total source radiation energy flux will extend a distance greater that about 1 cm.

In FIG. 28, Table 3 is a listing for non-limiting examples of such Sr-90-constructed radioactive seeds.

In some embodiments, the RBS is in the form of a deployable wafer. In some embodiments, the wafer is in the shape of a cylinder, an ellipse, or the like. In some embodiments, the wafer comprises a nickel titanium (NiTi) substrate, either doped with or surface coated with an isotope 362 and then encapsulated, that opens up when deployed. In some embodiments, the wafer is encapsulated with a bio-inert material if it is to be left in place for an extended period of time.

In some embodiments, the RBS is for inserting into a cannula 100. In some embodiments, the RBS is designed to traverse a length of the cannula 100. In some embodiments, more than one RBS is used to deliver radiation to a target. For example, in some embodiments, two radioactive disks 405 or seed-shaped RBSs 400 are inserted into the cannula 100.

The Memory Wire

In some embodiments, the cannula 100 of the present invention comprises a guide wire 350 inserted within the cannula 100, whereby the guide wire 350 functions to push a RBS toward the tip 200 of the distal portion 110.

In some embodiments, the cannula 100 comprises a memory wire 300 (FIG. 2). In some embodiments, the cannula 100 comprises a guide wire 350 and a memory wire 300, wherein the guide wire 350 is connected to the memory wire 300. In some embodiments, the cannula 100 comprises a guide wire 350 and a memory wire 300, wherein the guide wire 350 and the memory wire 300 are the same wire. In some embodiments, the memory wire 300 may be extended from or retracted into the cannula 100 as the guide wire 350 is advanced or retracted, respectively.

In some embodiments, the memory wire 300 assumes a shape once it is deployed to the tip 200 of the cannula 100. In some embodiments, the memory wire 300 comprises a material that can take a desirable shape for use in delivering the radiation to a posterior portion of the eye. It will be understood by persons having skill in the art that many shapes of memory wires may be utilized to provide a shape consistent with that required or desired for treatment. In some embodiments, the memory wire 300 is in the shape of a spiral, a flat spiral 310, a ribbon, the like, or a combination thereof (FIG. 2). In some embodiments, the desirable shape of the memory wire 300 for delivering radiation may not allow for the memory wire 300 to be inserted into the cannula 100. Therefore, in some embodiments, the memory wire 300 is capable of being straightened so that it may be inserted into the cannula 100. In some embodiments, the memory wire 300 may form a shape (e.g., a spiral) when extended from the cannula 100. In some embodiments, the memory wire 300 having a shape (e.g., a flat spiral 310) may be straightened upon being retracted into the cannula 100. In some embodiments, the memory wire 300 extends from the tip 200 of the distal portion 110 of the cannula 100.

In some embodiments, the memory wire 300 comprises an alloy of nickel-titanium (NiTi). However, it will be understood by persons having skill in the art that any metal, or alloy, or other material such as spring steel, shape memory nickel-titanium, super-elastic nickel-titanium, plastics and other metals and the like, can be used to create the memory wire 300.

In some embodiments, the memory wire 300 comprises the RBS (e.g., substrate 261, isotope 362 and/or encapsulation). In some embodiments, the memory wire 300 has the isotope 362 deposited on it and is further encapsulated, thus the memory wire 300 comprises the RBS. In some embodiments, the distal end 320 of the memory wire 300 comprises the RBS (e.g., isotope 362 and encapsulation), for example the distal end 320 is coated with an isotope and further encapsulated. In some embodiments, the distal end 320 of the memory wire 300 comprises the RBS and the remaining portion of the memory wire 300 and/or the guide wire 350 may act to shield neighboring areas from the radiation. In some embodiments, the RBS and/or isotope 362 are applied to the memory wire 300 as a thin coating. In some embodiments, the RBS is applied to the memory wire 300 as solid pieces.

In some embodiments, the memory wire 300 functions like a disk 405 or seed-shaped RBS 400. The seed-shaped RBS 400 may have a spherical shape, cylindrical shape, or an ellipsoidal shape. The shape of the seed 400 is not limited to the aforementioned shapes. In some embodiments, the shape of the seed 400 is determined by dimensions so as to maximize the area and/or the volume that can pass through a cannula 100 per the cannula 100 description. For example, in some embodiments, the RBS is in the shape of a curved cylinder. In some embodiments, the curved cylinder has a rounded distal end and a rounded proximal end so to further accommodate the curvature of the cannula 100.

In some embodiments, the memory wire 300 is advanced toward the tip 200 of the cannula 100, allowing the memory shape to form. Without wishing to limit the present invention to any theory or mechanism, it is believed that the memory shape is advantageous because when it is formed, it concentrates the RBS in the desired shape. Further, various shapes may be used to achieve a certain concentration of radiation and/or to achieve a certain area of exposure. The shape may be customized to achieve particular desired results. For example, a low radiation intensity may be delivered when the wire exposed at the distal end is substantially straight, and a higher radiation intensity may be delivered with the wire exposed at the distal end is coiled up where there is more bundling of the radiation at the area.

In some embodiments, the memory wire 300 is a flat wire similar to a ribbon. In some embodiments, the ribbon may be coated (e.g., with an isotope and encapsulation) on only one edge, and when the ribbon is coiled, the edge that is coated with radiation material will concentrate the RBS, and the other edge not comprising radiation material may act as a shield.

In some embodiments, the RBS (e.g., substrate 361 and/or encapsulation and isotope 362) is attached to the guide wire 350. In some embodiments, the attachment of the substrate 361 and/or the encapsulation to the guide wire 350 may be achieved using a variety of methods. In some embodiments, the substrate 361 and/or encapsulation is attached by welding. In some embodiments, the substrate 361 and/or encapsulation is attached to the guide wire 350 by glue. In some embodiments, the substrate 361 and/or encapsulation is attached to the guide wire 350 by being enveloped in a plastic sleeve having an extension, which forms a plastic guide wire 350. In some embodiments, this may be achieved using a method such as heat shrink tubing.

Distal Chamber and Balloon

In some embodiments, the cannula 100 comprises a distal chamber 210 disposed at the end of the distal portion 110 (see FIG. 2). The distal chamber 210 allows a memory wire 300 to coil in a protected environment. In some embodiments, the distal chamber 210 is in the shape of a disc. In some embodiments, the distal chamber 210 is in the shape of a two-dimensional tear drop.

In some embodiments, the distal chamber 210 is rounded at the tip and has a width that is about the same as the width of the cannula 100. In some embodiments, the distal chamber 210 is hollow. The distal chamber 210 allows a memory wire 300 or a RBS (e.g., disk 405, seed-shaped RBS 400) to be inserted into it. In some embodiments, the memory wire 300 curls into a coil in the distal chamber 210. In some embodiments, coiling of the memory wire 300 inside the distal chamber 210 concentrates the RBS. Without wishing to limit the present invention to any theory or mechanism, it is believed that concentrating the RBS allows for a faster procedure. Additionally, this may allow for use of a lower activity RBS. In some embodiments, the distal chamber 210 keeps the memory wire 300 enclosed in a controlled space, allowing the memory wire 300 to coil into the distal chamber 210 and be retracted into the cannula 100 without concern of the memory wire 300 breaking off or becoming trapped in surrounding structures. In some embodiments, the distal chamber 210 is oriented to lay flat against the back of the eye (e.g., against the sclera).

In some embodiments, the distal chamber 210 further comprises a protuberance (e.g., distal chamber indentation tip) projecting from the distal chamber 210 so as to indent the sclera and functions to guide the distal chamber 210 to the correct position at the back of the eye. In some embodiments, the distal chamber indentation tip is disposed on the front of the distal chamber 210, the front being the part that has contact with the patient's eye. In some embodiments, the distal chamber indentation trip allows a physician to identify the location of the tip 200 of the cannula 100 over the target area. In some embodiments, the distal chamber 210 further comprises a light source 610.

In some embodiments, the distal chamber 210 comprises a metal, a plastic, the like, or a combination thereof. In some embodiments, the distal chamber 210 comprises one or more layers of metals and/or alloys (e.g., a gold, a stainless steel). In some embodiments, the distal chamber 210 comprises a material that does not shield the RBS. In some embodiments, the distal chamber 210 comprises an orifice 500 and/or a window 510 disposed on the front of the distal chamber 210. In some embodiments, the distal chamber 210 further comprises a radiation shield disposed on the back of the distal chamber 210 and/or a side of the distal chamber 210. Without wishing to limit the present invention to any theory or mechanism, it is believed that a distal chamber 210 comprising a radiation shield disposed on the back and/or a side of the distal chamber 210 is advantageous because it would prevent the radiation from being directed to an area other than the target area (e.g., the patient's optic nerve).

In some embodiments, the cannula 100 comprises an expandable tip (e.g., a balloon). In some embodiments, the expandable tip may be expanded using a gas or a liquid, for example balanced salt solution (BSS). In some embodiments, the expandable tip is first expanded, and then the RBS (e.g., disk 405, seed-shaped RBS 400) or the radioactive portion of the memory wire 300 is deployed. Without wishing to limit the present invention to any theory or mechanism, it is believed that an expandable tip is advantageous because it could act as a guide to position the cannula 100 in the correct location. The physician may be able to confirm the position of the cannula 100 because the expanded tip would create a convexity in the sclera 235. The expandable tip may further comprise a shield for preventing radiation from projecting to an area other than the target area (e.g., the patient's eye).

In some embodiments, the expandable tip is a balloon. In some embodiments, the balloon in its non-expanded state covers the distal portion 110 of the cannula 100 like a sheath.

Doses

As used herein, the term "lateral" and/or "laterally" refers to in the direction of any line that is perpendicular to line $l_R$, wherein line $l_R$ is the line derived from connecting the points $l_S$ and $l_T$, wherein $l_S$ is the point located at the center of the RBS and $l_T$ is the point located at the center of the target (see FIG. 10, FIG. 12).

As used herein, the term "forwardly" refers to in the direction of and/or along line $l_R$ from $l_S$ through $l_T$, (see FIG. 10)

As used herein, the term "substantially uniform" refers to a group of values (e.g., two or more values) wherein each value in the group is no less than about 90% of the highest value in the group. For example, an embodiment wherein the radiation doses at a distance of up to about 1 mm from the center of the target are substantially uniform implies that any radiation dose within the distance of up to about 1 mm away from the center of the target is no less than about 90% of the highest radiation dose within that area (e.g., the total target center radiation dose). For example, if a group of relative radiation doses within a distance of up to about 1 mm away from the center of the target are measured to be 99, 97, 94, 100, 92, 92, and 91, the relative radiation doses are substantially uniform because each value in the group is no less than 90% of the highest value in the group (100).

As used herein, the term "isodose" (or prescription isodose, or therapeutic isodose) refers to the area directly surrounding the center of the target wherein the radiation dose is substantially uniform (see FIG. 13).

Without wishing to limit the present invention to any theory or mechanism, the devices and methods of the present invention are believed to be effective by delivering a substantially uniform dose to the entire target region (e.g., neovascular tissue), or a non-uniform dose, in which the center of the target has dose that is about 2.5× higher than the dose at the boundary regions of the target.

In some embodiments, a dose of about 16 Gy is delivered to the target. In some embodiments, a dose of about 16 Gy to 20 Gy is delivered to the target. In some embodiments, a dose of about 20 Gy is delivered to the target. In some embodiments, a dose of about 24 Gy is delivered to the target. In some embodiments, a dose of about 20 Gy to 24 Gy is delivered to the target. In some embodiments, a dose of about 30 Gy is delivered to the target. In some embodiments, about 24 Gy to 30 Gy is delivered to the target. In some embodiments, a dose of about 30 Gy to 50 Gy is delivered to the target. In some embodiments, a dose of about 50 Gy to 100 Gy is delivered to the target. In some embodiments, a dose of about 75 Gy is delivered to the target.

Dose Rates

The medical radiation community believes as medicolegal fact that low dose rate irradiation (e.g., less than about 10 Gy/min) is preferred over high dose rate irradiation because high dose rate irradiation may cause more complications. For example, the scientific publication "Posttreatment Visual Acuity in Patients Treated with Episcleral Plaque Therapy for Choroidal Melanomas: Dose and Dose Rate Effects" (Jones, R., Gore, E., Mieler, W., Murray, K., Gillin, M., Albano, K., Erickson, B., International Journal of Radiation Oncology Biology Physics, Volume 52, Number 4, pp. 989-995, 2002) reported the result "macula dose rates of 111 cGy/h (+/−11.1 cGy/h) were associated with a 50% risk of significant visual loss," leading them to conclude "higher dose rates to the macula correlated strongly with poorer posttreatment visual outcome." Furthermore, the American Brachytherapy Society (ABS) issued their recommendations in the scientific publication, "The American Brachytherapy Society Recommendations for Brachytherapy of Uveal Melanomas" (Nag, S., Quivey, J. M., Earle, J. D., Followill, D., Fontanesi, J., and Finger, P. T., International Journal of Radiation Oncology Biology Physics, Volume 56, Number 2, pp. 544-555, 2003) stating "the ABS recommends a minimum tumor I-125 dose of 85 Gy at a dose rate of 0.60 to 1.05 Gy/h using AAPM TG-43 formalism for the calculation of dose." Thus, the medical standard of care requires low dose rates.

Despite the teachings away from the use of high dose rates, the inventors of the present invention surprisingly discovered that a high dose rate (i.e., above about 10 Gy/min) may be advantageously used to treat neovascular conditions.

In some embodiments, the dose rate delivered/measured at the target is greater than 10 Gy/min (e.g., about 15 Gy/min, 20 Gy/min). In some embodiments, the dose rate delivered/measured at the target is between about 10 Gy/min to 15 Gy/min. In some embodiments, the dose rate delivered/measured at the target is between about 15 Gy/min to 20 Gy/min. In some embodiments, the dose rate delivered/measured at the target is between about 20 Gy/min to 30 Gy/min. In some embodiments, the dose rate delivered/measured at the target is between about 30 Gy/min and 40 Gy/min. In some embodiments, the dose rate delivered/measured at the target is between about 40 Gy/min to 50 Gy/min. In some embodiments, the dose rate delivered/measured at the target is between about 50 Gy/min to 75 Gy/min. In some embodiments, the dose rate delivered/measured at the target is between about 75 Gy/min to 100 Gy/min. In some embodiments, the dose rate delivered/measured at the target is greater than about 100 Gy/min.

In some embodiments, about 16 Gy of radiation is delivered with a dose rate of about 16 Gy/min for about 1 minute (as measured at the target). In some embodiments, about 20 Gy of radiation is delivered with a dose rate of about 20 Gy/min for about 1 minute (as measured at the target). In some embodiments, about 25 Gy is delivered with a dose rate of about 12 Gy/min for about 2 minutes (as measured at the target). In some embodiments, about 30 Gy of radiation is delivered with a dose rate of greater than about 10 Gy/min (e.g., 11 Gy/min) for about 3 minutes (as measured at the target). In some embodiments, about 30 Gy of radiation is delivered with a dose rate of about 15 Gy/min to 16 Gy/min for about 2 minutes (as measured at the target). In some embodiments, about 30 Gy of radiation is delivered with a dose rate of about 30 Gy/min for about 1 minute (as measured at the target). In some embodiments, about 40 Gy of radiation is delivered with a dose rate of about 20 Gy/min for about 2 minutes (as measured at the target). In some embodiments, about 40 Gy of radiation is delivered with a dose rate of about 40 Gy/min for about 1 minute (as measured at the target). In some embodiments, about 40 Gy of radiation is delivered with a dose rate of about 50 Gy/min for about 48 seconds (as measured at the target). In some embodiments, about 50 Gy of radiation is delivered with a dose rate of about 25 Gy/min for about 2 minutes (as measured at the target). In some embodiments, about 50 Gy of radiation is delivered with a dose rate of about 75 Gy/min for about 40 seconds (as measured at the target). In some embodiments, a dose rate of about 75 Gy is delivered with a dose rate of about 75 Gy/min for about 1 minute (as measured at the target). In some embodiments, a dose rate of about 75 Gy is delivered with a dose rate of about 25 Gy/min for about 3 minutes (as measured at the target).

In some embodiments, the target is exposed to the radiation between about 0.01 seconds to about 0.10 seconds. In some embodiments, the target is exposed to the radiation between about 0.10 seconds to about 1.0 second. In some embodiments, the target is exposed to the radiation between about 1.0 second to about 10 seconds. In some embodiments, the target is exposed to the radiation between about 10 seconds to about 15 seconds. In some embodiments, the target is exposed to the radiation between about 15 seconds to 30 seconds. In some embodiments, the target is exposed to the radiation between about 30 seconds to 1 minute. In some embodiments, the target is exposed to the radiation between about 1 minute to about 5 minutes. In some embodiments, the target is exposed to the radiation between about 5 minutes to about 7 minutes. In some embodiments, the target is exposed to the radiation between about 7 minutes to about 10 minutes. In some embodiments, the target is exposed to the radiation between about 10 minutes to about 20 minutes. In some embodiments, the target is exposed to the radiation between about 20 minutes to about 30 minutes. In some embodiments, the target is exposed to the radiation between about 30 minutes to about 1 hour. In some embodiments, the target is exposed to the radiation for more than 1 hour.

Doses, Dose Rates for Tumors

Without wishing to limit the present invention to any theory or mechanism, it is believed that for treating or managing conditions other than macula degeneration (e.g., tumors), a typical dose is expected to be in the range of about 10 Gy to about 100 Gy, such as 85 Gy. Furthermore, it is believed that to irradiate from the exterior side of the eye where the radiation has to pass through the sclera, the RBS should provide a dose rate of about 0.6 Gy/min to about 100 Gy/min to the target. In some embodiments, for treating conditions other than macula degeneration (e.g., tumors), the RBS provides a dose rate of greater than about 10 Gy/min to about 20 Gy/min to the target. In some embodiments, the RBS provides a dose rate of greater than about 20 to 40 Gy/min (e.g., 36 Gy/min) to the target. In some embodiments, the RBS provides a dose rate of greater than about 40 to 60 Gy/min to the target. In some embodiments, the RBS provides a dose rate of greater than about 60 to 80 Gy/min to the target. In some embodiments, the RBS provides a dose rate of greater than about 80 to 100 Gy/min to the target. In some embodiments, the dose rate that is chosen by a user (e.g. physicist, physician) to irradiate the tumor depends on one or more characteristics (e.g., height/thickness of the tumor/lesion (e.g., the thickness of the tumor may dictate what dose rate the user uses).

Without wishing to limit the present invention to any theory or mechanism, it is believed that the exposure time should be between about 15 seconds to about 10 minutes for practical reasons. However, other exposure times may be used. In some embodiments, the target is exposed to the radiation between about 0.01 seconds to about 0.10 seconds.

In some embodiments, the target is exposed to the radiation between about 0.10 seconds to about 1.0 second. In some embodiments, the target is exposed to the radiation between about 1.0 second to about 10 seconds. In some embodiments, the target is exposed to the radiation between about 10 seconds to about 15 seconds. In some embodiments, the target is exposed to the radiation between about 15 seconds to 30 seconds. In some embodiments, the target is exposed to the radiation between about 30 seconds to 1 minute. In some embodiments, the target is exposed to the radiation between about 1 to 5 minutes. In some embodiments, the target is exposed to the radiation between about 5 minutes to about 7 minutes. In some embodiments, the target is exposed to the radiation between about 7 minutes to about 10 minutes. In some embodiments, the target is exposed to the radiation between about 10 minutes to about 20 minutes. In some embodiments, the target is exposed to the radiation between about 20 minutes to about 30 minutes. In some embodiments, the target is exposed to the radiation between about 30 minutes to about 1 hour. In some embodiments, the target is exposed to the radiation for more than 1 hour.

Radiation Area, Radiation Profile

In some embodiments, the cannula 100 and/or RBSs of the present invention are designed to treat a small target area with a substantially uniform dose and are also designed so that the radiation dose declines more rapidly as measured laterally from the target as compared to the prior art (see FIG. 8). The prior art conversely teaches the advantages of a substantially uniform dose over a larger diameter target and with a slower decline in radiation dose (as measured laterally) (e.g., U.S. Pat. No. 7,070,544 B2).

In some embodiments, the radiation dose rapidly declines as measured laterally from edge of an isodose (e.g., the area directly surrounding the center of the target wherein the radiation dose is substantially uniform) (as shown in FIG. 8).

FIG. 11 shows a non-limiting example of a radiation dose profile (as measured laterally) of a 1 mm source comprised of Sr-90. In some embodiments, the radiation dose at a distance of about 0.5 mm from the center of the target is about 10% less than the dose on the central axis of the target. In some embodiments, the radiation dose at a distance of about 1.0 mm from the center of the target is about 30% less than the dose on the central axis of the target. In some embodiments, the radiation dose at a distance of about 2.0 mm from the center of the target is about 66% less than the dose on the central axis of the target. In some embodiments, the radiation dose at a distance of about 3.0 mm from the center of the target is about 84% less than the dose on the central axis of the target. In some embodiments, the radiation dose at a distance of about 4.0 mm from the center of the target is about 93% less than the dose on the central axis of the target.

In some embodiments, the dose on the central axis of the target is the dose delivered at the choroidal neovascular membrane (CNVM). In some embodiments the radiation dose extends away from the target (e.g., choroidal neovascular membrane) in all directions (e.g., laterally, forwardly), wherein the distance that the radiation dose laterally extends in a substantially uniform manner is up to about 0.75 mm away. In some embodiments the radiation dose extends away from the target in all directions (e.g., laterally, forwardly), wherein the distance that the radiation dose laterally extends in a substantially uniform manner is up to about 1.5 mm away. In some embodiments the radiation dose extends away from the target in all directions (e.g., laterally, forwardly), wherein the distance that the radiation dose laterally extends in a substantially uniform manner is up to about 2.5 mm away.

In some embodiments, the radiation dose at a distance of 2 mm laterally from the center of the target is less than 60% of the radiation dose on the central axis of the target. In some embodiments, the radiation dose at a distance of 3 mm laterally from the center of the target is less than 25% of the radiation dose at the center of the target. In some embodiments, the radiation dose at a distance of 4 mm laterally from the center of the target is less than 10% of the radiation dose at the center of the target. Because the edge of the optic nerve is close to the target, this dose profile provides greater safety for the optic nerve than methods of the prior art.

In some embodiments, the radiation dose is substantially uniform within a distance of up to about 1.0 mm (as measured laterally) from the center of the target. In some embodiments, the radiation dose declines such that at a distance of about 2.0 mm (as measured laterally) from the center of the target, the radiation dose is less than about 25% of the radiation dose at the center of the target. In some embodiments, the radiation dose declines such that at a distance of about 2.5 mm (as measured laterally) from the center of the target, the radiation dose is less than about 10% of the radiation dose at the center of the target.

In some embodiments, the radiation dose is substantially uniform within a distance of up to about 6.0 mm (as measured laterally) from the center of the target. In some embodiments, the radiation dose declines such that at a distance of about 12.0 mm (as measured laterally) from the center of the target, the radiation dose is less than about 25% of the radiation dose at the center of the target. In some embodiments, the radiation dose declines such that at a distance of about 15.0 mm (as measured laterally) from the center of the target, the radiation dose is less than about 10% of the radiation dose at the center of the target.

In some embodiments, the radiation dose is substantially uniform within a distance of up to about 10.0 mm (as measured laterally) from the center of the target. In some embodiments, the radiation dose declines such that at a distance of about 20.0 mm (as measured laterally) from the center of the target, the radiation dose is less than about 25% of the radiation dose at the center of the target. In some embodiments, the radiation dose declines such that at a distance of about 25.0 mm (as measured laterally) from the center of the target, the radiation dose is less than about 10% of the radiation dose at the center of the target.

In some embodiments, the radiation dose at the center of the target (e.g., radiation dose at the center of the choroidal neovascular membrane) does not extend laterally to the entire macula (a diameter of about 1.5 mm to 6.0 mm). In some embodiments, the devices of the present invention may also treat a larger area and still have a faster radiation dose fall off as compared to devices of the prior art.

Benefit of Short Delivery Time

Without wishing to limit the present invention to any theory or mechanism, it is believed that faster delivery time of radiation is advantageous because it allows the physician to hold the instrument in the desired location with minimal fatigue, and it minimizes the amount of time that the patient is subjected to the procedure. Lower dose rates and longer delivery times may cause fatigue in the physician, possibly leading to the accidental movement of the cannula from the target. Furthermore, longer delivery times increase the chance of any movements of the physician's hand or the patient's eye or head (when local anesthesia is employed, the patient is awake during the procedure).

Another benefit of a faster delivery time is the ability to employ short-term local anesthetics (e.g., lidocaine) and/or systemic induction drugs or sedatives (e.g., methohexital sodium, midazolam). Use of short-term anesthetics result in a quicker recovery of function (e.g., motility, vision) after the procedure. Shorter acting anesthetics cause shorter-lasting respiratory depression in case of accidental central nervous system injection.

Shutter System

In some embodiments, the cannula 100 comprises a shutter system disposed near or at the tip 200 of the cannula 100. The shutter system may be similar to the shutter system of a camera. In some embodiments, a shutter system is used to deliver up to about a 200,000 Gy/min dose rate in a time frame of about 0.01 second. Without wishing to limit the present invention to any theory or mechanism, it is believed that a shutter system would be advantageous because it would allow for such a short exposure time that the radiation dose can be delivered to the target without worry of a hand, eye, or head movement moving the cannula 100 away from the target.

Alternatively to a shutter system, in some embodiments, a high dose rate can be delivered in a short amount of time using a mechanism of a very fast after-loaded system, wherein the RBS is quickly moved to the treatment position for a quick dwell time and the retracted away from the treatment position.

The present invention is illustrated herein by example, and various modifications may be made by a person of ordinary skill in the art. For example, although the cannulae 100 of the present invention have been described above in connection with the preferred sub-Tenon radiation delivery generally above the macula, the cannulae 100 may be used to deliver radiation directly on the outer surface of the sclera 235, below the Tenon's capsule 230, and generally above portions of the retina other than the macula. Moreover, in some embodiments, the devices (e.g., cannulae 100) of the present invention may be used to deliver radiation from below the conjunctiva and above the Tenon's capsule 230. In some embodiments, the devices may be used to deliver radiation to the anterior half of the eye. In some embodiments, the devices may be used to deliver radiation from above the conjunctiva. As another example, the arc length and/or radius of curvature of the distal portions of the cannulae may be modified to deliver radiation within the Tenon's capsule 230 or the sclera 235, generally above the macula or other portions of the retina, if desired.

Additional Rationale of Device and Methods

Without wishing to limit the present invention to any theory or mechanism, it is believed that the methods of the present invention, which feature a posterior radiation approach, are superior to methods that employ either a pre-retinal approach or an intravitreal radiation approach using an intravitreal device 910 (see FIG. 9, see U.S. Pat. No. 7,223,225 B2) for several reasons.

For example, the pre-retinal approach (e.g., irradiating the target area by directing the radiation from the anterior side of the retina back toward the target) irradiates the anterior structures of the eye (e.g., cornea, iris, ciliary body, lens) and has the potential to irradiate the tissues deeper than the lesion, such as the periorbital fat, bone, and the brain. The intravitreal radiation approach (e.g., irradiating the target area by directing the radiation from within the vitreous chamber from the anterior side of the eye back towards the target) also has the potential to irradiate the tissues deeper than the lesion (e.g., periorbital fat, bone, brain) and also, in a forward direction, the lens, ciliary body and cornea. It is believed that the methods of the present invention will spare the patient from receiving ionizing radiation in the tissues behind the eye and deeper than the eye. According to the present invention, the radiation is directed forward (e.g., the radiation is directed from the posterior side of the eye forward to the target) and is shielded in the back, and therefore excess radiation would enter primarily into the vitreous gel and avoid the surrounding tissues (e.g., fat, bone, brain).

Keeping the cannula 100 in a fixed location and at a distance from the target during the treatment reduces the likelihood of errors and increases the predictability of dose delivery. Conversely, approaching the radiation treatment by inserting a device into the vitreous chamber (e.g., an intravitreal approach) requires a physician to hold the device in a fixed location and a fixed distance from the target in the spacious vitreous chamber (see FIG. 9). It may be difficult for the physician to hold precisely that position for any length of time. Furthermore, it is generally not possible for the physician/surgeon to know the exact distance between the probe and the retina; he/she can only estimate the distance. By approaching the treatment from behind the eye, the physician is able to hold the device at a precise fixed distance from the target because the intervening structures (e.g., the sclera 235) support the device, help to hold the cannula 100 in place, and act as a fixed spacer. This improves both the geometric accuracy and dose precision. As shown in FIG. 29, Table 4, the radiation dose varies greatly depending on the depth (e.g., distance away from the source as measured along line $l_R$). For example, if the distance between the RBS (e.g., probe) is moved from 0.1 mm away from the target to 0.5 mm, the dose may decrease by about 25 to 50%.

The posterior approach is also easier and faster than the intravitreal approach. The posterior approach is less invasive than the intravitreal approach, and avoids the side effects of intravitreal procedures (e.g., vitrectomy, intravitreal steroid injections or VEGF injections) which are often cataractogenic, as well as the possibility of mechanical trauma to the retina or intraocular infection. The posterior approach is safer for the patient.

Without wishing to limit the present invention to any theory or mechanism, it is believed that the devices of the present invention are advantageous over other posterior radiation devices of the prior art because the devices of the present invention are simpler mechanically and less prone to malfunction. In some embodiments, the devices of the present invention are only used one time.

Without wishing to limit the present invention to any theory or mechanism, it is believed that the unique radiation profile of the present invention is advantageous over the prior art. As discussed previously and as shown in FIG. 8, the devices and methods of the present invention, which suitably employ the rotationally symmetrical surface concept described above, provide for a more sharply demarcated dose radiation profile from the edge of a substantially uniform dose region. Other posterior devices do not provide this unique radiation profile. The devices and methods of the present invention are advantageous because they will deliver a therapeutic dose of radiation to the target (e.g., neovascular growths affecting the central macula structures) while allowing for the radiation dose to fall off more quickly than the prior art, which helps prevent exposure of the optic nerve and/or the lens to radiation. Further, a faster fall off of the lateral radiation dose minimizes the risk and the extent of radiation retinopathy, retinitis, vasculitis, arterial and/or venous thrombosis, optic neuropathy and possibly hyatrogenic neoplasias.

In some embodiments, the cannula 100 is after-loaded with radiation. In some embodiments, the RBS is pushed forward to an orifice 500 or a window 510 at the tip 200 of the cannula 100. In some embodiments, the devices of the present invention do not comprise a removable shield or a shutter.

The present methods of treatment may be used alone or in combination with a pharmaceutical, e.g., for treating Wet Age-Related Macular Degeneration. Non-limiting examples of pharmaceuticals that may be used in combination with the present invention includes a radiation sensitizer an anti-VEGF (vascular endothelial growth factor) drug such as Lucentis® or Avastin®, and/or other synergistic drugs such as steroids, vascular disrupting agent therapies, and other anti-angiogenic therapies both pharmacologic and device-based.

For example, the present invention may be used in combination with a pharmaceutical (e.g., a "first treatment") such as an anti-angiogenesis treatment for inhibiting an angiogenesis target. The present invention may also be used in combination with more than one pharmaceutical (e.g., a first treatment and a second treatment, etc.). Administration may be simultaneous or consecutive. For example, in some embodiments, the present invention is used in combination with an anti-angiogenesis treatment (e.g., the first treatment) and a steroid treatment (e.g., the second treatment), e.g., corticosteroid treatment.

Without wishing to limit the present invention to any theory or mechanism, non-limiting examples of angiogeneis inhibitors may include angiopoeitin 2, soluble vascular endothelial growth factor receptor-1 (VEGFR-1), soluble Tie2, soluble neuropilin-1 (NRP-1), endostatin, angiostatin, tissue inhibitor of metalloprotease-3 (TIMP-3), prolactin, platelet factor-4, calreticulin, thrombospondin 1 (TSP-1), thrombospondin 2 (TSP-1), Vandetanib (e.g., ZD6474), PDGF inhibitors, pigment epithelium-derived factor (PEDF), VEGF inhibitory aptamers, e.g., Macugen® (pegaptanib, Pfizer), antibodies or fragments thereof, e.g., anti-VEGF antibodies, e.g., bevacizumab (Avastin®, Genentech), or fragments thereof, e.g., ranibizumab (Lucentis®, Genentech), soluble fins-like tyrosine kinase 1 (sFltI) polypeptides or polynucleotides; PTK/ZK; KRN633; inhibitors of integrins (e.g., αvβ3 and α5β1); VEGF-Trap® (Regeneron); Alpha2-antiplasmin, cartilage-derived angiogenesis inhibitor (CDAI), disintegrin and metalloproteinase with thrombospondin motifs 1 (ADAMTS1), ADAMTS2, IFN-alpha, IFN-beta, IFN-gamma, chemokin (C-X-C motif) ligand 10 (CYCL10), IL-4, IL-12, IL-18, prothrombin, antithrombin III fragments, and vascular endothelial growth inhibitor (VEGI), anti-hypoxia inducible factor-1 (anti-HIF-1) compounds or treatments, and immunosuppressant compounds such as calcineurin inhibitors (e.g., tacrolimus) or mTOR inhibitors (e.g., rapamycin), e.g., see W.O. Pat. Application No. 2008/119500, the disclosure of which is incorporated in its entirety by reference herein.

Without wishing to limit the present invention to any theory or mechanism, other angiogenesis inhibitors may also be found in U.S. Patent Application No. 2008/0193499; U.S. Pat. No. 7,091,175, U.S. Patent Application 2001/0041744; U.S. Pat. No. 6,472,379; U.S. Pat. Application No. 2002/0001630; U.S. Patent Application 2005/0043220; U.S. Patent Application 2004/0048807, the disclosures of which re incorporated in their entirety by reference herein.

Without wishing to limit the present invention to any theory or mechanism, non limiting examples of corticosteroids are I'-alpha, 17-alpha, 21-trihydroxypregn-4-ene-3,20-dione; 11-beta, 16-alpha, 17, 21-tetrahydroxypregn-4-ene-3, 20-dione; 11-beta, 16-alpha, 17, 21-tetrahydroxypregn-1, 4-diene-3, 20-dione; 11-beta, 17-alpha, 21-trihydroxy-6-alpha-methylpregn-4-ene-3,20-dione; 11-dehydrocorticosterone; 11-deoxycortisol; 11-hydroxy-I, 4-androstadiene-3,17-dione; 11-ketotestosterone; 14-hydroxyandrost-4-ene-3,6, 17-trione; 15,17-dihydroxyprogesterone; 16-methylhydrocortisone; 17,21-dihydroxy-16-alpha-methylpregna-I, 4,9(11)-triene-3, 20-dione; 17-alpha-hydroxypregn-4-ene-3, 20-dione; 17-alpha-hydroxypregnenolone; 17-hydroxy-16-beta-methyl-5-beta-pregn-9(11)-ene-3,20-dione; 17-hydroxy-4,6,8(14)-pregnatriene-3,20-dione; 17-hydroxypregna-4,9(11)-diene-3,20-dione; 18-hydroxycorticosterone; 18-hydroxycortisone; 18-oxocortisol; 21-acetoxypregnenolone; 21-deoxyaldosterone; 21-deoxycortisone; 2-deoxyecdysone; 2-methylcortisone; 3-dehydroecdysone; 4-pregnene-17-alpha, 20-beta, 21-triol-3,11-dione; 6,17,20-trihydroxypregn-4-ene-3-one; 6-alpha-hydroxycortisol; 6-alpha-fluoroprednisolone, 6-alpha-methylprednisolone, 6-alpha-methylprednisolone 21-acetate, 6-alpha-methylprednisolone 21-hemisuccinate sodium salt, 6-beta-hydroxycortisol, 6-alpha, 9-alpha-difluoroprednisolone 21-acetate 17-butyrate, 6-hydroxycorticosterone; 6-hydroxydexamethasone; 6-hydroxyprednisolone; 9-fluorocortisone; alclomethasone dipropionate; aldosterone; algestone; alphaderm; amadinone; amcinonide; anagestone; androstenedione; anecortave acetate; beclomethasone; beclomethasone dipropionate; betamethasone 17-valerate; betamethasone sodium acetate; betamethasone sodium phosphate; betamethasone valerate; bolasterone; budesonide; calusterone; chlormadinone; chloroprednisone; chloroprednisone acetate; cholesterol; ciclesonide; clobetasol; clobetasol propionate; clobetasone; clocortolone; clocortolone pivalate; clogestone; cloprednol; corticosterone; Cortisol; Cortisol acetate; Cortisol butyrate; Cortisol cypionate; Cortisol octanoate; Cortisol sodium phosphate; Cortisol sodium succinate; Cortisol valerate; cortisone; cortisone acetate; cortivazol; cortodoxone; daturaolone; deflazacort, 21-deoxycortisol, dehydroepiandrosterone; delmadinone; deoxycorticosterone; deprodone; descinolone; desonide; desoximethasone; dexafen; dexamethasone; dexamethasone 21-acetate; dexamethasone acetate; dexamethasone sodium phosphate; dichlorisone; diflorasone; diflorasone diacetate; diflucortolone; difluprednate; dihydroelatericin a; domoprednate; doxibetasol; ecdysone; ecdysterone; emoxolone; endrysone; enoxolone; fluazacort; flucinolone; flucloronide; fludrocortisone; fludrocortisone acetate; flugestone; flumethasone; flumethasone pivalate; flumoxonide; flunisolide; fluocinolone; fluocinolone acetonide; fluocinonide; fluocortin butyl; 9-fluorocortisone; fluocortolone fluorohydroxyandrostenedione; fluorometholone; fluorometholone acetate; fluoxymesterone; fluperolone acetate; fluprednidene; fluprednisolone; flurandrenolide; fluticasone; fluticasone propionate; formebolone; formestane; formocortal; gestonorone; glyderinine; halcinonide; halobetasol propionate; halometasone; halopredone; haloprogesterone; hydrocortamate; hydrocortisone cypionate; hydrocortisone; hydrocortisone 21-butyrate; hydrocortisone aceponate; hydrocortisone acetate; hydrocortisone buteprate; hydrocortisone butyrate; hydrocortisone cypionate; hydrocortisone hemisuccinate; hydrocortisone probutate; hydrocortisone sodium phosphate; hydrocortisone sodium succinate; hydrocortisone valerate; hydroxyprogesterone; inokosterone; isoflupredone; isoflupredone acetate; isoprednidene; loteprednol etabonate; meclorisone; mecortolon; medrogestone; medroxyprogesterone; medrysone; megestrol; megestrol acetate; melengestrol; meprednisone; methandrostenolone; methylprednisolone; methylprednisolone aceponate; methylprednisolone acetate; methylprednisolone hemisuccinate; methylprednisolone sodium succinate; methyltestosterone; metribolone; mometasone; mometasone furoate; mometasone furoate monohydrate; nisone; nomegestrol; norgestomet; norvinisterone; oxymesterone; paramethasone; paramethasone acetate; ponasterone; prednicarbate; prednisolamate; prednisolone; prednisolone 21-diethylaminoacetate; prednisolone 21-hemisuccinate; prednisolone acetate; prednisolone farnesylate; prednisolone hemisuccinate; prednisolone-21 (beta-D-glucuronide); prednisolone metasulphobenzoate; prednisolone sodium phosphate; prednisolone steaglate; prednisolone tebutate; prednisolone tetrahydrophthalate; prednisone; prednival; prednylidene; pregnenolone; procinonide; tralonide; progesterone; promegestone; rhapontisterone; rimexolone; roxibolone; rubrosterone; stizophyllin; tixocortol; topterone; triamcinolone; triamcinolone acetonide; triamcinolone acetonide 21-palmitate; triamcinolone benetonide; triamcinolone diacetate; triamcinolone hexacetonide; trimegestone; turkesterone; and wortmannin.

The terms "compound that inhibits VEGF," "anti-VEGF treatment," and/or "anti-VEGF drug" may refer to a compound (or the like) that inhibits the activity or production of vascular endothelial growth factor (VEGF). For example, the terms may refer to compounds capable of binding VEGF, including small organic molecules, antibodies or antibody fragments specific to VEGF, peptides, cyclic peptides, nucleic acids, antisense nucleic acids, RNAi, and ribozymes that inhibit VEGF expression at the nucleic acid level. Non-limiting examples of compounds that inhibit VEGF are nucleic acid ligands of VEGF (e.g., such as those described in U.S. Pat. No. 6,168,778 or U.S. Pat. No. 6,147,204), EYEOOI (previously referred to as NX1838) which is a modified pegylated aptamer that binds with high affinity to the major soluble human VEGF isoform; VEGF polypeptides (e.g., U.S. Pat. No. 6,270,933 and WO Pat. No. 99/47677); oligonucleotides that inhibit VEGF expression at the nucleic acid level, for example antisense RNAs (e.g. U.S. Pat. No. 5,710,136; U.S. Pat. No. 5,661,135; U.S. Pat. No. 5,641,756; U.S. Pat. No. 5,639,872; U.S. Pat. No. 5,639,736). Other examples of inhibitors of VEGF signaling known in the art may include, e.g., ZD6474; COX-2, Tie2 receptor, angiopoietin, and neuropilin inhibitors; PEDF, endostatin, and angiostatin, soluble fms-like tyrosine kinase 1 (sFltI) polypeptides or polynucleotides; PTK787/ZK222 584; KRN633; VEGF-Trap® (Regeneron); and Alpha2-antiplasmin. Compounds that inhibit VEGF may be antibodies to, or antibody fragments thereof, or aptamers of VEGF or a related family member such as (VEGF B, I C, D; PDGF). Examples are anti-VEGF antibodies, e.g., Avastin™ (also reviewed as bevacizumab, Genentech), or fragments thereof. e.g., Lucentis™ (also reviewed as rhuFAb V2 or AMD-Fab; ranibizumab. Genentech), and other anti-VEGF compounds such as VEGF inhibitory aptamers, e.g., Macugen™ (also reviewed as pegaptanib sodium, anti-VEGF aptamer or EYEOOI, Pfizer). In some embodiments, a compound that inhibits VEGF can further be an immunosuppressant compound (e.g., calcineurin inhibitors, mTOR inhibitors). The disclosures of all referenced U.S. Patents and W.O Patents are incorporated in their entirety by reference herein.

In some embodiments, the pharmaceutical (e.g., angiogenesis inhibitor, e.g., VEGF-inhibitor, etc.) may comprise a compound selected from the group consisting of an oestrogen (e.g. oestrodiol), an androgen (e.g. testosterone) retinoic acid derivatives (e. g. 9-cis-retinoic acid, 13-trans-retinoic acid, all-trans retinoic acid), a vitamin D derivative (e. g. calcipotriol, calcipotriene), a non-steroidal antiinflammatory agent, a selective serotonin reuptake inhibitor (SSRI; e.g. fluoxetine, sertraline, paroxetine), a tricyclic antidepressant (TCA; e.g. maprotiline, amoxapine), a phenoxy phenol (e.g. triclosan), an antihistamine (e.g. loratadine, epinastine), a phosphodiesterase inhibitor (e.g. ibudilast), an anti-infective agent, a protein kinase C inhibitor, a MAP kinase inhibitor, an anti-apoptotic agent, a growth factor, a nutrient vitamin, an unsaturated fatty acid, and/or ocular anti-infective agents, for the treatment of the ophthalmic disorders set forth herein (see for example compounds disclosed in US 2003/0119786; WO 2004/073614; WO 2005/051293; US 2004/0220153; WO 2005/027839; WO 2005/037203; WO 03/0060026). Anti-infective agents may include but are not limited to penicillins (ampicillin, aziocillin, carbenicillin, dicloxacillin, methicillin, nafcillin, oxacillin, penicillin G, piperacillin, and ticarcillin), cephalosporins (cefamandole, cefazolin, cefotaxime, cefsulodin, ceftazidime, ceftriaxone, cephalothin, and moxalactam), aminoglycosides (amikacin, gentamicin, netilmicin, tobramycin, and neomycin), miscellaneous agents such as aztreonam, bacitracin, ciprofloxacin, clindamycin, chloramphenicol, cotrimoxazole, fusidic acid, imipenem, metronidazole, teicoplanin, and vancomycin), antifungals (amphotericin B, clotrimazole, econazole, fluconazole, flucytosine, itraconazole, ketoconazole, miconazole, natamycin, oxiconazole, and terconazole), antivirals (acyclovir, ethyldeoxyuridine, foscarnet, ganciclovir, idoxuridine, trifluridine, vidarabine, and (S)-1-(3-dydroxy-2-phospho-nyluethoxypropyl) cytosine (HPMPC)), antineoplastic agents (cell cycle (phase) nonspecific agents such as alkylating agents (chlorambucil, cyclophosphamide, mechlorethamine, melphalan, and busulfan), anthracycline antibiotics (doxorubicin, daunomycin, and dactinomycin), cisplatin, and nitrosoureas), antimetabolites such as antipyrimidines (cytarabine, fluorouracil and azacytidine), antifolates (methotrexate), antipurines (mercaptopurine and thioguanine), bleomycin, vinca alkaloids (vincrisine and vinblastine), podophylotoxins (etoposide (VP-16)), and nitrosoureas (carmustine, (BCNU)), and inhibitors of proteolytic enzymes such as plasminogen activator inhibitors.

The pharmaceutical (or combination of pharmaceuticals) may include an anti-paracyte (e.g., a paracyte is a cell that adheres and matures new vessels). The pharmaceutical (or combination of pharmaceuticals) may include a VEGF-Trap (Bayer). The pharmaceutical (or combination of pharmaceuticals) may comprise a PDT agent, e.g., verteporfin (Visudyne, Novartis), SnET2 PDT (Photrex, Miravant); a steroid, e.g., anecoratve (Retaane Depot, Alcon), dexamethasone (Posurdex, Allergan), floucinolone acetonide (Iluvien, Alimera Sciences/pSivida); a microtubule de-stabilizer/VDA, e.g., CA4P (Zybresta, OXiGENE); a PEGylated anti-VEGF aptamer, e.g., pegaptanib (Macugen, OSI/Pfizer/Gilead Sciences); a Pan-VEGF Fab', e.g., ranulizumab (Lucentis, Genentech/Novartis); bevacizumab (Avastin, Genentech); a small molecule VEGFR inhibitor, e.g., AG-13958 (Pfizer); VEGF-Trap (Regeneron/Bayer); a soluble decoy fusion protein comprising portions of VEGFR1 and VEGFR2 that binds VEGF and PlGF, e.g., AVE0005 (Aflibercept (Regeneron/Sanofi); an RNAi, e.g., Sima-027 (Merck/Allergan), ALN-VEG01 (Alnylam); an anti-a5B1 integrin Fab', e.g., F200 (Protein Design Lab); ACZ885F (Novartis); an anti-angiogenic compound, e.g., ATG-3/ATG-003 (CoMentis), an NSAID, e.g., xibrom bromfenac (Ista Pharmaceuticals Inc & Senju Pharmaceutical Co.); a small molecule resolvin, e.g., NPDI (Resolvyx); RX 10001 (RvEI); RX 10008; an immunosuppressive, anti-angiogenic, anti-migratory, anti-proliferative, anti-fibrotic, and/or anti-permeability compound, e.g., sirolimus (e.g., rapamycin) DE-109 (Santen & MacuSight); a siRNA, e.g., bevasiranib (OPKO Health Inc); an antibody fragment, e.g., ESBA903 (ESBATech); a complement inhibitor, e.g., POT-4 (Potentia); a fusion protein (consisting of a complement receptor 2 (CR2) fragment linked to an inhibitory domain of complement factor H (CFH) that inhibits the complement alternative pathway). e.g., TT30 (Taligen); an alpha(5)beta(1) integrin, e.g., JSM-6427; a monoclonal antibody (against sphingosine 1-phosphate), e.g., sphingomab (Lpath Inc.); squalamine; an anti-PDGF aptamer against PDGF-B, e.g., E10030 (Ophthotech); an anti-C5 aptamer, e.g., ARC1905 (Ophthotech); a stem cell based therapy, e.g., HuCNS-SC (StemCells Inc); pyrimidine derivatives, benzodiazepinyl derivatives; embryonic stem cell therapies; aminoacyl tRNA synthetase fragments; PDGF anti-cancer drugs in combination with Lucentis (e.g., Gleeve tablet+Lucentis); amino acid peptide isolated from scorpion venom (e.g., TM601, chlorotoxin, TransMolecular Inc); RetinoStat (Oxford BioScience/Sanofi Aventis); RetinoStat (Oxford BioMedica); adPEDF (GenVec); adenoviral PEDG gene therapy; protein therapeutics, molecular diagnostics; stem cells; non-steroidal inhibitor of CREB regulated transcription coactivator-1 and TORC, e.g., Palomid 529 (P529) (Paloma Pharmaceuticals); antibodies; Isonep; sustained release Lucentis; Macroesis (Buckeye); immunoconjugates (e.g., hl-con1, Iconic Therapeutics); heterocomplex of VEGG linked to a keyhole limpet hemocyanin (e.g., VEGF Kinoid, Neovacs); hESCs; microplasmin, e.g., MIVIS (ThromboGenics); compound regulating lipase gene; Medidur FA (pSivida/Alimera); a small interfering RNA product, e.g., RTP-801i-14 (Pfizer/Quank/Silence Therapeutic); a siRNA targeting hypoxia-inducible genes, e.g, RTP801 (Pfizer/Quark); PTK787; ACE-041 (Acceleron Pharma); rC3-1 (InaCode BioPharmaceutics, Inc.); ACU-4429 (Acucela); ACU-02 (Acucela); a covalently-linked form of zinc monocysteine complex, e.g., Zinthionein (Pipex, Adeona Pharmaceuticals); I-vation (SurModics Inc/Merck); phosphatase-activated tumor vascular targeting agent, e.g., Zybrestat (Oxigene); retinylamine (Case Western University); TRC093 TRC 105 (Tracon Pharmaceuticals); volociximab (Opthotech); E10030 (Ophthotech); SAR 1118 (SARcode Corp); Intelligent Retinal Implant System; RNAi drugs (Traversa, for example); PMX53 (Arana Therapeutics); SMT D004 (Summit Corpic); aptamer therapeutics (Archemix Corp); MC1101 (MacuClear); infra-red light; iCo-007 (iCo Therapeutics); NT-501 (Neurotech Pharmaceuticals); OT-551 (Othera Pharmaceuticals); VPC51299 (Catena Pharmaceuticals); fenretinide (Sirion Therapeutics); an anti-angiogenic and/or angiolytic compound, e.g., Eye Drop (OcuCure Therapeutics); CCR3 Marker (University of Kentucky); Alterase (MedImmune/Catalyst Biosciences); iPS (Japan Kyoto University); CLT-003 (Charlesson); OXY111A (NormOxys Inc.); a photosensitizer (e.g., Photrex, Miravant Medical Technologies); Visudyne with Triamcinolone (QLT); Bevasiranib with ranibizumab (Opko Health); VEGF Trap-Eye (Bayer and Regeneron); AGN745 (Allergan and Merck & Co.); Visudyne with Lucentis, Dexamethasone (QLT); Medidur FA with Lucentis (pSivida); Lucentis with Visudyne (Genentech); TG100801 (Targeted Genetics); ST602 (Sirion Therapeutics) Neurosolve (Vitreoretinal Technologies); an NF-kB inhibitor (e.g., OT551, Othera Pharmaceuticals); DNA-damage-inducible transcript 4 (DDIT4) inhibitor (e.g., RTP801i, Quark Pharmaceuticals and Silence Therapeutics); a C-Kit Receptor Tyrosine Kinase (CD117) Inhibitor (e.g., Armala, GlaxoSmithKline); a Ciliary Neutrophic Growth Factor (CNTF) Receptor Agonist (e.g., NT501, Neurotech); an Alpha7 Non-Neuronal Nicotinic Receptor Antagonist (e.g., ATG003, CoMentis); a slow-released corticosteroid (e.g., Iluvien, Alimera); a Sphingosine-1-Phosphate (S1P) Receptor Antagonist (e.g., Isonep, Lpath); a polyamine analogue (e.g., PG11047, Progen Pharmaceuticals); E10030 with Lucentis (Ophthotech); pigment epithelial derived GF, e.g., AdPEDF (GenVec); an mTOR inhibitor, e.g., Sirolimus (MacuSight); a Non-retinoid visual cycle modulator, e.g., ACU4429 (Otsuka Pharmaceutical/Acucela); a C5 Complement InhibitorNEGF-A Inhibitor, e.g., ARC1905 with Lucentis (Ophthotech); an antisense insulin receptor Substrate 1 (IRS-1), e.g., GS101 (Gene Signal); an alpha(5)beta (1) integrin receptor agonist, e.g., SB267268 (GlaxoSmithKline), Volociximab (Biogen Idec and PDL BioPharma); JSM6427 (Jerini/PR Pharmaceuticals).

The pharmaceutical (or combination of pharmaceuticals) may further comprise a pharmaceutically acceptable carrier. Such pharmaceutical carriers are well known to one of ordinary skill in the art. In some embodiments, the pharmaceutical (or combination of pharmaceuticals) may be administered as a slow-release formulation. Such slow-release formulations are well known to one of ordinary skill in the art, for example the pharmaceutical may be in the form of a vehicle such as a micro-capsule or matrix of biocompatible polymers such as polycaprolactone, polyglycolic acid, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and other polymers such as those disclosed in U.S. Pat. Nos. 6,667.371; 6,613,355; 6,596,296; 6,413,536; 5,968,543; 4,079,038; 4,093,709; 4,131,648; 4,138,344; 4,180,646; 4,304,767; 4,946,931, or lipids that may be formulated as microspheres or liposomes. The formulation and loading of microspheres, microcapsules, liposomes, etc. are standard techniques known by one skilled in the art.

Cannulas for Administration of Pharmaceuticals in Combination with RBS

The cannula may deliver both the RBA and at least one pharmaceutical (e.g., as described above). Administration may be simultaneous or consecutive. The pharmaceuticals may be housed in a chamber 710 (or multiple chambers) disposed in the cannula, for example in the proximal portion, in the handle 140, in the radiation shielding pig, etc. (see FIG. 23). Or, the chamber may alternatively be disposed in the distal portion (e.g., in a "distal pharmaceutical chamber"). In some embodiments, the cannula comprises a first chamber 710 for housing a first pharmaceutical (see FIG. 23). In some embodiments, the cannula comprises a first chamber 710 for housing a first pharmaceutical and a second chamber (e.g., 712) for housing a second pharmaceutical (see FIG. 23A). In some embodiments, the cannula comprises a first chamber 710 for housing a first pharmaceutical, a second chamber (e.g., 712) for housing a second pharmaceutical, and a third chamber for housing a third pharmaceutical.

In some embodiments, the chamber(s) 710 in the cannula are pre-loaded with a fixed volume of the pharmaceutical(s). In some embodiments, the chamber(s) 710 comprise an opening for providing access to the chamber(s) 710, for example for loading the chamber(s) 710 with the pharmaceutical(s). A closing mechanism may be disposed on the opening, wherein the closing mechanism can move between an open position and a closed position for respectively allowing and preventing access to the chamber 710 (e.g., preventing leaking of the pharmaceutical).

The cannula may comprise one or more pharmaceutical orifices 730 for dispensing the pharmaceutical. The pharmaceutical orifice 730 may be disposed on the distal portion 110, for example at or near the tip (see FIG. 24). The pharmaceutical orifice 730 may be disposed adjacent to the treatment position of the RBS.

The chamber(s) 710 housing the pharmaceutical(s) are fluidly connected to one or more pharmaceutical orifices 730. For example, in some embodiments, the first chamber 710 is fluidly connected to a first pharmaceutical orifice 730. In some embodiments, the first chamber 710 is fluidly connected to a first pharmaceutical orifice 730 and the second chamber is also fluidly connected to the first pharmaceutical orifice 730. In some embodiments, the first chamber 710 is fluidly connected to a first pharmaceutical orifice 730 and the second chamber is fluidly connected to a second pharmaceutical orifice. The chamber(s) 710 housing the pharmaceutical(s) may be fluidly connected to the pharmaceutical orifice 730 via a tube 720. The tube 720 may, for example, be a part of the means of advancing the RBS, e.g., guide wire 350, ribbon, memory wire, etc (e.g., see FIG. 24A). Or, the tube 720 may be separate from the means of advancing the RBS (see FIG. 23), e.g., the guide wire 250, ribbon, memory wire, etc.

The cannula comprises one or more advancing mechanisms for advancing the pharmaceutical from the chamber(s) 710 to the pharmaceutical orifice(s) 730, e.g. via the tube 720, and ultimately causing the dispensing of the pharmaceutical. The advancing mechanism may be incorporated into the proximal portion, for example in the handle 140. Non-limiting examples of such mechanisms include pneumatic mechanism (e.g., air pressure), a vacuum mechanism, a slide mechanism, a button mechanism, a dial mechanism, a thumb ring, a graduated dial, a slider, a fitting, a Toughy-Burst type fitting, a plunger (e.g., a solid stick, a piston, a shaft, etc.), a hydrostatic pressure mechanism, the like, or a combination thereof. For example, a plunger mechanism may push the pharmaceutical (e.g., angiogenesis inhibitor) from the chamber to the orifice via the tube. As shown in FIG. 25, the plunger mechanism 760 may comprise a means of advancing both the RBS and the pharmaceutical(s), for example the plunger mechanism 760 may comprise two plunger rings 761, 762. The present invention is not limited to the examples of advancing means described herein, for example FIG. 25 is merely one example of many types of employable advancing means.

The pharmaceutical orifices 730 may be constructed in a variety of shapes, for example shapes such as a circle, a square, an oval, a rectangle, an ellipse, a triangle, or an irregular shape. In some embodiments, the pharmaceutical orifice 730 has an area of about 0.01 mm$^2$ to about 0.1 mm$^2$. In some embodiments, the pharmaceutical orifice 730 has an area of about 0.1 mm$^2$ to about 1.0 mm$^2$. In some embodiments, the pharmaceutical orifice 730 has an area of about 1.0 mm$^2$ to about 10.0 mm$^2$.

In some embodiments, the distal edge of the pharmaceutical orifice 730 is located between about 0.1 mm and 0.5 mm from the tip of the distal portion. In some embodiments, the distal edge of the pharmaceutical orifice 730 is located between about 0.5 mm and 1.0 mm from the tip of the distal portion 110. In some embodiments, the distal edge of the pharmaceutical orifice 730 is located between about 1.0 mm and 2.0 mm from the tip of the distal portion 110. In some embodiments, the distal edge of the pharmaceutical orifice 730 is located between about 2.0 mm and 5.0 mm from the tip of the distal portion. In some embodiments, the distal edge of the pharmaceutical orifice 730 is located between about 5.0 mm and 10.0 mm from the tip of the distal portion 110. In some embodiments, the distal edge of the pharmaceutical orifice 730 is located between about 10.0 mm and 20.0 mm from the tip of the distal portion.

Referring to FIG. 31-37, the present invention features minimally-invasive devices and methods for the delivery of radiation (e.g., beta radiation, e.g., Sr-90, Y-90) to the back of the eye (or other a desired location). In some embodiments, the devices and methods of the present invention deliver radiation to the episcleral surface. In some embodiments, the radiation source is used within a disposable applicator. In some embodiments, the dose is 24 Gy and is given to the target (e.g., wet AMD lesion) over the course of 5 to 7 minutes, depending on the source strength, e.g., 555 to 740 MBq (15-20 mCi). The present invention also features methods of determining the dose delivered to the lesion and nearby normal tissues.

An example of a device of the present invention is shown in FIG. 31. In some embodiments, the device comprises a cannula (e.g., stainless steel, e.g., 1.8 mm diameter) that is shaped to advance around the eye globe under the membrane of Tenon's capsule. In some embodiments, it is connected to a radiation tolerant plastic handle, which serves as a storage vault (or pig) to hold the radiation source while the device is moved into position. In some embodiments, the surgeon positions the tip of the cannula against the sclera directly behind the lesion. In some embodiments, an optical fiber is integrated onto the concave edge of the cannula and is used to transilluminate the globe so the position of the cannula tip may be observed with an indirect ophthalmoscope. In some embodiments, when accurate positioning is achieved, the plunger may be pushed so as to advance the radiation source to a treatment position (the plunger being connected through a flexible cable to the radiation source). As an example, calculations beforehand establish the precise duration of treatment to achieve 24 Gy to the center of the lesion which is less than about 2 mm inside the sclera or less than 3.4 mm from the center of the radiation seed. At the end of the prescribed time, the radiation source (e.g., Sr-90, Y-90, a combination thereof, etc.) may be retracted back into the storage pig using the plunger/cable system and the device slipped out from the patient's eye.

Note in some embodiments, the cannula (e.g., distal portion and proximal portion) is generally solid and the RBS is disposed at the tip of the cannula, e.g., the RBS is not necessarily advanced through the cannula.

In some embodiments, the handle with the integral storage pig is made from radiation tolerant and machinable plastic (Ultem©, a polyetherimide, which is a dense polymer). In some embodiments, since only beta radiations are present, a wall thickness of 11 mm may be adequate to shield them entirely. In some embodiments, no metals are used in order to minimize the production of the more penetrating bremsstrahlung x-rays by the shielding material (this may lead to a lighter weight handheld device). The radiation shielding properties were verified by MCNPX and by measurements.

The device of the present invention may be constructed from a variety of materials. For example, in some embodiments, the device is constructed from a material comprising polyetherimide material (e.g., Ultem®), plastic, glass, (e.g., Gorilla® Glass), acrylic, poly(methyl methacrylate) (PMMA), polysulfone, polycarbonate, polypropylene, stainless steel, aluminum, titanium, elgiloy, lead, the like, or a combination thereof. The present invention is not limited to the aforementioned materials.

In some embodiments, the device of the present invention utilizes a radiation source (e.g., radionuclide brachytherapy source RBS)). In some embodiments, the RBS is encapsulated. In some embodiments, the radiation source (RBS) may comprise Sr-90, Y-90, the like, or a combination thereof. In the figures, SR800 refers to an RBS. In some embodiments, the SR800 RBS comprises four enamel beads, 0.5 mm diameter, impregnated with radioactive 90Sr, which decays by beta radiation to 90Y. In some embodiments, the parent strontium isotope has a maximum beta energy of 546 keV, an average energy of 196 keV, and a half life of 28.8 years while the beta decay from the daughter yttrium isotope has a maximum energy of 2.28 MeV, an average energy of 935 keV and a half life of 64.1 hours. In some embodiments, the two 185 isotopes are in secular equilibrium with the decay rate of the combined source controlled by the 90Sr parent but with the therapeutic beta radiations coming from the daughter 90Y. In some embodiments, the four beads are contained within a stainless steel can with an overall length of 3.1 mm and a diameter of 0.8 mm. In some embodiments, this source, the RBS, may be welded to a flexible metal stainless steel tube. In some embodiments, the RBS is advanced to the tip of the 1.8 mm diameter cannula from its storage pig in the handle using the flex tube and then retracted following therapy. In some embodiments, long-term storage of the source is within an external safe from which it is inserted into the pig just prior to the treatment procedure. In some embodiments, it is returned to the external safe immediately following removal of the applicator from the patient's eye.

As an example, FIG. 33 shows the MCNPX calculated dose distribution in water at 1.5 mm from the center of the RBS, which is representative of a distance at the episclera surface (e.g., the contacting surface of the cannula displaced by the fiber optic, see FIG. 31). This dose, then, represents the greatest dose to normal tissues, that of the external posterior surface of the sclera. FIG. 34 shows the dose distribution at 3.0 mm from the center of the RBS, which is a representative distance of a wet-AMD lesion in the ocular choroid at the position of the macula. FIG. 35 shows the fall off of dose with distance from the source along the central axis; profiles from the MCNPX calculations are presented from 1.0 to 3.5 mm at 0.5 mm intervals. A comparison of the isodose lines generated by MCNPX and measured isodose profiles yields reasonable agreement in terms of shape and approximate scale factors. The isodose lines shown in FIG. 33, FIG. 34, and FIG. 36 are elongated parallel to the direction of the string of four seeds in the cannula (FIG. 36 is rotated 90 degrees from FIG. 33 and FIG. 34).

Example 1

Surgical Technique

The following example describes a surgical procedure for use of the cannulae of the present invention. The eye is anesthetized with a peribulbar or retrobulbar injection of a short acting anesthetic (e.g., Lydocaine). A button hole incision in the superotemporal conjunctiva is preformed followed by a button hole incision of the underlying Tenon capsule 230.

If a cannula 100 comprising a distal chamber 210 is used, a small conjunctive peritomy (as large as the diameter of the distal chamber) is performed at the superotemporal quadrant. A Tenon incision of the same size is then performed in the same area to access the subtenon space.

Balanced salt solution and/or lydocaine is then injected in the subtenon space to separate gently the Tenon capsule 230 from the sclera 235.

The cannula 100 is then inserted in the subtenon space and slid back until the tip 200 is at the posterior pole of the eye. In some embodiments, the cannula 100 comprises a locator 160. The locator 160 indicates when the correct position has been reached. In some embodiments, the cannula 100 comprises a protuberance to act as an indentation tip 600. The surgeon may then observe the indentation tip 600 or simply the indentation in the retina caused by the cannula 100 using indirect opthalmoscopy through the dialated pupil. If the indentation indicates the radiotherapy is not exactly on the underlying the choroidal neovascular membrane, the surgeon may adjust the position of the cannula 100 while directly visualizing the posterior pole with or without the aid of an operating microscope/ophthalmoscope (this adjustment is the "fine positioning" adjustment). In some embodiments, the surgeon adjusts the position of the cannula while the patient's eye is in a primary gaze position. In some embodiments, the surgeon adjusts the position of the cannula while the patient's eye is in any one of the following position: elevated, depressed, adducted, elevated and adducted, elevated and abducted, depressed and adducted, and depressed and abducted.

In some embodiments, the cannula 100 comprises a pilot light source 610 near the tip 210 of the cannula 100 or along the length of the cannula 100. The light may be seen through transillumination and may help guide the surgeon to the correct positioning of the cannula 100. In some embodiments, the light source 610 is directed through the cannula 100 by fiberoptics or by placement of a LED.

In some embodiments, once the cannula 100 is in place, the RBS (e.g., disk 405, seed-shaped RBS 400) is then pushed to the distal portion 110 of the cannula 100. The radiation escapes the cannula 100 through an orifice 500 or a window 510 located on the side/bottom of the cannula 100 adjacent to the sclera 235. In some embodiments, the distal end 320 of the memory wire 300 comprises the RBS, and the radioactive portion of the memory wire 300 is pushed to the tip 200 of the distal portion 110 of the cannula 100. In some embodiments, the memory wire 300 is pushed into the distal chamber 210 or into a balloon.

The RBS (e.g., disk 405) is left in place for the desired length of time. When the planned treatment time has elapsed, the RBS (e.g., disk 405, memory wire 300) is then retracted to its original position. The cannula 100 may then be removed from the subtenon space. The conjunctiva may then be simply reapproximated or closed with bipolar cautery or with one, two, or more interrupted reabsorbable sutures.

The button hole cunjunctiva/tenon incision has several advantages over a true conjunctiva/Tenon incision. It is less invasive, faster, easier to close, more likely to be amenable to simple reapproximation, less likely to require sutures, and causes less conjunctiva scarring (which may be important if the patient has had or will have glaucoma surgery).

Example 2

Fast Radiation Fall Off at the Edge of the Target

After the cannula is placed into position, an RBS is introduced to the sclera region on the eye ball that corresponds with the target (e.g., macula lesion) on the retina. Radionuclide of the RBS is Sr-90, and the RBS has a rotationally symmetrical exposure surface (e.g., circular) (see FIG. 14E). The exposure surface of the RBS has a diameter of about 3 mm. The target is 3 mm in diameter and is about 1.5 mm away from the exposure surface of the RBS.

As shown in FIG. 22, a target that is 1.5 mm away from the exposure surface has a radiation profile where the intensity of the radiation at the edge falls off significantly, i.e., there is a fast fall of at the target edge. When a shielding (deep wall, see FIG. 21) is employed, the radiation fall off at the edge is faster compared to when there is no shielding.

In this example, the ratio of the target diameter to the exposure surface diameter is about 1:1.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A fixed shape cannula comprising:
   (a) a distal portion for placement around a portion of a globe of an eye; wherein the distal portion has a radius of curvature between about 9 to 15 mm and an arc length between about 25 to 35 mm;
   (b) a curved proximal portion having a radius of curvature between about an inner cross-sectional radius of the cannula and about 250 mm;
   (c) an inflection point which is where the distal portion and the proximal portions connect with each other; and
   (d) a handle extending from the proximal portion, the handle lies on an axis such that the axis does not intersect with the distal portion;
   wherein an angle $\theta_1$ between (i) a line $l_3$ tangent to the inflection point between the distal portion and the proximal portion and (ii) the proximal portion is between greater than about 0 degrees to about 180 degrees, wherein said cannula is for placing under a Tenon's capsule.

2. The cannula of claim 1 wherein at least a portion of the cannula is hollow.

3. The cannula of claim 2 having an internal cross sectional shape configured to allow a radionuclide brachytherapy source (RBS) to glide through.

4. The cannula of claim 2 having an internal cross sectional shape that is round or oval.

5. The cannula of claim 2, wherein an advancing mechanism is disposed in the cannula for advancing a radionuclide brachytherapy source (RBS) from a starting position in the cannula to at or near a tip of the distal portion of the cannula.

6. The cannula of claim 5, wherein the advancing mechanism is selected from the group consisting of a guide wire, a non-wire plunger, an air pressure mechanism, a vacuum mechanism, a hydrostatic pressure mechanism employing a fluid, or a combination thereof.

7. The cannula of claim 1, wherein at least a portion of the cannula is solid.

8. The cannula of claim 1, wherein the distal portion and proximal portion are both solid.

9. The cannula of claim 1, wherein the distal portion has a radius of curvature of about 12 mm and the distal portion has an arc length of about 30 mm.

10. The cannula of claim 1 further comprising a radionuclide brachytherapy source (RBS) disposed at a tip of the distal portion.

11. The cannula of claim 10, wherein the tip of the distal portion has a diameter or width that is greater than that of the distal portion.

12. The cannula of claim 1 having an outer cross sectional shape that is round or oval.

13. The cannula of claim 1, wherein the handle comprises a radiation shielding pig for shielding a radionuclide brachytherapy source (RBS).

14. The cannula of claim 1, wherein the cannula further comprises a protuberance disposed on the distal portion.

15. The cannula of claim 1, wherein the distal portion and proximal portion are both hollow.

* * * * *